(12) United States Patent
Lin et al.

(10) Patent No.: US 9,993,576 B2
(45) Date of Patent: *Jun. 12, 2018

(54) CEMENT PRODUCTS AND METHODS OF MAKING AND USING THE SAME

(71) Applicant: Pioneer Surgical Technology, Inc., Marquette, MI (US)

(72) Inventors: Juchui Ray Lin, Bedford, MA (US); Edward S. Ahn, Dover, MA (US); Brian M. Schlossberg, Chestnut Hill, MA (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/670,284

(22) Filed: Aug. 7, 2017

(65) Prior Publication Data

US 2017/0333594 A1 Nov. 23, 2017

Related U.S. Application Data

(63) Continuation of application No. 15/149,986, filed on May 9, 2016, now Pat. No. 9,757,493, which is a continuation of application No. 14/461,138, filed on Aug. 15, 2014, now Pat. No. 9,358,319, which is a continuation of application No. 12/200,918, filed on Aug. 28, 2008, now Pat. No. 8,815,973.

(60) Provisional application No. 60/968,462, filed on Aug. 28, 2007.

(51) Int. Cl.
| | |
|---|---|
| A61L 24/06 | (2006.01) |
| A61K 6/083 | (2006.01) |
| A61K 6/08 | (2006.01) |
| A61L 24/04 | (2006.01) |
| A61L 24/02 | (2006.01) |
| A61K 6/033 | (2006.01) |

(52) U.S. Cl.
CPC ............ *A61L 24/06* (2013.01); *A61K 6/033* (2013.01); *A61K 6/08* (2013.01); *A61K 6/083* (2013.01); *A61L 24/02* (2013.01); *A61L 24/04* (2013.01); *A61L 24/046* (2013.01); *A61L 2300/112* (2013.01); *A61L 2300/412* (2013.01); *A61L 2400/06* (2013.01); *A61L 2400/12* (2013.01); *A61L 2430/02* (2013.01); *A61L 2430/12* (2013.01)

(58) Field of Classification Search
CPC ................................ A61K 6/083; A61L 24/06
See application file for complete search history.

(56) References Cited

U.S. PATENT DOCUMENTS

| | | |
|---|---|---|
| 2,920,971 A | 1/1960 | Stookey |
| 3,117,099 A | 1/1964 | Proops et al. |
| 3,732,087 A | 5/1973 | Grossman |
| 3,981,736 A | 9/1976 | Broemer et al. |
| 4,059,684 A | 11/1977 | Gross et al. |
| 4,239,113 A | 12/1980 | Gross et al. |
| 4,341,691 A | 7/1982 | Anuta |
| 4,554,686 A | 11/1985 | Baker |
| 4,643,982 A | 2/1987 | Kasuga et al. |
| 4,652,534 A | 3/1987 | Kasuga |
| 4,775,646 A | 10/1988 | Hench et al. |
| 4,837,279 A | 6/1989 | Arroyo |
| 4,910,259 A | 3/1990 | Kindt-Larsen et al. |
| 5,204,473 A | 4/1993 | Winter et al. |
| 5,236,458 A | 8/1993 | Ducheyne et al. |
| 5,336,642 A | 8/1994 | Wolcott |
| 5,681,872 A | 10/1997 | Erbe |
| 5,824,331 A | 10/1998 | Usala |
| 5,830,492 A | 11/1998 | Usala |
| 5,834,005 A | 11/1998 | Usala |
| 5,883,153 A | 3/1999 | Roberts et al. |
| 5,914,356 A | 6/1999 | Erbe |
| 6,013,591 A | 1/2000 | Ying et al. |
| 6,071,983 A | 6/2000 | Yamamoto et al. |

(Continued)

FOREIGN PATENT DOCUMENTS

| | | |
|---|---|---|
| WO | WO 02/13767 A2 | 2/2002 |
| WO | WO 02/13768 A2 | 2/2002 |

(Continued)

OTHER PUBLICATIONS

U.S. Appl. No. 12/200,918, filed Aug. 28, 2008.
U.S. Appl. No. 14/461,138, filed Aug. 15, 2014.
U.S. Appl. No. 15/149,986, filed May 9, 2016.
"Standard Specification for Acrylic Bone Cement," *Annual Book of ASTM Standards; Medical Devices*, F 451-99a: 56-62 (1999).
3M ESPE, "Z100™ MP Brochure," (1-5) Retrieved from the Internet on Jul. 28, 2005 from www.matweb.com/search/SpecifiedMaterialPrint.asp?bassnum= PMMM02.
Anderson et al., "Semi-Automated Synthesis and Screening of a Large Library of Degradable Cationic Polymers for Gene Delivery," *Angew. Chem. Int. Ed.*, 42: 3153-3158 (2003).
Anderson et al., "A polymer library approach to suicide gene therapy for cancer," *Proceedings of the National Academy of Sciences of the United State of America*, 101(45):16028-16033 (Nov. 1, 2004).

(Continued)

*Primary Examiner* — Michael Pepitone
(74) *Attorney, Agent, or Firm* — Green, Griffith & Borg-Breen LLP

(57) ABSTRACT

Disclosed are cement products, methods of forming cement using the cement product, and methods of using the cement product in orthopedic and dental applications. Generally, the disclosed cement product includes a first component and a second component. The first component comprises a polymerizable resin comprising ethylenic unsaturated double bond, a suitable glycidyl group and/or a suitable isocyanate group. The second component includes a compound comprising more than one type of amine selected from the group consisting of primary amine, secondary amines, tertiary amines and quaternary amines. Alternatively, the second component includes a compound comprising a suitable mercapto (SH—) group, a hindered amine or a dimethylthiotoluenediamine (DMTDA). Optionally, the cement product includes a filler and/or a bioactive component to promote bone formation.

11 Claims, 26 Drawing Sheets

(56) References Cited

U.S. PATENT DOCUMENTS

| | | | |
|---|---|---|---|
| 6,117,456 | A | 9/2000 | Lee et al. |
| 6,126,922 | A | 10/2000 | Rozzi et al. |
| 6,201,074 | B1 | 3/2001 | Von Gentzkow et al. |
| 6,231,881 | B1 | 5/2001 | Usala et al. |
| 6,261,587 | B1 | 7/2001 | Usala |
| 6,352,707 | B1 | 3/2002 | Usala |
| 6,437,073 | B1 | 8/2002 | Gunatillake et al. |
| 6,544,324 | B1 | 4/2003 | Lyles et al. |
| 6,752,863 | B2 | 6/2004 | Lyles et al. |
| 6,864,337 | B2 | 3/2005 | Yuasa et al. |
| 6,906,113 | B2 | 6/2005 | Baudin et al. |
| 6,939,900 | B2 | 9/2005 | Ario et al. |
| 6,953,594 | B2 | 10/2005 | Lee et al. |
| 6,972,130 | B1 | 12/2005 | Lee et al. |
| 6,987,136 | B2 | 1/2006 | Erbe et al. |
| RE39,196 | E | 7/2006 | Ying et al. |
| 7,275,932 | B2 | 10/2007 | Jin et al. |
| 7,303,814 | B2 | 12/2007 | Lamberti et al. |
| 8,815,973 | B2 * | 8/2014 | Lin ............... A61K 6/08 424/423 |
| 9,358,319 | B2 * | 6/2016 | Lin ............... A61K 6/08 |
| 9,757,493 | B2 * | 9/2017 | Lin ............... A61L 24/06 |
| 2002/0193547 | A1 | 12/2002 | Yuasa et al. |
| 2003/0134933 | A1 | 7/2003 | Jin et al. |
| 2003/0232746 | A1 | 12/2003 | Lamberti et al. |
| 2004/0180986 | A1 | 9/2004 | Bellare et al. |
| 2005/0031578 | A1 | 2/2005 | Deslauriers et al. |
| 2005/0118230 | A1 | 6/2005 | Hill et al. |
| 2005/0197422 | A1 | 9/2005 | Mayadunne et al. |
| 2005/0203217 | A1 | 9/2005 | Pomrink |
| 2005/0238683 | A1 | 10/2005 | Adhikari et al. |
| 2006/0041033 | A1 | 2/2006 | Bisig et al. |
| 2006/0051394 | A1 | 3/2006 | Moore et al. |
| 2006/0147376 | A1 | 7/2006 | Yu et al. |
| 2006/0216323 | A1 | 9/2006 | Knaack et al. |
| 2007/0027285 | A1 | 2/2007 | Gunatillake et al. |
| 2007/0032568 | A1 * | 2/2007 | Lin ............... A61K 6/083 523/116 |
| 2014/0357754 | A1 | 12/2014 | Lin et al. |

FOREIGN PATENT DOCUMENTS

| | | | | |
|---|---|---|---|---|
| WO | WO 2005/013921 | A1 | 2/2005 | |
| WO | WO 2007/019461 | A2 | 2/2007 | |
| WO | WO 2007018220 | A1 * | 2/2007 | ........... A61K 6/0038 |

OTHER PUBLICATIONS

Arote et al., "A biodegradable poly(ester amine) based on polycaprolactone and polyethylenimine as a gene carrier," *Biomaterials*, 28: 735-744 (2007).

Brown, "Solubilities of Phosphates and Other Sparingly Soluble Compounds," *Environmental Phosphorus Handbook*, (Griffith et al., eds.), 203-239 (John Wiley & Sons, New York, NY, 1973).

Burton et al., *Huntsman Corporation Brochure*. 1-105 (Apr. 27, 2005).

Deramond et al., "Temperature Elevation Caused by Bone Cement Polymerization During Vertebroplasty," *Bone*, 25(2 Supplemental): 17S-21S (Aug. 1999).

Farenhorst, "Importance of Soil Organic Matter Fractions in Soil-Landscape and Regional Assessments of Pesticide Sorption and Leaching in Soil," *Soil Sci. Soc. Am. J.* 70: 1005-1012 (May-Jun. 2006).

International Search Report with respect to PCT/US2008/074700, (dated Jun. 8, 2011).

Jagur-Grodzinski et al., "Biomedical application of functional polymers," *Reactive & Functional Polymers*, 39: 99-138 (1999).

Jean et al., "Polyurethane Acrylate/Epoxy-Amine Acrylate Hybrid Polymer Networks," *J. Applied Polymer Science*, 77: 2711-2717 (2000).

Kim et al., "Highly effective and slow-biodegradable network-type cationic gene delivery polymer: Small library-like aproach synthesis and characterization," *Biomaterials*, 27: 2292-2301 (2006).

Kincaid, "Epoxy Polyacrylate Hybrids . . . A Continuing Study," *Resolution Performance Products LLC tech paper*, 1-15 (Nov. 2001).

Kweon et al., "A novel degradable polycaprolactone networks for tissue engineering," *Biomaterials*, 24: 801-808 (2003).

Lin et al., "Novel Bioreducible Poly(amido amine)s for Highly Efficient Gene Delivery," *Bioconjugate Chemistry*, 18 (1): 138-145 (Jan./Feb. 2007).

Lin et al., "Linear poly(amido amine)s with secondary and tertiary amino groups and variable amounts of disulfide linkages: Synthesis and in vitro gene transfer properties," *Journal of Controlled Release*, 116 (2): 130-137 (Nov. 28, 2006).

Liso et al., "Analysis of the leaching and toxicity of new amine activators for the curing of acrylic bone cements and composites," *Biomaterials*, 18(1): 15-20 (1997).

Liu et al., "Novel poly(amino ester)s obtained from Michael addition polymerizations of trifunctional amine monomers with diacrylates: safe and efficient DNA carriers," *Chemistry Communication*, (20): 2630-26301 (Oct. 21, 2003).

Loffredo et al., "The Role of Humic Substances in the Fate of Anthropogenic Organic Pollutants in Soil with Emphasis on Endocrine Disruptor Compounds," *Soil and Water Pollution Monitoring, Protection and Remediation*, 3(23): 69-92 (2006).

Nussbaum et al., "The Chemistry of Acrylic Bone Cements and Implications for Clinical Use in Image-guided Therapy," *J. Vasc. Interv. Radiol.* 15(2): 121-126 (Feb. 2004).

Pressly, "Complications Related to the Use of Bone Cement and Bone Void Fillers in Treating Compression Fractures of the Spine", *FDA Public Health Web Notification*, 1-3 (May 7, 2004).

Provenzano et al., "Bone Cements: Review of Their Physiochemical and Biochemical Properties in Percutaneous Vertebroplasty," *American Journal of Neuroradiology*, 25(7): 1286-1290 (Aug. 2004).

Serbetci et al., "Mechanical and Thermal Properties of Hydroxyapatite-Impregnated Bone Cement," *Turk. J. Med. Sci.*, 30: 543-549 (2000).

Srinivasachari et al., "Effects of trehalose click polymer length on pDNA complex stability and delivery efficacy" *Biomaterials*, 28: 2885-2898 (2007).

Zhong et al., "A versatile family of degradable non-viral gene carriers based on hyperbranched poly(ester amine)s," *Journal of Controlled Release*, 109 (1-3): 317-329 (Dec. 5, 2005).

* cited by examiner

CEMENT PRODUCTS AND METHODS OF MAKING AND USING THE SAME

CROSS-REFERENCE TO RELATED APPLICATIONS

This application is a continuation of U.S. patent application Ser. No. 15/149,986 filed on May 9, 2016, which issued as U.S. Pat. No. 9,757,493 on Sep. 12, 2017, which is a continuation of U.S. patent application Ser. No. 14/461,138 filed on Aug. 15, 2014, which issued as U.S. Pat. No. 9,358,319 on Jun. 7, 2016, which is a continuation of U.S. patent application Ser. No. 12/200,918 filed on Aug. 28, 2008, which issued as U.S. Pat. No. 8,815,973 on Aug. 26, 2014, and claims the benefit of U.S. Provisional Patent Application No. 60/968,462 filed on Aug. 28, 2007, the disclosures of which are incorporated by reference in their entireties.

BACKGROUND OF THE INVENTION

The demand for restorative cement products useful in orthopedic and dental treatments has been increasing, in part, as a consequence of lengthening lifespans and a steadily larger pool of candidates for orthopedic and dental treatments. A second factor driving demand is the increasing tendency among individuals to maintain or adopt a more active lifestyle as they age. This trend makes procedures that use restorative cement products more beneficial and more desirable. A third factor driving the demand for restorative cement products is the development of new techniques that use such cement products.

One disorder that can benefit from improvements to restorative cement products is osteoporosis. Osteoporosis is a chronic bone disease in which the amount of bone is decreased and the structural integrity of bone is impaired. Cancellous bone becomes more porous and cortical bone becomes thinner, making it weaker and more likely to fracture under a normal physiological stress. Eventually, even low impact trauma can result in a fracture and start the victim on a path that will compromise quality of life and, in nearly one third of cases, lead to death.

In the United States, 10 million people have osteoporosis and approximately 32 million more people have low bone mass (called osteopenia), placing them at risk for osteoporosis and osteoporotic fractures. 80% of these people are women. By the age of 65, 50% of women will suffer from osteoporosis, which increases to nearly 100% by age 80. A white female has a 33% chance for a vertebral fracture and approximately a 20-25% chance for a hip fracture in her lifetime. The results are devastating; approximately 15% of osteoporotic patients will have fractures yearly. These 1.5 million fractures occur in 300,000 hips, 700,000 hips, 250,000 wrists, and 300,000 other locations, such as the rib and ankle.

Among the most widely used cement products in orthopedic and dental systems are those based on the polymerizable acrylate resin polymethylmethacrylate (PMMA). PMMA has been used extensively in orthopedic and dental applications. More recent applications include the use of PMMA to treat vertebral compression fractures as a result of trauma or osteoporosis.

PMMA cements are typically prepared from two components: a liquid and a powder. The liquid includes methylmethacrylate (MMA) monomers, an accelerator, and/or an inhibitor. The powder includes PMMA microspheres, a polymerization initiator, and/or a radio-opacifier. This system has been in procedures that polymerize the cement in situ, i.e., at the site of injury being treated. For example, PMMA cements have been used in orthopedic implant surgery to bond the implant to bone and to treat vertebral compression fractures using vertebroplasty and Kyphoplasty™.

However, some concern has been expressed that the exothermic polymerization of PMMA in situ can lead to thermal necrosis. For example, it has been reported that previously studied bone cement products produce a maximum rise in temperature ranging from 80° C. to 124° C. Serbetci et al., "Mechanical and Thermal Properties of I-Hydroxyapatite-Impregnated Bone Cement," Turk. J. Med. Sci., 30: 543-549 (2000). These temperatures exceed the limits for avoiding thermal tissue damage and, thus, have led to concern regarding the heat generated by bone cement polymerization in situ.

As PMMA has found clinical utility in treating osteoporosis, limitations, in addition to its exotherm, have been observed. PMMA cements have also been used to treat bone damage in patients with osteoporosis. According to the National Osteoporosis Foundation, about 700,000 vertebral fractures occur annually; and approximately 270,000 of these fractures are painful and clinically diagnosed. While most patients are treated non-operatively, those that do not respond to conservative treatment can be left with persistent pain and limited mobility. These patients are potential candidates for vertebroplasty or Kyphoplasty™ procedures: two minimally invasive procedures that use PMMA to treat vertebral compression fractures. However during vertebroplasty or Kyphoplasty™, leakage of liquid from low viscosity PMMA bone cements can result in "soft tissue damage as well as nerve root pain and compression. Other reported complications generally associated with the use of bone cements in the spine include pulmonary embolism, respiratory and cardiac failure, abdominal intrusions/ileus, and death. Each of these types of complications has been reported in conjunction with the use of these products in both vertebroplasty and kyphoplasty procedures." 2004 FDA Public Health Web Notification "Complications Related to the Use of Bone Cement in Treating Compression Fractures of the Spine" (issued by Laura Alonge, Office of Surveillance and Biometrics).

Additionally, unreacted components of PMMA cements have been identified as a potential source of toxicity in the body. Thus, besides toxicity due to thermal necrosis, studies have suggested that certain PMMA cement products can produce toxicity due to leaching of unconsumed MMA monomers and/or the polymerization activator. Liso et al., "Analysis of the Leaching and Toxicity of New Amine Activators for Curing of Acrylic Bone Cements and Composites", Biomaterials 18: 15-20 (1997).

The need for new restorative cement products that address the aforementioned concerns is widely recognized in the field.

BRIEF SUMMARY OF THE INVENTION

The present invention provides a number of cement products. One cement product includes a first component and a second component. The first component comprises a polymerizable resin that includes an ethylenic unsaturated double bond. Alternatively, in addition to or instead of the ethylenic unsaturated double bond, the first component comprises a polymerizable resin that includes a suitable glycidyl ether; a suitable glycidyl ester; a suitable ester containing glycidyl ether, a suitable carbonate containing glycidyl ether; and/or a suitable ester or carbonate containing isocyanate. Thus, the first component can also comprise a mixture of ethylenic unsaturated double bonds, glycidyl groups, or isocyanate groups. The second component includes a compound that includes more than one type of amine selected from the group consisting of a primary amine, a secondary amine, a tertiary amine, or a quaternary amine. Alternatively, the second component includes a compound comprising a suitable mercapto (—SH) group or acetoacetonate group. The compounds in the second component can be further functionalized with ester or carbonate groups.

The cement product can also, optionally, further include an additional filler such as an inert filler or a bioactive component that promotes bone growth, provides a tissue scaffold, or provides for the creation of porosity.

In some embodiments, the cement product further comprises a third component including an oxygen-containing ring structure that is capable of reacting in a polymerization reaction with the first component, the second component, or both. In other embodiments, the first component further comprises an oxygen-containing ring structure that is capable of reacting in a polymerization reaction with another group on first component, the second component, or both.

The invention also provides a method of forming cement, the method comprising mixing the first component of the cement product with the second component of the cement product to thereby form cement. The invention further provides a method of treating a patient in need of treatment for a bone defect, wherein the method includes forming cement according to the method of invention and delivering the cement to the defective bone as part of a procedure for repairing the bone defect.

The invention is based, in part, on the discovery that the polymerizable resin of the first component can be combined with the amine-containing compound of the second component in a polymerizing cement-hardening reaction that produces only a mild increase in temperature or no increase in temperature at all. Consequently, even when the product is delivered to the site of restoration and cement-hardening polymerization reactions proceeds in situ, the cement product can be used with less (or without any) concern for thermal necrosis.

The invention is also based, in part, on the discovery that the cement product can be formulated so that, when the components of the cement product are mixed, the resulting cement is injectable. In other words, the first, second, and optional third components can be formulated to produce a cement mix that has the appropriate flowability properties for an injectable cement. Moreover, the improved flowability of the mixture can secure more homogeneous dispersion and mixing of the components upon delivery of the cement. The disclosed first, second, and optional third components can also be formulated so that when combined, the components react to form a crosslinked thermoset network that is ultimately not soluble and not fusible and consumes nearly all monomers and oligomers thus reducing the amount of unreacted starting material or by-products that can leach from the formed cement. Additionally, the amine-containing compound of the second component in the cement product can, in certain embodiments, reduce or eliminate the need for a leachable free radical polymerization initiator and/or a chemical accelerator such as those used in the thermoplastic PMMA bone cement products. Thus, the aforementioned advantages can reduce the risks of chemical tissue damage associated with the cement product disclosed herein.

BRIEF DESCRIPTION OF THE DRAWINGS

FIG. 18 is a graph showing temperature rise relative to time for compositions of the invention that include the indicated mole ratios of PEI (doped with CQ 0.5%) and to ethoxylated (2) bisphenol-A-diacrylate.

DETAILED DESCRIPTION OF THE INVENTION

Figure 1:
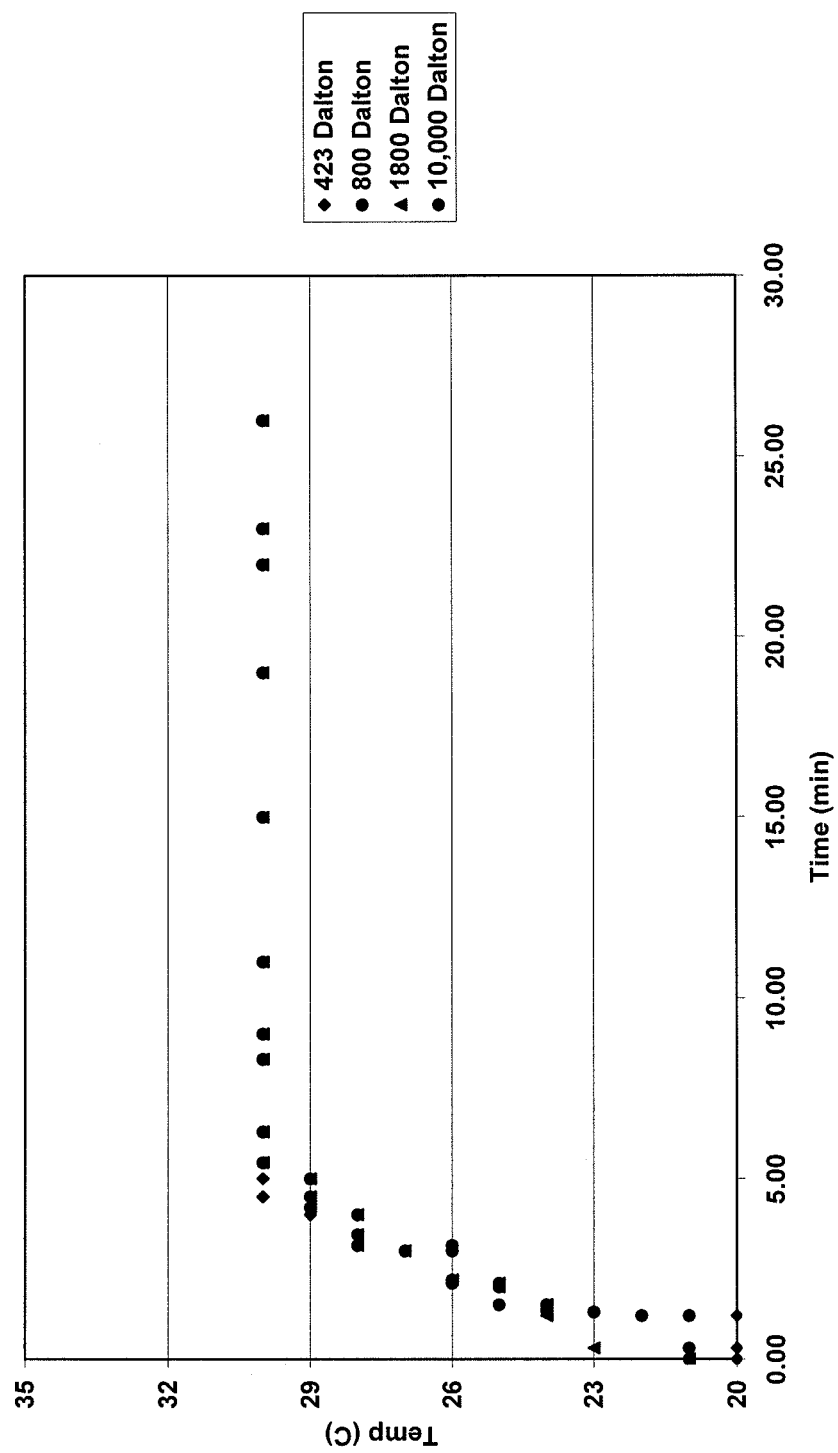
FIG. 1 is a graph showing temperature rise relative to time for compositions of the invention that include indicated molecular weights of PEI.

The cement product of the present invention includes at least a first and a second component. The first component includes a polymerizable resin. In one embodiment, the second component includes a compound comprising more than one type of amine selected from the group consisting of a primary amine, a secondary amine, a tertiary amine, or a quaternary amine. In another embodiment, the second component includes a compound comprising a suitable mercapto (—SH) group or an acetoacetonate group. The aforementioned embodiments of the second component are not mutually exclusive, such that a second component can include varying amounts of compounds of each of the aforementioned embodiments. The cement products of the present invention can further comprise a compound comprising an oxygen-containing ring, e.g., in the first or third component. The cement products of the present invention can also further comprise a filler such as an inert filler or a bioactive component that promotes bone growth. Each component of the cement product can also, optionally, include additional materials.

The first component of the cement product includes one or more biocompatible polymerizable resins. Polymerizable groups are those that can be polymerized. e.g., by Michael addition reactions, by cations such as carbocations, by ion radicals, by free radicals or combinations thereof. Polymerizable groups can also be polymerized by reactions such as (a) a glycidyl (oxirane)-amine ring opening addition reaction. (b) a glycidyl and polyorganosulfide reaction, (c) a glycidyl-carboxylic acid reaction, (d) a glycidyl-glycidyl reaction. Preferred polymerizable resins include one or more ethylenically unsaturated polymerizable group, a glycidyl group, or an isocyanate group.

In some embodiments, preferred polymerizable resins include ethylenically unsaturated double bonds and functional groups known to be biodegradable. Exemplary functional groups include one or more acrylate, methacrylate, ester, ether, amide, carbonate, urethane, oxirane, or hydroxyl groups on the side chain or main chain of such resins. More preferred side chains include imide, isocyanate, phenolic, mercapto, epoxide, diepoxide, aldehyde, anhydride, and dianhydride functional groups.

Sterically hindered functional groups can be used to lengthen working time, set time or cure time. For example, the working times of methacrylates are much longer than acrylates. Furthermore, working times can be lengthened by using lower molecular weight components.

Polymerizable resins suitable for use in the first component include acrylic resins. Suitable acrylic resins include methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate ("HEMA"), hydroxypropyl acrylate, hydroxypropyl methacrylate, tetrahydrofurfuryl acrylate, tetrahydrofurfuryl methacrylate, glycerol mono- and di-acrylate, glycerol mono- and di-methacrylate, ethyleneglycol diacrylate, ethyleneglycol dimethacrylate, polyethyleneglycol diacrylate where the number of repeating ethylene oxide units varies from 2 to 30, polyethyleneglycol dimethacrylate where the number of repeating ethylene oxide units varies from 2 to 30, especially triethylene glycol dimethacrylate ("TEGDMA"), neopentyl glycol diacrylate, neopentylglycol dimethacrylate, trimethylolpropane triacrylate, trimethylolpropane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanediol diacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexamethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2'-bis(4-methacryloxyphenyl)propane, 2,2'-bis(4-acryloxyphenyl)propane, 2,2'-bis[4(2-hydroxy-3-methacryloxy-phe nyl)]propane, 2,2'-bis[4(2-hydroxy-3-acryloxy-phenyl) propane, 2,2'-bis (4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, 2,2'-bis[3(4-phenoxy)-2-hydroxypropane-1-acrylate]propane, propoxylated (2)neopentylglycol diacrylate (Sartomer SR9003), isobornyl methacrylate (Sartomer SR423), aromatic acrylate oligomer (Sartomer CN137), aliphatic allyl oligomer (Sartomer CN9101), dimethylaminoethyl methacrylate (DMAEMA), methylene bisacrylamide (MBA), dimethylaminopropylmethacrylamide, methacrylamidopropyltrimethylammonium chloride, and the like. All products designated herein by reference to "Sartomer" and product number are available from Sartomer Company, Inc. (Exton, Pa.).

Other polymerizable resins suitable for use in the first component include acrylamide, methylene bis-acrylamide, methylene bis-methacrylamide, diacetone/acrylamide diacetone methacylamide, N-alkyl acrylamides, and N-alkyl methacrylamides where alkyl is a lower hydrocarbyl unit. Other suitable examples of polymerizable resins can include polymerizable groups selected from isopropenyl oxazoline, vinyl azalactone, vinyl pyrrolidone, styrene, divinylbenzene, urethane acrylates, urethane methacrylates, polyol acrylates, and polyol methacrylates.

In certain embodiments, the first component can include suitable polylactic acid (D and L), polyglycolic acid, polylactic/polyglycolic acid copolymers, vinyl group containing polyesters such as polypropylenefumarate and polypropyleneitaconate, polydioxane, poly(ε-caprolactone), poly(valerolactone), poly(trimethylene carbonate), poly(tyrosine-carbonates) and poly(tyrosine-arylates), poly(imino carbonates), poly(hydroxybutyrate) (PHB), poly(hydroxyvalerate), poly(tartonic acid), poly(β-malonic acid), polyhydroxycarboxylic acids, polybutyrene succinate, polybutylene adipate, aliphatic disisocyanate based polyurethanes, peptide-based polyurethanes, polyester or polyorthoester based polyurethanes, polyphosphazenes incorporating amino acid ester, glucosyl, glyceyl, lactate or imidazolyl side groups, collagen, chitosan, alginate, cellulose, starches, sugars, polypeptides, polyethylene glycol, vinyl pyrrollidones, acrylam ides and methacrylates or any of their derivates or copolymers, or a copolymer micelle comprising copolymer of polyethylene oxide (PEO), polypropylene oxide (PPO), polyvinylpyridine (PVP), and polystyrene (PS), such as, for example, the triblock copolymer PEO-PPO-PEO, PPO-PEO-PPO, PVP-PS-PVP, PS-PVP-PS, PEO-PS, or PEO-PS-PEO. In certain preferred embodiments, the first component comprises a resorbable material that is flowable at room temperature comprising polymerizable functional groups, such as vinyl group containing polyesters such as polypropylenefumarate and polypropyleneitaconate.

Preferred polymerizable resins suitable for use in the first component include a Michael addition polymerizable or a cationically (e.g., carbocationically) polymerizable group and an oxygen-containing ring. Thus, preferred polymerizable resins include epoxides, oxetanes, oxolanes, C3-C8 cyclic acetals, C3-C12 lactams, C3-C12 lactones, and C5-C20 spirocyclic compounds that contain oxygen atoms in their rings.

Particularly preferred polymerizable resins suitable for the first component include epoxy resins, which feature an oxygen-containing epoxide ring. Exemplary epoxy resins are epoxy acrylates or epoxy methacrylates. Epoxy resins can include monomeric epoxides, polymeric epoxides, and combinations thereof. Epoxy resins can be aliphatic, cycloaliphatic, aromatic, or heterocyclic. Suitable polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendant epoxy groups (e.g., a glycidyl methacrylate polymer or copolymer). Epoxides can be pure compounds or may be mixtures containing one, two, or more epoxy groups per molecule. The "average" number of epoxy groups per molecule is determined by dividing the total number of epoxy groups in epoxy-containing material by the total number of epoxy molecules present. Epoxides used in the first compound can have, for example, an average of at least 1 polymerizable epoxy group per molecule, and preferably an average of at least about 1.5 polymerizable epoxy groups, and more preferably an average of at least about 2 polymerizable epoxy groups.

Accordingly, preferred suitable polymerizable resins for the first component include non-alkoxylated trimethylpropane tri(meth)acrylate (non-alkoxylated TMPT(M)A), alkoxylated trimethylolpropane tri(meth)acrylate (alkoxylated TMPT(M)A) (e.g., ethoxylated (15) TMPT(M)A, ethoxylated (9) TMPT(M)A, ethoxylated (6) TMPT(M)A, ethoxylated (3) TMPT(M)A, propoxylated (3) TMPT(M)A, and propoxylated (6) TMPT(M)A), epoxy acrylate, modified epoxy acrylate (e.g., Sartomer CN115), bisphenol A epoxy methacrylate oligomer (Sartomer CN-151), aliphatic acrylate modifier (Sartomer MCURE 201 and Sartomer MCURE400), glycerol polyglycidyl ether, glycidyl acrylate, glycidyl acrylate of bis-phenol A and the diglycidyl methacrylate of bis-phenol A (bis-GMA), propoxylated (5) glycerol ethoxylated bisphenol-A-triacrylate, (6) ethoxylated (2) bisphenol A diacrylate (E(2)BisDA), and ethoxylated(4) bisphenol A diacrylate (E(4)BisDA)). Useful epoxy-containing materials also include those which contain cyclohexene oxide groups such as the epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, see U.S. Pat. No. 3,117,099, which is specifically incorporated herein by reference in its entirety.

Additionally, preferred suitable polymerizable resins of the first component include (i) glycidyl esters of neodecanoic acid (ERISYS GS-110) and Linoleic Acid dimer (ERISYS GS-120) (both from CVC Specialty Chemicals, Moorestown, N.J.), other glycidyl esters (including those supplied by Aldrich, St. Louis, Mo.) such as diglycidyl stearate, diglycidyl azelate, diglycidyl pimelate, diglycidyl adipate, diglycidyl succinate, diglycidyl oxalate, and olyglycidyl(meth)acrylate, and the like, (ii) glycidyl ethers such as poly[(phenyl glycidyl ether)co-formaldehyde], N,N-diglycidyl-4-glycidyloxyaniline ether, neopentyl glycol diglycidyl ether; Bisphenol A diglycidyl ether, Bisphenol A propoxylate (1 PO/phenol) diglycidyl ether, AraLdite GY 281 (Bisphenol F epoxy resin with moderate viscosity), ARALDITE 506 (Bisphenol A epoxy resin), (AraLdite products are from Huntsman, Woodlands, Tex.), castor oil triglycidyl ether (ERISYS GE-35), sorbitol polyglycidylether (ERISYS GE-60), trimethylpropane triglycidyl ether (ERISYS GE-30), 1,6-hexanediol diglycidyl ether (ERISYS GE-25), cyclohexanedimethanol diglycidyl ether (ERERISYS GE-22), 1,4-butanediol diglycidyl ether (ERISYS GE-21), (all ERISYS™ resins are supplied from CVC Specialty Chemicals (Moorestown, N.J.), trimethylolethane triglycidyl ether, (1,4-butanediol diglycidyl ether), dibromo neopentyl glycol diglycidyl ether, neopentyl glycol diglycidyl ether, ethyleneglycol doglycidyl ether, polyglycidyl methacrylate, polyglycidyl acrylate, polyglycidylmethacrylate, polyglycidylacrylate, EPON™ 8111 (a multifunctional unsaturated epoxy resin supplied by Hexion Specialty Chemicals, Columbus, Ohio and formed by reacting less than 50% w/w bisphenol-A-(epichlorhydrin) epoxy resin (average molecular weight<=700) with more than 50% w/w trimethylpropane triacrylate) and the like, (iii) ester containing glycidyl ether groups such as Cyracure™ UVR 6105 (3,4-epoxycyclohexylmethyl-3,4-epoxycyclohexane) from Dow-Union Carbide Corp (Danbury, Conn.), and the like, (iv) carbonate containing glycidyl ether groups such as DECHE-TOSU (oxirane-spiroorthocarbonate) from Midwest Research Institute (Kansas City, Mo.).

Certain preferred suitable polymerizable resins for the first component feature an oxygen containing ring (e.g., an epoxide) and an acrylate moiety (e.g., acrylate, methacrylate) that are covalently linked and in close proximity to each other as depicted in the structure of Formula 1.

Formula 1

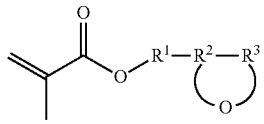

For example, in the structure of Formula 1, the acrylate and the oxygen containing ring structure are separated by the covalent linkage group $R^1$. $R^1$ can be a $C_6$-$C_{20}$ aromatic group, a $C_1$-$C_{20}$ aliphatic group, a $C_3$-$C_{16}$ cyclic group, a polymeric group, or a dendritic group. In addition, $R^1$ can contain one or more polymerizable groups such as epoxides and other suitable oxygen containing rings, ethylenic unsaturated double bonds, and the like. Preferably $R^1$ is any group that does not interpose more than 1, 2, 3, 4 or 5 atoms in the shortest covalent linkage between the acrylate and the oxygen containing ring structure. $R^2$ and $R^3$ represent any substituents capable of forming oxygen containing ring structures. Typically $R^2$ and $R^3$ are each independently selected from CR'R", C=O, O(C=O), NR', and O, wherein R' and R" are each independently selected from the group consisting of H, $C_1$-$C_{12}$-alkyl, $C_3$-$C_{10}$-cycloalkyl, Cl, Br, and OH. When $R^1$, $R^2$ and $R^3$ are each $CH_2$, the structure of Formula 1 represents glycidyl methacrylate (GMA) polymerizable resin.

The polymerizable resin of the first component can include one or more materials that vary from low molecular weight monomeric materials to high molecular weight polymers. The polymers may vary greatly in the nature of their backbone and substituent groups. For example, the backbone may be of any type and substituent groups thereon can be any group that does not substantially interfere with radical or cationic curing at room temperature or body temperature. Permissible substituent groups can include halogens, ester groups, ethers, sulfonate groups, siloxane groups, nitro groups, phosphate groups, and the like. The molecular weight of the epoxy-containing materials can vary from about 20 daltons to about 100,000 daltons, preferably from about 140 daltons to about 30,000 daltons.

The polymerizable resin of the first component can be copolymerized with additional acrylates. For example, when the first component includes an epoxide resin such as GMA, the cement product may also include a second polymerizable resin for copolymerization. Such co-polymerizable resins include methyl methacrylate, ethyl methacrylate, propyl methacrylate, and higher methacrylates, acrylates, ethacrylates, and similar species. Other types of copolymerizable material include epoxide compounds, polyurethane-precursor species, and a wide host of other materials. Still other examples of copolymerizable monomers that can be used in the cement product include methyl-, ethyl, isopropyl-, tert-butyloctyl-, dodecyl-, cyclohexyl-, chlorolethyl-, tetrachloroethyl-, perfluorooctyl-hydroxyethyl-, hydroxypropyl-, hydroxybutyl-, 3-hydroxyphenyl-, 4-hydroxphenyl-, aminoethyl-, aminophenyl-, and thiophenyl-substituted acrylate, substituted methacrylate, substituted ethacrylate, substituted propacrylate, substituted butacrylate, and substituted chloromethacrylate, as well as the homologous mono- and di-(meth)acrylic acid esters of bisphenol-A, dihydroxydiphenyl sulfone, dihydroxydiphenyl ether, dihydroxybiphenyl, dihydroxydiphenyl sulfoxide, and 2,2-bis(4-hydroxy-2, 3,5,6-tetrafluorophenyl)propane. Additional copolymerizable monomers capable of sustaining a polymerization reaction include di-, tri-, and higher ethylene glycol acrylates such as ethylene glycol dimethacrylate, diethylene glycol dimethacrylate, trimethylene glycol dimethacrylate, trimethylol propane trimethacrylate, and the like. In some cases, mixtures of two, three, and more polymerizable species can be combined to good effect.

The second component of the cement product includes a compound comprising more than one type of amine selected from the group consisting of a primary amine, a secondary amine, a tertiary amine, and a quaternary amine. Suitable compounds for the second component include naturally occurring polyamines (such as those from humus), aliphatic polyamines, aromatic polyamines, or mixtures thereof. Polyamines that can be used in the second component include phenylenediamine, ethylenediamine, triethylenetetraamine, and a wide variety of other aliphatic and aromatic diamines that polymerize when mixed with the polymerizable resin of the first component. Suitable compounds for the second component include modified polyamino acids such as polylysines and imidazole-modified polylysines. Suitable polyamines can include branched dendrimers with multiple types of amines, such as polyamidoamine (PAMAM) dendrimers.

Sterically hindered functional groups in the second component can be used to lengthen working time. For example, the inclusion of sterically hindered amine functional groups (e.g., secondary amines) can lengthen set time. Furthermore, working times can be lengthened by using lower molecular weight second component compounds.

Additional amine-containing compounds suitable for inclusion in the second component include monomers or oligomers further comprising ester, ether, amide, carbonate, urethane, or oxirane functional groups on the side chain or main chain. Preferred groups on the side chain or main chain include imide, imidine and isocyanate groups. Suitable amine-containing compounds of the of the second component can include, for example, oleylamine, stearylamine, 2-ethylhexylamine, ethylenediamine, propylenediamine, 1,6-hexamethylenediamine, aminoethanolamine, ethanolamine, propylenetriamine, butylenetriamine, diethylenetriamine, triethylenetetramine, tetraethylenepentamine, N-(3-aminopropyl)-1,3-propanediamine, pentaethylenehexamine, menthanediamine, isophoronediamine, xylenediamine, tetrachloro-p-xylenediamine, methylenedianiline, diaminodiphenylsulfone, polyaniline, N-methylpiperazine, hydroxyethylpiperazine, piperidine, pyrrolidine, morpholine, diethanolamine, streptidine, stilbamidine. 2-deoxystreptamine, dapsone, p-diaminoazobenzene, 4,4'-diaminodiphenyl ether, and the like. Preferred suitable amine-containing compounds of the second component can include DYTEK A™ (2-methyl-1,5-pentamethylenediamine), DYTEK EP™ (2-ethyl-1,3-trimethylenediamine), DYTEK DCH-99™ (o-cyclohexanediamine), and m-phenylenediamine and naturally occurring polyamines such as 1,4-diaminobutane (putrescine), spermidine, and spermine.

Still other amine-containing compound suitable for use in the second component include biological amines such as guanidine, uracil, thymine, adenine, guanine, cytosine, xanthine, and their respective biological nucleotides or derivatives thereof. Exemplary derivative nucleotides include 2,4-diamino-6-hydroxy-pyrimidine and 2,6-diaminopurine. The second component can include oligomers, polymers and copolymers of amino acids such as phenylalanine, tryptophan, arginine, tyrosine, cysteine, or lysine.

In addition to the compounds described herein, the second component can further include free amino acids, such as, phenylalanine, tryptophan, arginine, tyrosine, cysteine, or lysine. For example, amino acids can be blended with or grafted to (e.g., by heating together with) polyamines of the second component. The addition of amino acids can lower the melting point of and render the second component liquid at room temperature. Thus, addition of amino acids to the second component can enhance the handling properties of the cement compositions of the invention. Additionally or alternatively, the addition of amino acids can enhance the curative hardening reaction of the first and second components.

In some embodiments, the invention provides a slowly resorbable or non-resorbable cement product with a second component that includes a naturally occurring polyamine. For example, a slowly resorbable or non-resorbable cement product can comprise (i) a first component that includes Epon 8111™ (e.g. about 100% (w/w)) or a mixture of bisphenol A diglycidyl ether (e.g., about 0-75% or, preferably, 33-67% (w/w)) and trimethylolpropane triacrylate (e.g., about 0-75% or, preferably, 33-67% (w/w)) and (ii) a second component that includes a mixture of spermidine (e.g., about 0-75% or, preferably, 0-33% (w/w)) and, optionally, Dytek A (about 0-67% w/w). Another naturally occurring polyamine can be used instead of some or all of the spermidine in the second component. In the foregoing exemplary slowly resorbable or non-resorbable cement product, the ratio of first component to second component can be about 0.8:1, about 1:1, or about 1:1.2 (mole equivalent:mole equivalent) In the foregoing exemplary slowly resorbable or non-resorbable cement product, the ratio of first component to second component can be 1:0.999 (mole equivalent:mole equivalent).

In other embodiments, the invention provides a resorbable cement product with a second component that includes a naturally occurring polyamine. For example, a resorbable cement product can comprise (i) a first component that includes one or more of the following compounds: sorbitol polyglycidyl ether (e.g., about 0-60% or about 0-40% (w/w)), trimethylolpropane triacrylate, (e.g., about 0-50% or about 0-30% (w/w)) and/or, 1,4-butanediol (e.g., about 0-40% or about 0-20% (w/w)) and (ii) a second component that includes a spermidine (e.g., about 20-100% w/w) and, optionally, Dytek A™ or Dytek EP™ (e.g., about 0-80% w/w). In the first component, 1,6-butanediol or trimethylolpropane benzoate diacrylate can be used instead of some or all of the 1,4-butanediol; and another naturally occurring polymanime can be used instead of some or all of the spermidine in the second component. In such an example, the ratio of first component to second component can be 0.8:1; 1:1; 1:1.2 (mole equivalent:mole equivalent). The ratio of first component to second component can be 1:0.999 (mole equivalent:mole equivalent).

Suitable amine-containing compounds of the second component can also include polyalkyleneamines and derivatives thereof, such as polyethyleneimine (PEI) and PEI derivatives, and polypropyleneimine (PPI) and PPI derivatives, which typically include primary, secondary and tertiary amines. The PEI or PEI derivative can also include quaternary amines. PEI derivatives include ethoxylated PEI, hydroxyethoxylated PEI, and hydroxypropylated PEI. The PEI or PEI derivatives can be branched or linear. Preferably, the PEI or the PEI derivative has a sufficiently low molecular weight that it is a liquid. For example, the PEI or PEI derivative can have an average molecular weight of less than about 200 kDa, less than about 150 kDA, less than about 100 kDa, less than about 90 kDa, less than about 80 kDa, less than about 70 kDa, less than about 60 kDa, less than about 50 kDa, less than about 40 kDa, less than about 30 kDa, less than about 25 kDa, less than about 20 kDa, less than about 15 kDa, less than about 10 kDa, less than about 5 kDa or less than about 2 kDa. The PEI or PEI derivative can have an average molecular of less than about 2 kDa and more than about 0.2 Kda. Preferably, the PEI or PEI derivative has an average molecular weight of less than about 1 kDa and greater than about 0.3 kDa.

It has been found that the concentration of primary amines in PEI correlates with faster set times for certain cement products of the invention. For example, branched PEI with a molecular weights of 800 Da and linear PEI with a molecular weight of 423 Da, which have relatively high concentration of primary amines (i.e., on their chain-ends), have been found set faster than PEI with molecular weight of 10 kDa or 1.8 kDda in cement products of the invention. Thus, preferred cement products of the invention can include PEI and PEI derivatives having average molecular weights of about 800 Da to about 400 Da. Such products have been found to exhibit set times of about 5-15 minutes and harden in less than an hour, e.g., in about 30 minutes.

In combination with a first component compound, branched PEI, branched PPI, and dendrimers containing tertiary amines can be particularly useful for their catalytic effect, which shortens dough time and set time and produces no more than a moderate exothermic temperature increase, if any.

In another embodiment, the second component includes a compound with a mercapto (SH—) group, a hindered amine or dimethylthiotoluenediamine (DMTDA). Generally, mercapto group containing compounds include mercaptouracil, polycysteines, diethoxymethane polysufides.

Diethoxymethane polysufides include compositions with (i) at least about 0.5%, 0.8%, or 1% mercaptans and no more than about 2%, about 3%, about 5% or about 7.7% mercaptans and (ii) a molecular weight of at least about 750, about 1,000, or about 2,000 and no more than 3,000, 4,000, 7,000 or 10,000. Such diethoxymethane polysufides include LP2, LP3, LP23, LP33, LP55, LP56 and LP980 available from Morton International (Woodstock, Ill.), and the like. Mercapto group-containing compounds can be used in their pure form or in combinations as nucleophiles to be reacted with (meth)acrylate type enone functional resins. Hindered amines include sterically hindered amines, which are substituted on the N-atom by, for example, an alkyl, an alkoxy or a cycloalkoxy moiety. Sterically hindered amines include biocompatible formulations of sterically hindered amines disclosed in U.S. Pat. Nos. 5,204,473, and 6,906,113, incorporated herein by reference in their entirety. Hindered amines also include polyaspartate and related compounds offered by Bayer Material Sciences (Pittsburgh, Pa.) with the trade name of Desmophen™ (e.g., Desmophen NH 142). Hindered amines and DMTDA compositions, such as those offered by Albemarle (Baton Rouge, La.) under the trade name Ethacure™ 300 and Ethacure™ 100 are suitable for use in the addition polymerization systems for (meth)acrylates, di-, tri or polyepoxides as well as di-, tri or polyisocyanates.

Optionally, any one of the embodiments of the cement products disclosed herein can further include a third component comprising a compound comprising an oxygen-containing ring. The oxygen-containing ring can be any suitable oxygen-containing ring, for example, any oxygen containing ring described herein. Typically the oxygen-containing ring is selected from epoxides, oxetanes, oxolanes, C3-C8 cyclic acetals, C3-C12 lactams, C3-C12 lactones, and C5-C20 spirocyclic compounds that contain oxygen atoms in their rings.

Desirably the ratio of equivalents of acceptor hydrogen to equivalents of donor hydrogen is from about 0.5:1 to about 1:0.5, preferably about 0.75:1 to about 1:0.75, more preferably about 0.9:1 to about 1:0.9, and most preferably about 1:1. The equivalents of acceptor hydrogen is the average molecular weight of all compounds in the first and optional third components comprising polymerizable groups (e.g., ethylenic double bond groups, oxygen-containing ring groups) divided by the total number of acceptor hydrogen groups. The equivalents of donor hydrogen can be calculated as the average molecular weight of all compounds comprising amine groups (in the second component) divided by the total number of donor hydrogen groups. For example, the "donor" hydrogen equivalent weight in the amine functionality of PEI is 43 Da while the "acceptor" ethylenic unsaturated double bond or oxygen containing ring on GMA monomer (molecular weight is 142 Da), the equivalent weight of each acceptor functionality is 72 Da.

Optionally, any one of the embodiments of the cement products disclosed herein can further include mixing a filler with the additional first, second, and optional third component of the cement product. The filler can be inert, or alternatively the filler can be comprised by the bioactive component described herein. Inert fillers include glass fillers, such as CORTOSS™ from OrthoVita (Malvern, Pa.) that have good strength characteristics. Bioactive components are useful for promoting bone tissue growth around the restorative cement and, preferably, bone tissue ingrowth into the cement. In addition, the bioactive component can serve as a stiffening and strengthening agent for the cement product. Representative documents describing such materials include U.S. Pat. Nos. 2,920,971, 3,732,087, 3,981,736, 4,652,534, 4,643,982, 4,775,646, 5,236,458, 5,336,642, 5,681,872, and 5,914,356, as well as Brown, W. F., "Solubilities of Phosphate & Other Sparingly Soluble Compounds," in Environmental Phosphorous Handbook, Ch. 10 (1973). All of the foregoing patents and reference documents are incorporated herein by reference.

Typically the bioactive component includes a bioactive glass ceramics, Bioglass™ (sold by NovaBone), Cervital™, water-soluble glasses, collagen, grafted bone material such as allografts, autografis, and xenografts, calcium phosphate ceramics, or any other bioactive material known to promote bone tissue formation. The bioactive component can include known bioactive materials such as densified and microporous hydroxyapatite, fluorapatite, oxyapatite, wollastonite, apatite/wollastonite glass ceramics, anorthite, calcium fluoride, calcium sulfate, agrellite, devitrite, canasite, phlogopite, monetite, brushite, octocalcium phosphate, whitlockite, cordierite, berlinite, combeite, tetracalcium phosphate, tricalcium phosphate (TCP) (e.g., α- and β-tricalcium phosphates), amorphous calcium phosphate, dicalcium phosphate, phosphoric acid crystals, disodium hydrogen phosphate, and other phosphate salt-based bioceramics. Preferably the bioactive components are particles that are fully dense having no internal microporosity (lacking percolated micro-boundary layers or micro-voids), a particle size of 0.5 microns or more and 100 microns or less (e.g., about 80 microns or less, about 50 microns or less, or about 30 microns or less), and a surface area of about 50 $m^2/g$ or less, about 25 $m^2/g$ or less, about 10 $m^2/g$ or less, about 5 $m^2/g$ or less, or about 2.5 $m^2/g$ or less. The particle size distribution can be broad, bimodal, or preferably trimodal, which can be less than about 500 microns, with less than about 10% by weight being sub 0.5 microns sized.

Fillers suitable for use in the cement products of the invention can include other bioceramics, graphite, pyrolytic carbon, bone powder, demineralized bone powder, anorganic bone from which organic constituents have been removed and consists mainly of bone mineral material, dentin tooth enamel, aragonite, calcite, nacre, hydroxyapatite, and other calcium phosphate materials. Fillers can also include carbon, collagen, tendon or ligament derived tissue, keratin, cellulose, hydroxyapatite and other calcium phosphates. Generally, fillers can comprise from about 0.1% to about 95% by weight of the cement product prior to mixing.

Fillers can also include resorbable polyester fillers comprised of PGA, PLGA, PLLA, etc. These microspheres will hydrolyze and resorb thereby creating porosity to facilitate tissue ingrowth. Generally, these filler can be spherical to whisker-like tin morphology, 10 nm to 5 mm in particle size and comprised from about 0.1% to about 95% by weight of the cement product prior to mixing.

In some embodiments, the bioactive component is surface modified with one or more coupling groups. Suitable coupling groups can include, for example, alkoxysilanes containing epoxide, amine, or vinyl groups, organic isocyanates, acrylic acids, methacrylic acids, polyacrylic acids, citric acids, zirconates, titanates, diamines, amino acids, and polypeptides.

Other coupling groups for modifying the surface of the bioactive component include silane coupling agents, bisphosphonates and their derivatives, pamidronic acid and salts thereof (e.g., disodium salts), phytic acid, and the like.

In some embodiments, the filler includes one or more of the following biocompatible binders: fibrin glue, fibrinogen, thrombin, mussel adhesive protein, silk, elastin, collagen, casein, gelatin, albumin, keratin, chitin or chitosan, cyanoacrylates, epoxy-based compounds, dental resin sealants, dental resin cements, glass ionomer cements such as IONO-CAP™ and INOCEM™ (Ionos Medizinische Produkte GmbH, Greisberg, Germany), gelatin-resorcinol-formaldehyde glues, collagen-based glues, cellulosics such as ethyl cellulose, bioabsorbable polymers such as starches, polylactic acid, polyglycolic acid, polylactic-co-glycolic acid, polydioxanone, polycaprolactone, polycarbonates, polyorthoesters, polyamino acids, polyanhydrides, polyhydroxybutyrate, polyhyroxyvalyrate, poly(propylene glycol-co-fumaric acid), tyrosine-based polycarbonates, pharmaceutical tablet binders (such as EUDRAGIT™ binders available from Huils America, Inc.), polyvinylpyrrolidone, cellulose, ethyl cellulose, micro-crystalline cellulose and blends thereof, starch ethylenevinyl alcohols, polycyanoacrylates, polyphosphazenes, nonbioabsorbable polymers such as polyacrylate, polymethyl methacrylate, polytetrafluoroethylene, polyurethane, polyamide, and the like. Preferred binders are polyhydroxybutyrate, polyhydroxyvalerate and tyrosine-based polycarbonates.

Additionally, fillers can include (i) calcification-controlling agents, such as, dimethyl sulfoxide (DMSO), surfactants, diphosphonates, aminooleic acid, and metallic ions, for example, iron and aluminum ions, (ii) plasticizers, such as, liquid polyhydroxy compounds, which include mono-acetin, diacetin, and, preferably, glycerol or an aqueous solution of glycerol, (iii) thixotropic thickeners, such as, solutions including polyvinyl alcohol, polyvinylpyrrolidone, cellulosic ester (for example, hydroxypropyl methylcellulose), carboxy methylcellulose, pectin, xanthan gum, food-grade texturizing agent, gelatin, dextran, collagen, starch, hydrolyzed polyacrylonitrile, hydrolyzed polyacrylamide, polyelectrolyte (for example polyacrylic acid salt), hydrogels, and chitosan. Other materials suitable for suspending particles can also be combined with a wetting agent in an amount sufficient to significantly improve the suspension characteristics of each compositions described herein (i.e., a first, second, third, or filler composition), alone or in combination with another composition described herein.

Preferred fillers include leachable inorganic salts such as sodium chloride, magnesium chloride, calcium sulfate, and calcium carbonate. Other fillers include lithium chloride, lithium bromide, sodium bromide, potassium chloride, potassium bromide, rubidium chloride, cesium chloride, lithium iodide, sodium iodide, potassium iodide, rubidium iodide, cesium iodide, rubidium bromide, cesium bromide, lithium sulfate, lithium nitrate, lithium nitrite, lithium phosphate, lithium cyanide, lithium carbonate, sodium sulfate, sodium nitrate, sodium phosphate, sodium cyanide, sodium carbonate, potassium sulfate, potassium nitrate, potassium phosphate, potassium cyanide, potassium carbonate, lithium acetate, lithium benzoate, lithium octanoate, lithium stearate, lithium salicylate, lithium oxalate, sodium acetate, sodium oleate, sodium benzoate, potassium acetate, potassium oleate, potassium lactate, alkali metal salts of phenols such as lithium phenolate, lithium resorcinolate, bisphenol A lithium salt, sodium phenolate, potassium phenolate, sodium methylate, lithium methylate, sodium ethylate, potassium ethylate (and other methylates, ethylates, or alkylates), calcium oxide, magnesium oxide, beryllium oxide, zinc oxide, silicon oxide, carbonates such as ammonium carbonate, barium carbonate, strontium carbonate, hydroxides such as sodium hydroxide, potassium hydroxide, magnesium hydroxide, barium hydroxide, nitrous oxide-activated carbon, ammonia-activated carbon, ammonium thiocyanate, sodium thiocyanate, potassium thiocyanate, magnesium thiocyanate, potassium thiocyanate, zinc thiocyanate, manganese thiocyanate, triethylamine hydrochloride, 2,4,6-tris (dimethylaminomethyl)phenol 2-ethylhexanoate, laurylamine acetate, 1,8-diazabicyclo[5,4,0]undecene-7 phenolate, laurylamine acetate, and the like.

Certain preferred fillers include microspheres (~100 micrometer), sugars such as sorbitol, and mannitol, and water soluble polymers such as polyacrylic acid, polyvinyl alcohol and its copolymers with polyvinyl acetate, polyvinylpyrrolidone, and the like. For some applications, preferred water soluble polymers are those that can be controllably resorbed or released into body fluid and, thus, create a pore structure into which bone tissue can grow.

Fillers for use in conjunction with the cement products of the invention also include bovine bone powder or bovine demineralized bone particles.

In other further embodiments, the filler can include biological and/or pharmaceutical agents to enhance and accelerate bone formation such as BMP's, bisphosphonates, gene delivery vectors (promoting osteogenesis or preventing osteolysis), stem cells (stem cell can engineered by gene delivery vectors to upregulate expression of desired proteins such as BMP's), antibiotics, pain killers, etc. The biological additive can be any suitable biological additive, for example plasmid DNA or RNA or proteins (e.g., bone morphogenetic proteins 2, 4, 7). The pharmaceutical additive can be any suitable pharmaceutical additive, for example bisphosphonates (e.g., alendronate) and cis-platinum, antibiotics, anti-inflammatories, anti-arthritism, erythropoeitin, and the like.

Biological or bioactive agents that can be combined with fillers include collagen and insoluble collagen derivatives (which can be combined, for example, with bovine bone powder or demineralized bone particles). Exemplary collagen and collagen derivatives include those disclosed in U.S. Pat. Nos. 5,824,331, 5,830,492, 5,834,005, 6,231,881, 6,261,587, 6,352,707, and 7,303,814 as well as in U.S. Application Publication Nos. 20030232746 and 20050118230A1, some of which are sold under the trade name E-Matrix™ by the Encelle Division of Pioneer Surgical Orthobiologics (Greenville, N.C.). Each of the foregoing patents and published applications are incorporated by reference herein in their entirety. Additional biological or bioactive agents that can be combined with fillers include amino acids, peptides, vitamins, inorganic elements, co-factors for protein synthesis, hormones, endocrine tissue or tissue fragments, synthesizers, enzymes (such as collagenase, peptidases, oxidases, and the like), polymer cell scaffolds with parenchymal cells, angiogenic agents and polymeric carriers containing such agents, collagen lattices, antigenic agents, cytoskeletal agents, cartilage fragments, living cells such as chondrocytes, bone marrow cells, mesenchymal stem cells, natural extracts, genetically engineered living cells or otherwise modified living cells, and tissue transplants. Still other biological agents include autogenous tissues (such as blood, serum, soft tissue, and bone marrow), bioadhesives, osteoinductive factor, fibronectin (FN), endothelial cell growth factor (ECGF), cementum attachment extracts (CAE), ketanserin, human growth hormone (HGH), animal growth hormones, epidermal growth factor (EGF), interleukin-1 (IL-1), human alpha thrombin, transforming growth factor (TGF-beta), insulin-like growth factor (IGF-1), platelet derived growth factors (PDGF), fibroblast growth factors (FGF, bFGF, and the like), periodontal ligament chemotactic factor (PDLGF), somatotropin, bone digestors, antitumor agents, immunosuppressants, permeation enhancers (e.g., fatty acid esters such as laureate, myristate and stearate monoesters of polyethylene glycol, enamine derivatives, alpha-keto aldehydes), and nucleic acids.

Fillers can also, optionally, include a biostatic/biocidal agent. For example the filler can include one or more of the following antibiotic or antimicrobial agents: erythromycin, bacitracin, neomycin, penicillin, polymycin B, tetracycline, biomycin, chloromycetin, streptomycins, cefazolin, ampicillin, azactam, tobramycin, clindamycin, and gentamicin. Other biostatic/biocidal agents include povidone, sugars such as dextran, glucose and mucopolysaccharides, and the like. Still other biostatic/biocidal agents include antiviricides, such as those which are effective against HIV and hepatitis. Preferred biostatic/biocidal agents are antibiotics.

The amount of filler added can represent from about 10 to about 95% by weight of total cement mix. For example, preferably an inert filler represents from about 65% to about 85% by weight of total cement mix. Preferred densified microcrystalline and nanocrystalline bioactive hydroxyapatite, tricalcium phosphate, and bioceramic content can range from about 10 to about 99% by weight, preferably less than 85% by weight, more preferably from about 35% to about 80% by weight, for example, from about 50% to about 80% by weight of that filler.

Preferably, the bioactive component includes a nanocrystalline and/or poorly crystalline apatite material, such as hydroxyapatite or another apatitic calcium phosphate. Nanocrystalline and/or poorly crystalline apatite materials have been described, for example, in U.S. Pat. Nos. 6,117,456, 6,953,594, 6,013,591 (which has been reissued as U.S. Reissue No. RE 39,196), and U.S. Pat. No. 6,972,130. The foregoing patent documents are incorporated herein by reference in their entirety. Nanocrystalline apatite material is also commercially available, for example, from Angstrom Medica (Woburn, Mass.). In certain embodiments, the bioactive component includes nanocrystalline hydroxyapatite (nHA) whisker crystals. These nHA crystals can form a fibrous network throughout the polymerized cement that reinforces the cement under compressive loads.

Batches of nHA whisker can be synthesized in reactors by feeding 0.167 M solution of reagent grade $Ca(NO3)2.4H2O$ (CaN) (Fluka Chemie AG, Buchs. Switzerland) onto a well-mixed solution of 0.100 M $(NH4)2HPO4$ (NHP) (Fluka) and aging for 100 hours. Production of nHA whisker can be optimized by controlling temperature and concentration of starting materials. Optimal production occurs at temperatures of about 25° C. to about 200° C., more preferably about 60° C. to about 120° C., and even more preferably about 80° C. to about 100° C., which allows the growth of anisotropic nHA crystals having multiple different aspect ratios that are greater than 1. For example, batches of nHA crystals can have aspect ratios (length:diameter) ranging from about 1.5:1 to about 1000:1, from about 2:1 to about 500:1, from about 3:1 to about 250:1, from about 4:1 to about 200:1, from about 5:1 to about 150:1, from about 6:1 to about 125:1, from about 7:1 to about 100:1, from about 8:1 to about 75:1, from about 9:1 to about 60:1, or from about 10:1 to about 50:1. Generally, production temperatures should not exceed the boiling point of the reaction mix. Reactant concentration can also be controlled by adjusting temperature, i.e., by raising the temperature to remove water and thereby increase reactant concentration. For example, the reaction can be optimized by comparing the nHA produced in a reaction after 5% water removal, 10% water removal, and 15% water removal. The particle size of these batches can be determined using laser diffraction. Surface area and porosity measurements are obtained using nitrogen gas adsorption. Particle settling data can also be obtained. Whisker crystal size and morphology of the hydroxyapatite are confirmed using transmission electron microscopy.

Following chemical precipitation and aging, the powders can be recovered by centrifugation and washed with aqueous solvent to remove residual ionic species. Subsequently, these powders can undergo a second series of washes with organic solvent to remove any remaining precipitation solvent. After removing residual solvent, the resulting precipitate can be re-suspended in an organic monomer, oligomer, or prepolymer solution to prevent hard agglomeration or alignment of whisker particles and, thereby, produce a highly dispersed suspension of nHA whiskers that can be used in the bioactive component of the cement product described herein.

The nHA whiskers of a bioactive component can also be sheared into agglomerated bundles of highly aligned whiskers of different particle size, particle density, and porosity. The nHA powder recovered by centrifugation can be washed as described above, except that instead of the final resuspension in solvent, the excess organic solvent can be removed from the powder, and shear forces applied to allow nHA whiskers to align. Shear forces for this secondary processing technique can be applied using a centrifuge, a pigment mixer and a planetary ball mill.

These two processing (non-sheared and sheared) preparations can produce nHA whiskers having different in particle size, surface area, and porosity, all of which will influence handling and volume loading in the polymer system, as well as the properties of the final cement product that includes such nHA whiskers. Thus, the properties of nHA whiskers can be optimized so that when mixed with the first and the second component of a cement product disclosed herein, the resulting cement has the viscosity and flowability characteristics that are appropriate for the application in which the cement is to be used. For example, the properties of nHA whiskers can be optimized for use in different injectable embodiments of the cement product of the invention. Such injectable embodiments include those suitable for injection during orthopedic and dental procedures.

The first, second, and optional third component described herein and, optionally, the filler described herein desirably are selected so as to provide a thermosetting cement product that is mildly exothermic, is isothermic, or is mildly endothermic. Therefore, the cement product disclosed herein can be used to treat bone defects with less concern for thermal necrosis than is associated with the more exothermic restorative cements that are currently available. It has been reported that thermal necrosis of bone tissue can occur when temperatures surpass 50° C. for more than one minute. Provenzano et al., "Bone Cements: Review of Their Physiochemical and Biochemical Properties in Percutaneous Vertebroplasty," Am J. Neuroradiol. 25: 1286-1290 (2004). Thus, preferably, the first component, the second component, and, optionally, the bioactive component are selected so that when the components are mixed to form a bone cement, the polymerization (i.e., cement hardening) reaction does not rise in temperature or, alternatively, produces a mild rise in temperature that is insufficient to heat the surrounding tissue to a temperature that exceeds 50° C. for more than one minute.

In certain embodiments of the cement product disclosed herein, the first component, the second component, and optionally, the third component and/or the filler are selected so that when the components and, optionally, the filler are mixed, the resulting polymerization and crosslinking reaction produces a rise in temperature that does not exceed 60° C., 59° C., 58° C., 57° C., 56° C., 55° C., 54° C., 53° C. 52° C., 51° C., 50° C., 49° C., 48° C., 47° C., or 46° C. for a period of two minutes. In certain more preferred embodiments of the cement product disclosed herein, the first component, the second component and, optionally, the third component and/or the filler are selected so that when they are mixed, the resulting polymerization reaction produces a rise in temperature that does not exceed 45° C., 44° C., 43° C., 42° C., 41° C., 40° C., 39° C., 38° C., 37° C., 36° C., 35° C., 34° C., 33° C., 32° C., 31° C., or 30° C. for a period of two minutes. In certain still more preferred embodiments of the cement product disclosed herein, the first component, the second component and, optionally, the third component and/or the filler are selected so that when the components are mixed, the resulting polymerization reaction produces a rise in temperature that does not exceed 29° C., 28° C. 27° C., 26° C., 25° C., 24° C., 23° C., 22° C., 21° C., or 20° C. for a period of one minute. In certain most preferred embodiments of the cement product disclosed herein, the first component, the second component and, optionally, the third component and/or the filler are selected so that when the components are mixed, the resulting polymerization reaction produces a rise in temperature that does not exceed 19° C., 18° C. 17° C., 16° C., 15° C., 14° C., 13° C., 12° C., 11° C., or 10° C. for a period of one minute. The rise in temperature can be measured at room temperature (about 25° C.) or at body temperature (about 37° C.). The rise in temperature can be measured according to techniques described in, for example, "Standard Specification for Acrylic Bone Cement" ASTM F 451-99 from ASTM International (West Conshohocken, Pa.), Serbetci et al., "Mechanical and Thermal Properties of Hydroxyapatite-Impregnated Bone Cement," 30: 543-549 (2000) and Deramond et al., "Temperature Elevation Caused by Bone Cement Polymerization during Vertebroplasty," Bone, S25:S17-S21 (1999), which is specifically incorporated by reference herein in its entirety.

The following theoretical considerations may be useful in the selection of a first, second, and optional third component that, when mixed, have optimally low exothermic profile. Without desiring to be bound by theory, it is believed that the components disclosed herein each includes material with multiple functional groups that, when mixed, participate in multiple endothermic and/or isothermic reactions that consume at least some of the energy generated by exothermic polymerizing reactions. In other words, the polymerization reactions of exothermic function groups are used at the molecular level to initiate endothermic or isothermic reactions of different reactive groups. This tandem sequence of exothermic and endothermic/isothermic reactions can be optimized by matching the characteristic thermal zone of the exothermic function groups with that of the endothermic/isothermic function groups, thereby reducing or eliminating the global temperature increase of the polymerization reaction. For example, mixing the first component and the second component can produce (i) mildly exothermic ring-opening reactions with the amino groups of the second component as well as (ii) carbocationic, onium formation, and/or Michael additions, which are endothermic or adiabatic. Alternatively, a mildly exothermic ring-opening reaction can occur with a sulfur group of dimethylthiotoluenediamine (DMTDA) or mercapto-containing compounds or the hindered amine compound of a second component.

The first and second components and, optionally, the third component and/or the filler described herein can all be selected to provide a thermosetting cement product that is suitable for injection. The first, second, optional third component and optional filler can be selected to provide the viscosity and flowability characteristics that are appropriate for the application in which the cement is to be used. Relatively low viscosity, syringable cement products (e.g., syringable pastes) are suited for filling bony defects, fracture repairs, and implant fixations and revisions. Syringable cement products pastes should flow to fill voids, and crevices, and adhere tightly to the surface of the bone, tissue, or implant. Preferably, a syringable paste has a viscosity suitable for injection through a 4-18 gauge needle, e.g., a 6-12 gauge needle. Flowability can be important for tight adherence and removal of micromotion when implant securing is being achieved. The lack of implant motion can reduce inflammation and determine the success of the implant system over time. Higher viscosity pastes are desirable for larger, load bearing bone defects and easily accessible fracture sites. A "putty" can be manipulated, sculpted and cured in place with immediate high strength capability. Oncological bony defects are well-suited for highly loaded, highly bioactive composites. The use of hand mixed pastes of the first and second component can also facilitate the addition of medicaments, antibiotics, or bone growth factors, e.g., prior to injecting or otherwise applying the pastes.

In certain embodiments of the cement product, the first, second, and optional third components described herein and, optionally, the filler are selected so that, when mixed, they form a cement having a desirable setting time and/or desirable mechanical strength. Desirable setting times vary according to the cement's intended application. Desirable setting times can include from about 1 to about 30 minutes (again depending on the application). For certain injectable applications desirable setting times can range from about 2 to about 25 minutes, from about 3 to about 20 minutes, or from about 5 to about 15 minutes.

Desirable mechanical strength will also vary according to the cement's intended applications. Moreover, the type and amount of filler can greatly influence one more type of mechanical strength. Desirable mechanical strength properties include the following. Compressive strength can be from about 20 MPa to about 250 MPa. The compressive strength typically is from about 50 MPa to about 250 MPa. Generally, compressive strength increases with the amount of filler included. When the cement does not include a filler, the compressive strength can be from about 20 MPa to about 100 MPa, e.g., typically from about 50 MPa to about 100 MPa. When the cement includes a filler, the compressive strength typically is from about 100 MPa to about 250 MPa. Preferably the compressive strength is about 50 MPa or more, about 100 MPa or more, or about 150 MPa or more. A preferred tensile strength is from about 10 to about 100 MPa (e.g., about 20 MPa or more, about 40 MPa or more, or about 60 MPa or more). A preferred shear strength is from about 30 MPa to about 150 MPa (e.g., about 50 MPa or more, about 80 MPa or more, or about 110 MPa or more). A preferred flexural strength is from about 20 MPa to about 100 MPa (e.g., about 30 MPa or more, about 40 MPa or more, or about 50 MPa or more). A preferred infinite compression fatigue is from about 20 MPa to about 150 MPa (e.g., about 40 MPa or more, about 70 MPa or more, or about 100 MPa or more). A preferred tensile fatigue is from about 5 MPa to about 40 MPa (e.g., about 10 MPa or more, about 20 MPa or more, or about 30 MPa or more). The compression modulus typically is in the range of about 20 MPa to about 5 GPa, preferably in the range of about 50 MPa to about 2 GPa. And most preferred in range of about 100 MPa to about 1 GPa. The deformation percentage ranges from about 10% to about 90%, preferably from about 20% to about 80% and most preferably from about 30% to about 50%.

The different types of mechanical strengths can be measured according to tests known in the art, such as ASTM F451-99a (Standard Specification for Acrylic Bone Cement) ASTM D695-02a (Test method for compressive properties of rigid plastics), ASTM C-773-88 (Standard Test Method for Compressive (Crushing) Strength of Fired Whiteware Materials), C1424-99 (Standard Test Method for Monotonic Compressive Strength of Advanced Ceramics at Ambient Temperature). ASTM tests are published by ASTM International (West Conshohocken, Pa.).

Desirable cure and set time will also vary according to the cement's intended applications. Cure time can refer to the time needed to achieve maximum compressive strength. Set time can refer to the time needed to achieve a dry-to-touch finish of cement. Moreover, the type and amount of filler and ratios of various components can greatly influence cure and set times. For some applications preferable set times are from about 5 minutes to about 24 hours (e.g., from about 5 minutes to about 20 hours, from about 5 minutes to about 12 hours, from about 5 minutes to about 6 hours, from about 5 minutes to about 3 hours, from about 5 minutes to about 1.5 hours, from about 5 minutes to about 45 minutes). Tests for determining a dry-to-touch finish (tack-free time) can include: ASTM C679-03 (Standard Test Method for Tack-Free Time of Elastomeric Sealants) and ASTM D2377-00 (2008) Standard Test Method for Tack-Free Time of Caulking.

An alternative measure of cure time is time to 50% of maximum compression strength. For some applications, a preferable 50% strength cure time can be up to about 20 hours (e.g., about 16 hours, about 12 hours, about 8 hours, about 4 hours, about 2 hours, about 1 hours, or about 30 minutes).

Furthermore, the preferred cement will maintain at least about 5% to 100% of its initial strength (e.g. from about 5% to about 75%, from about 5% to about 50%, from about 5% to about 30%, from about 5% to about 15% of initial strength) for at least about 6 months (e.g. about 12 months, about 18 months, or about 24 months).

When simulated aging experiments are performed in body fluids, simulated body fluids, DI water, TRIS Buffer, Saline Buffer, Ringer's Lactate, Phosphate Buffer Solution with a pH from about 4 to about 8.5 on the cement, the preferred pH of the fluids when the cement is submerged in the fluid for a minimum about 2 days (e.g., about 4 days, about 1 week, about 1 month, about 1 year) is at a pH of about 4 to about 8.5 (e.g., from about 4 to about 8, from about 5 to about 8).

According to its application, a cement of the invention can be designed to swell when immersed in body fluids, simulated body fluids, DI water, TRIS Buffer, Saline Buffer, Ringer's Lactate, or Phosphate Buffer having PH of from about 4 to about 8.5. The cement can be designed to swell from slightly more than 0% to about 500%.

The relative reactivity of functional groups in the first component towards functional groups of the second component can be exploited to control the set time and flowability properties of cement products of the invention. For example, compared to glycidyl groups, acrylate functional groups in the first component typically react faster with primary amines in the second component of the invention. Thus, a second component with a high ratio of primary amines typically sets more quickly when combined with a first component that includes mostly acrylate functional groups relative to a first component that includes a higher proportion of glycidyl groups (assuming that amine reactive groups are not in excess of first component reactive groups). However, increasing the ratio of secondary and/or tertiary amines in the second component typically slows down the set time of a cement product that includes mostly acrylate functional groups in the first component, since acrylates are not as reactive to secondary and tertiary amines. Glycidyl groups, which are more reactive to secondary and tertiary amines, can be included in the first component to consume unreacted secondary and/or tertiary amines. Furthermore, since the reaction of glycidyl groups with amines is typically slower than that of acrylates with primary amines, set times can be increased by reducing the number available acrylate-primary amine reactions and increasing the number of available glycidyl-amine reactions in a cement product. Thus, the relative amounts of differently reactive functional groups in the cement products of the invention can be used to control set time and flowability.

The relative reactivity of functional groups in the first component towards functional groups of the second component can also be exploited to control swelling and/or resorption properties of the cement products of the invention. Cement products that include an excess of amine functional groups and/or amine functional groups that are unreactive with first component functional groups, can promote swelling and/or resorption of the cement products of the invention. Excess and/or unreacted amines from the second component can absorb water, and thereby increase swelling of a cement product used in an aqueous or moist environment. Furthermore, unreacted excess amines can promote degradation and resorption of a cement product of the invention when placed the body and exposed to aqueous bodily fluids.

Table 1 summarizes certain relationships between functionalities associated with certain components of the invention and how the properties of ambient temperature Michael addition reaction involving those functionalities. Accordingly, the relationships can be used as a guide to select a first and/or second component of the invention suitable for use in a particular application.

TABLE 1

| FUNCTIONALITY | POTENTIAL ADVANTAGES | POTENTIAL DISADVANTAGES |
|---|---|---|
| Methacrylates | Higher Tg | Brittle |
| | Harder | Slower set |
| | Side chain hydrolyzed to form calcium ion binding carboxylic acid | Distinct smell Exothermic |
| Acrylates | Flexible | Lower Tg |
| | Fast set | Soft |
| | Side chain hydrolyzed to form calcium ion binding carboxylic acid | Triacrylate and tetraacrylates extremely fast set. |
| Alkoxylation: Ethoxylate/propoxylate | Less irritating* Hydrophilic moiety | Lower Tg, Softer finish |
| Aliphatic ester linkage | Bioresorbable | Fast hydrolysis |
| Aromatic ester linkage | Bioresorbable Hydrophobic moiety | Tend to darken over time |
| Difunctionality | Good working time with acrylates | Sluggish for methacrylates Some smell |
| Tri-, tetra-functionality | Short working time | Hard finish |
| Imine and derivatives | Cationic Phosphate binder Hydrophilic | Slight smell |

TABLE 1-continued

| FUNCTIONALITY | POTENTIAL ADVANTAGES | POTENTIAL DISADVANTAGES |
|---|---|---|
| Polyamines | Fast cure<br>Hard finish | Exothermic cure<br>Smell |

In some embodiments, the first, second, and third components can be a liquid or a solid at room temperatures. In preferred embodiments, the first, second, and third components can form upon combination flowable material and can be comprised of solid and/or liquid components.

The cement product of the invention can be packaged together, e.g., in a kit, such that the first, second, and optional third components are not mixed until ready to use. For example, the first, second, and optional third components can each be packaged in a separate container. Alternatively, the first, second, and optional third components can each be packaged in a separate chamber of the same container, e.g., a dual chambered self-mixing syringe. More generally, syringes and other devices adapted for injecting cement formed from the first, second, and third components described herein are known in the art. The bioactive component can, optionally, be packaged with the first component only, with the second component only, with the third component if present, separately from each of the first, second and optional third components, or divided between two or more components.

In some embodiments, the cement product of the invention can be used without chemical additives such as an initiator, a catalyst, and/or a stabilizer. In other embodiments the cement product can include significantly smaller amounts of such additives. These embodiments can be used to decrease the risk of chemical necrosis associated with the product.

In other embodiments, the cement product of the invention further includes one or more additives, such as, an initiator, a catalyst, and/or a stabilizer, to optimize the working and setting times of the cement product. Such additives, which are known in the art of restorative cements, include heat curing catalyst and photoinitiators. For example, the cement product of the invention can further include a quinone photoinitiator in an amount ranging from about 0.01% to about 10% by weight of the compound of the second component. More preferably, the quinone is present in an amount of about 0.1% to about 5% by weight of the compound of the second component. Preferred quinone photoinitiators include alpha diketone(quinones). A more preferred quinone photoinitiator is camphoroquinone. Other photoinitiator systems include a 2-benzyl-2-(dimethyl-amino)-4'-morpholino-butyrophenone, or mixtures of 2-hydroxyethy-2-methyl-1-phenyl-1-propanone and diphenyl (2,4,6-trimethylbenzyl) phosphine oxide. In certain embodiments, the cement product can include the appropriate relative amounts of (i) butylated hydroxytoluene (BHT) stabilizer, (ii) benzoyl peroxide (BPO) catalyst, and (iii) the compound of the second component, wherein the appropriate relative amounts are selected to optimize working time and setting time.

Initiator or accelerator systems that can be used include those with BPO, 2,2'-Azobis (2-methylpropionitrile) (AIBN), and/or N,N dimethyltoluidine.

The cement products of the invention can further include one or more tertiary amine containing catalysts. For example, tertiary amine containing catalyst can be provided with the second component. Suitable tertiary amine containing catalyst can include N,N'-dimethylpiperazine, N,N'-bis[(2-hydroxy)propyl]piperazine, N-alkylmorpholine, N,N,N',N'-tetramethyl-1,3-butanediamine, hexamethylenetetramine, N,N-dimethylcyclohexylamine, N-alkylpiperidine, N-methyldicyclohexylamine, N-alkylpyrrolidine, tetramethylguanidine, N,N-dimethyl-p-toluidine, tri-n-butylamine, tri-2-ethylhexylamine, triamylamine, triethanolamine, 2-dimethylamino-2-hydroxypropane, tri-n-butylamine, i-hydroxyethyl-2-heptadecylgloxysaridine, dimethylaminoethanolamine, dibutylaminoethanolamine, 2-methylimidazole, 2-phenylimidazole, 1,8-diaza-bicyclo[5,4,0]undecene-7,1,5-diazabycyclo[4,3,9]nonene, α-picoline, β-picoline, γ-picoline, 3,5-lutidine, purine, zanthine, naphthyridine, quinoxaline benzyldimethylamine, 2-(dimethylaminomethyl)phenol, 2,4,6-tris(dimethylaminomethyl)phenol, N,N-dimethylaniline, N,N,N',N'-tetramethyldiaminodiphenylmethane, N,N-dimethyltoluidine, tetradthylammonium iodide, lauryltrimethylammonium chloride, distearyldimethylammonium chloride, and alkylbenzyldimethylammonium chloride. Preferred tertiary amine catalysts include triethylenediamine (or DABCO™ (Aldrich, St. Louis, Mo.)), N,N-dimethyl-p-toluidine, 1,4-Diazabicyclo[2.2.2]octane (or DABCO™ 33-LV (Aldrich)), and N,N,N',N'-tetrakis (3-aminopropyl)-1,4-butanediamine, (DAB-Am-4 or polypropyleneiminetetraamine dendrimer, generation 1.0 (Aldrich)). The foregoing amines can provide a catalytic effect that shortens dough time and set time and produces no more than a moderate exothermic temperature increase, if any.

Other catalysts that can be used in the cement products of the invention include trimethylphosphine, triethylphosphine, triisopropylphosphine, tri-n-butylphosphine, tri-1-butylphosphine, tri-sec-butylphosphine, tris-2-ethylhexylphosphine, trioctylphosphine, trioctadecylphosphine, butyldiphenylphosphine, methylbutyloctylphosphine, dimethyloctylphosphine, triphenylphosphine, tricyclohexylphosphine, tribenzylphosphine, benzyldimethylphosphine, tris-2-phenylethylphosphine, tricyclopentylphosphine, dimethyllaurylphosphine, tritolylphosphine, tris-p-tert-butylphenylphosphine, hexamethylphosphoramide, methyltriphenylphosphonium iodide, ethyltriphenylphosphonium iodide, propyltriphenylphosphonium iodide, n-butyltriphenylphosphonium iodide, n-decyltriphenylphosphonium iodide, methyltributylphosphonium iodide, ethyltriphenylphosphonium chloride, n-butyltriphenylphosphonium chloride, ethyltriphenylphosphonium bromide, tetrakishydroxymethylphosphonium chloride, tetraphenylphosphonium chloride, oxazole, furazane, thiazole, and indazole.

The first, second, and optional third components can also be selected so that when combined, the components react to form a crosslinked thermoset network that is ultimately not soluble and not fusible and consume nearly all monomers and oligomers thus reducing the amount of unreacted starting material or by-products that can leach from the formed cement. For example, in preferred embodiments, at least 80%, 85%, or 90% of reactants are converted to into the polymer network. More preferably, 95%, 96%, 97%, 98%, 99%, or 100% of reactants are converted. Additionally, the amine-containing compound of the second component in the cement product can, in certain embodiments, reduce or eliminate the need for a leachable free radical polymerization initiator and/or a chemical accelerator such as those used in the thermoplastic PMMA bone cement products. Thus, the aforementioned advantages can reduce the risks of chemical tissue damage associated with the cement product disclosed herein.

In another aspect, the invention provides a method of forming cement. The method includes providing the first component and the second component of the cement product described herein and mixing the two components to thereby form cement. Optionally, the method can further include combining the bioactive component of the cement product described herein.

As described above for the cement product, the method of forming cement disclosed herein includes preferred embodiments of the first component, second component and optional bioactive component. Preferred embodiments of the first component for use in the method include an epoxy resin, while more preferred embodiments of the first component include both an epoxide and a glycidyl ether group as shown in Formula 1. Even more preferred embodiments of the first component include GMA and bis-GMA. More preferred embodiments of the second component for use in the method include PEI or a derivative thereof. In the most preferred method of forming cement, the first component includes GMA or bis-GMA or ethoxylated bisphenol A di(meth)acrylate and the second component includes PEI, PEI doped with 0.1-5% by weight of camphorquinone, or a derivative thereof.

The invention also provides a method of treating a subject in need of treatment for a bone defect. As used herein the term "subject" can include a human or another animal, e.g., a bird, a fish, or a mammal such as a horse, cow, dog, monkey, mouse, pig, or rat. Preferably, the subject is a human. The method of treatment generally includes forming cement according to the method of forming cement described herein and then delivering the cement to the defective bone in the subject as part of a procedure for repairing the bone defect. Bone defects that can be treated using the method include defects due to osteoporosis, stress fracture, traumatic fracture, compression fracture, and combinations thereof. For example, the method of treatment described herein can be used to treat patients with a vertebral bone defect due to trauma or osteoporosis. The treatment can include using the cement product disclosed herein to form cement that is injected to the vertebra, for example, as part of a vertebroplasty or kyphoplasty procedure to stabilize the vertebra.

The bone cement product and methods described herein can also be used in oral or dental procedures that require the use of restorative cement. Such dental procedures can include generally includes forming cement according to the method of forming cement described herein and then delivering the cement to the oral or dental area of the subject that requires restoration, e.g., a tooth with a lesion or cavity.

The following examples further illustrate bone cement products and methods of forming cement according to the invention but, of course, should not be construed as in any way limiting its scope.

Example 1

The following describes the preparation of an acrylic resin-based paste-paste restorative cement product that includes a nano-hydroxyapatite bioactive component according to the invention. The cement product includes two parts. Part A is described in Table 2 and includes the polymerizable resin of the first component. Part B is described in Table 3 and includes the polyamine of the second component. Parts A and B were each formulated as a non-dripping paste-like shear thinning cream. The bioactive component was divided between Parts A and B.

TABLE 2

|  | (parts by weight) |
|---|---|
| Glycidyl dimethacrylate (GMA) (Sartomer SR379) | 58.74 |
| Ethoxylated (15) trimethylolpropanetriacrylate (Sartomer SR9035) | 5.30 |
| NanoHydroxyapatite (Angstrom Medica, Inc.) | 35.96 |

TABLE 3

|  | (parts by weight) |
|---|---|
| Polyethyleneimine (PEI-800) (Aldrich, Cat No.: 408719) | 55.0 |
| NanoHydroxyapatite (Angstrom Medica, Inc.) | 45.0 |

According to the manufacturer, PEI-800 polyethyleneimine has a branched polymer density of about 1.05 g/ml and average molecular weight of 800 Da. Both Part A and Part B had fast and excellent dispersion, they were highly formable, shapeable and easily delivered by a syringe delivery system. A cement product with a 4 to 1 ratio (by weight) of Part A to Part B was mixed on a watch glass pre-cooled to refrigerator temperature (0-5° C.). The cement mix was used to fill a ¼" i.d. hollow tubule to a height of 4 inches within 10 minutes. The filled tubule was placed into a 37° C. incubator. The cement mix was dried to touch after 5 to 10 minutes in the oven. The mix had no observable exotherm as determined by a thermocouple per ASTM F451-99.

The formed cement was released from the molding tubule and kept in the incubator oven for 3 days. The cement was compression tested with a MTI 10K compression tester (Measurements Technology, Inc., Roswell, Ga.) using a crosshead displacement rate of 1 mm/min. The specimen was tested according to ASTM C773 (ASTM International (West Conshohocken, Pa.)) (Procedure B) using test population 4 and compression modulus average 82.25 MPa. Maximum force average was 820 N, while the average peak stress was 21.32 MPa, and average strain 28.31%.

The foregoing example demonstrates that the cement product of the invention can be used in a method of forming cement that is injectable and has no observable rise in temperature.

Example 2

The following describes the preparation of another acrylic resin-based paste-paste restorative cement product with a bioactive component according to the invention. The bioactive component includes both nano-hydroxyapatite and nano-hydroxyapatite whiskers ranging in size from 5-10 nm in diameter to 250 nm in length. The cement product includes two parts. Part A is described in Table 4 and includes the polymerizable resin of the first component. Part B is described in Table 5 and includes the polyamine of the second component. Parts A and B were each formulated as a non-dripping paste-like shear thinning cream. The bioactive component was divided between Parts A and B.

TABLE 4

|  | (parts by weight) |
|---|---|
| Glycidyl dimethacrylate (GMA) (Sartomer SR379) | 69.10 |
| Ethoxylated (15) trimethylolpropanetriacrylate (Sartomer SR9035) | 3.78 |

TABLE 4-continued

|  | (parts by weight) |
| --- | --- |
| NanoHydroxyapatite whiskers (Angstrom Medica, Inc.) | 12.40 |
| NanoHydroxyapatite (Angstrom Medica, Inc.) | 14.72 |

TABLE 5

|  | (parts by weight) |
| --- | --- |
| PEI-800 (Polyethyleneimine, Aldrich Cat No.: 408719) | 55.0 |
| NanoHydroxyapatite (Angstrom Medica, Inc.) | 45.0 |

Both Parts A and Part B had fast and excellent dispersion, were highly formable, shapeable, and easily delivered by a syringe delivery system. A cement product with a 5.3 to 1 ratio (by weight) of Part A to Part B was mixed on a watch glass pre-cooled to refrigerator temperature (0-5° C.). The cement mix was used to fill a ¼" i.d. hollow tubule to a height of 4 inches within 10 minutes. The filled tubule was placed into a 37° C. incubator. The cement mix was dried to touch within 15 minutes in the oven. The mix had no observable exotherm as determined by a thermocouple per ASTM F451-99.

The formed cement was released from the molding tubule and kept in the incubator oven for 3 days. The cement was compression tested with a MTI 10K compression tester (Measurements Technology, Inc., Roswell, Ga.) using a crosshead displacement rate of 1 mm/min. The specimen was tested according to ASTM C773 (ASTM International) (Procedure B) using test population 3 and compression modulus average 29.45 MPa. Maximum force average was 284 N, while the average peak stress was 7.38 MPa, and average strain was 30.14%.

The foregoing example demonstrates another embodiment of the cement product of the invention that can be used in a method of forming cement that is injectable and has no observable rise in temperature.

Example 3

The following describes the preparation of an acrylic resin-based paste-paste restorative cement product with a bioactive component that includes nano-hydroxyapatite whiskers ranging in size from 5-10 nm in diameter to 250 nm in length. The cement product includes two parts. Part A is described in Table 6 and includes the polymerizable resin of the first component. Part B is described in Table 7 and includes the polyamine of the second component. Parts A and B were each formulated as a non-dripping paste-like shear thinning cream. The bioactive component was divided between Parts A and B.

TABLE 6

|  | (parts by weight) |
| --- | --- |
| Glycidyl dimethacrylate (GMA) (Sartomer SR379) | 70.0 |
| NanoHydroxyapatite whiskers (Angstrom Medica, Inc.) | 30.0 |

TABLE 7

|  | (parts by weight) |
| --- | --- |
| PEI-800 (Polyethyleneimine, Aldrich Cat No.: 408719) | 52.37 |
| NanoHydroxyapatite whiskers (Angstrom Medica, Inc) | 47.63 |

Both Parts A and Part B had fast and excellent dispersion, were highly formable, shapeable, and easily delivered by a syringe delivery system. A cement product with a 4 to 3 ratio (by weight) of Part A to Part B was mixed on a watch glass pre-cooled to refrigerator temperature (0-5° C.). The cement mix was used to fill a ¼" i.d. hollow tubule to a height of 1.25 inches within 15 minutes. The filled tubule was placed in a 37° C. incubator. The cement mix was dried to touch within 15 minutes in the oven. The mix had no observable exotherm as determined by a thermocouple per ASTM F451-99.

The formed cement was released from the molding tubule and kept in the incubator oven for 2 days. The cement was compression tested with a MTI 10K compression tester (Measurements Technology, Inc., Roswell, Ga.) using a crosshead displacement rate of 1 mm/min. The specimen was tested according to ASTM C773 (ASTM International) (Procedure B) using test population 1 and compression modulus average 47.4 MPa. Maximum force average was 626.8 N, while the average peak stress was 16.3 MPa, and average strain was 47.2%.

The foregoing example demonstrates another embodiment of the cement product of the invention that can be used in a method of forming cement that is injectable and has no observable rise in temperature.

Example 4

18.9631 grams of ethoxylated trimethylolpropanetriacrylate (SR9035, Sartomer) was added to 1.0380 grams of glycidyl methacrylate (SR379, Sartomer) to make the first component of the cement product. The first component was vortexed and mixed into a single phase. The second component of 0.3974 grams of PEI-800 (Aldrich, cat. no. 408719) was mixed with 2.7643 grams of the first component on a watch glass pre-cooled to 0-5° C. The mix was stirred at ambient temperature. The viscose fluid was transferred to a ¼" i.d. latex tubule with capped ends (3" long). The tubule was placed in a 37° C. incubator oven. The cement dried to touch within 15 minutes. The cement rod was released after 5 days and the released rod was in the incubator oven for an additional 7 days. The cement was compression tested with a MTI 1 OK compression tester (Measurements Technology, Inc., Roswell, Ga.) using a crosshead displacement rate of 1 mm/min. The specimen was tested according to ASTM C773 (ASTM International) (Procedure B) using test population 1 and compression modulus average 13.56 MPa. Maximum force average was 58.82 N, while the average peak stress was 2.08 MPa, and average strain was 16%.

The foregoing example demonstrates another embodiment of the cement product of the invention can be used in a method of forming cement that is injectable.

Example 5

A two component cement product was mixed to form cement. The first component comprising 0.7143 grams of glycidyl methacrylate (SR379, Sartomer) was added to the second component comprising 0.4713 grams of PEI-800

(Aldrich, cat. no. 408719). A white viscose fluid formed immediately with no temperature raise. The fluid was stirred well at ambient temperature and transferred to a ¼" i.d. latex tubule with capped ends (3" long). The tubule was placed in a 37° C. incubator oven. The cement dried to touch within 15 minutes. The cement rod was released after 5 days and the released rod was in the incubator oven for an additional 7 days. The cement rod was compression tested with a MTI 10K compression tester (Measurements Technology, Inc., Roswell, Ga.) using a crosshead displacement rate of 1 mm/min. The specimen was tested according to ASTM C773 (ASTM International) (Procedure B) using test population 1 and compression modulus average 13.56 MPa. Maximum force average was 58.82 N, while the average peak stress was 2.08 MPa, and average strain was 16%.

The foregoing example demonstrates another embodiment of the cement product of the invention that can be used in a method of forming cement that is injectable.

Example 6

This example compares the exothermic profile of various embodiments of the cement product according to the invention, each embodiment having different relative amounts of the first and second component.

The relative amounts of the first component, comprising GMA, and the second component, comprising PEI, were varied as indicated in Table 8. Table 8 also indicates (a) predicted millimoles of double bonds (C=C) in the glycidyl groups of the GMA (assuming 100% purity and GMA monomeric molecular weight of 142.15 daltons), (b) millimoles of PEI repeat units (assuming 100% purity and repeat unit molecular weight of 43.07 daltons), (c) equivalent ratio of GMA glycidyl groups to PEI repeat units, (d) the observed temperature rise after mixing for two minutes, and (e) setting time in a 37° C. incubator oven after N2 gas purging.

TABLE 8

| | Cement Product | | | | | |
|---|---|---|---|---|---|---|
| | 6-A | 6-B | 6-C | 6-D | 6-E | 6-F |
| GMA (grams) | 0.7169 | 1.4287 | 1.1222 | 0.6841 | 0.6425 | 0.7361 |
| Glycidyl (C=C) mmole | 5 | 10.05 | 7.89 | 4.8 | 4.5 | 5.17 |
| PEI (grams) | 0.4387 | 0.6770 | 0.4307 | 0.5444 | 0.6066 | 0.7356 |
| PEI mmole | 10.18 | 15.7 | 10.00 | 12.64 | 14.08 | 17.08 |
| GMA:PEI mmole ratio | 0.49:1 | 0.64:1 | 0.79:1 | 0.38:1 | 0.32:1 | 0.30:1 |
| Temperature rise (° C.) | 27-29 | 27-29 | 27-28 | 27-29 | 25-28 | 25-28 |
| Set time (min.) | 35 | 135 | 135 | 35 | 38 | 35 |

The results in Table 8 indicate that when GMA is in excess, the polymer system is more sluggish in curing. On the other hand, when the stoichiometric ratio of reacting functional groups are equal, or when PEI is in excess, more rapid curing is achieved.

A clear tubule shaped sample of formed cement product 6-A (0.49:1 mole ratio of GMA:PEI) showed maximum compression strain of 81.2%, peak stress of 48.5 MPa, and compression module of 154.84 MPa. Upon release of the strain, the sample returned to its original length within a few seconds. However, this aliphatic neat polymer system is not hydrolysis resistant.

The results are consistent with the following polymerization model. When PEI equivalents are in excess, Michael addition reactions (of C=C double bonds and the primary and secondary amine groups in the PEI) are dominant and there is less dampening of exothermic temperature rise, since there are not enough endothermic reactions available to compensate for the exothermic glycidyl-amine reaction. When excess PEI is reduced and there are nearly equal amounts of PEI repeat equivalents as C=C double bond equivalents, or when there is a slight molar excess of C=C double bond groups (e.g., a slight excess of GMA) the system can begin to favor the endothermic reactions that dampen the exothermic temperature rise. This model suggests that adding a vinyl or allyl component in addition to the first GMA component can supply additional double bonds, which are used not only for Michael addition to amines on PEI but also for carbocation reaction sites. In other words, vinyl oligomers such as (bis-GMA) or other vinyl oligomers described herein may be added as an additional polymerizable resin to the first and second components of the cement product. It should be noted, however, that too much excess GMA can result in a slower set time.

Example 7

The following describes the preparation of another acrylic resin-based paste-paste restorative cement product with a bioactive component according to the invention. The bioactive component includes Spectrum Chemicals poorly crystallized calcium phosphate tribasic (Catalog # C1155) dense powder. The cement product includes two parts. Part A is described in Table 9 and includes the polymerizable resin of the first component. Part B is described in Table 10 and includes the polyamine of the second component. Parts A and B were each formulated as a non-dripping paste-like thick ointment. The bioactive component was divided between Parts A and B.

TABLE 9

| | (parts by weight) |
|---|---|
| Ethoxylated(2) Bisphenol A Diacrylate (SPP M-193) | 58.48 |
| Calcium Phosphate Tribasic (Spectrum Chemical C1155) | 41.52 |

TABLE 10

| | (parts by weight) |
|---|---|
| PEI-800 (Polyethyleneimine, Aldrich Cat No.: 408719) | 42.44 |
| Calcium Phosphate Tribasic (Spectrum Chemical C1155) | 57.56 |

Both Parts A and Part B were thick ointment-like pastes. A cement product with a 2.1 to 1 ratio (by weight) of Part A to Part B was mixed on a watch glass. The cement mix was used to fill a ¼" i.d. hollow tubule to a height of 6 inches within 3 minutes. The cement mix was dried to touch within 3 minutes at room temperature. The mix had exotherm temperature raise of 6° C./min as determined by thermocouple per ASTM F451-99.

The formed cement was released from the molding tubule and kept at room temperature for 16 days. The cement was compression tested with a MTI 10K compression tester (Measurements Technology, Inc., Roswell, Ga.) using a crosshead displacement rate of 10 mm/min. The specimen was tested according to ASTM C773 (ASTM International) (Procedure B) using test population 3 and compression modulus average 176 MPa. Maximum force average was 1357 N, while the average peak stress was 40.8 MPa and average strain was 30.72%.

Example 8

The following describes the preparation of another acrylic resin-based paste-paste restorative cement product without a bioactive component according to the invention. The neat polymeric resin product includes part A and part B as described in Table 11. Parts A and B were each formulated as a liquid resin.

TABLE 11

|  | (parts by weight) |
| --- | --- |
| A: Ethoxylated(2) Bisphenol A Diacrylate (SPP M-193) | 82.9 |
| B: PEI-800 (Polyethyleneimine, Aldrich Cat No.: 408719) | 17.1 |

Both Parts A and Part B were free flowing low viscosity liquid. A thermoset product with a 4.85 to 1 ratio (by weight) and 1 to 1 by mole of Part A to Part B was mixed on a watch glass. The cement mix was used to fill a ¼" i.d. hollow tubule to a height of 6 inches within 5 minutes. The cement mix was dried to touch within 15 minutes in an incubator oven. The mix had little exotherm temperature rise as determined by thermocouple per ASTM F451-99.

The formed thermoset solid tube was released from the molding tubule and kept in the incubator oven for 14 days. The thermoset was compression tested with a MTI 10K compression tester (Measurements Technology, Inc., Roswell, Ga.) using a crosshead displacement rate of 10 mm/min. The specimen was tested according to ASTM C773 (ASTM International) (Procedure B) using test population 5 and compression modulus average 30 MPa. Maximum force average was 2376 N, while the average peak stress was 75 MPa and average strain was 50.28%. The solid tube is compressible and recovered to its original length after the stress was released.

Example 9

The following describes the preparation of another acrylic resin-based paste-paste restorative cement product without a bioactive component according to the invention. The neat polymeric resin product includes part A and part B as described in Table 12. Parts A and B were each formulated as a liquid resin.

TABLE 12

|  | (parts by weight) |
| --- | --- |
| A: Ethoxylated(2) Bisphenol A Diacrylate (SPP M-193) | 75.85 |
| B: PEI-800 (Polyethyleneimine, Aldrich Cat No.: 408719) | 24.15 |

Both Parts A and Part B were free flowing low viscosity liquid. A thermoset product with a 3 to 1 ratio (by weight) and 1 to 1.6 by mole of Part A to Part B was mixed on a watch glass. The cement mix was used to fill a ¼" i.d. hollow tubule to a height of 6 inches within 8 minutes. The cement mix was dried to touch within 25 minutes in an incubator oven. The mix had little exotherm temperature rise as determined by a thermocouple per ASTM F451-99.

The formed thermoset solid tube was released from the molding tubule and kept in the incubator oven for 14 days. The thermoset was compression tested with a MTI 10K compression tester (Measurements Technology, Inc., Roswell, Ga.) using a crosshead displacement rate of 10 mm/min. The specimen was tested according to ASTM C773 (ASTM International) (Procedure B) using test population 5 and compression modulus average 76.53 MPa. Maximum force average was 650 N, while the average peak stress was 20.33 MPa and average strain was 50.91%. The solid tube is compressible and recovered to its original length after stress was released.

Example 10

The following describes the preparation of another acrylic resin-based paste-paste restorative cement product without a bioactive component according to the invention. The neat polymeric resin product includes two parts. Part A and part B are described in Table 13. Parts A and B were each formulated as a liquid resin.

TABLE 13

|  | (parts by weight) |
| --- | --- |
| A: BisGMA (Sartomer CN151) | 85.66 |
| B: PEI-800 (Polyethyleneimine, Aldrich Cat No.: 408719) | 14.34 |

Parts A is a sticky high viscosity fluid and was heated to 37° C. to lower its viscosity and Part B is a free flowing low viscosity liquid. A thermoset product with a 4 to 1 ratio (by weight) and 1 to 1 by mole of Part A to Part B was mixed on a watch glass The cement mix was used to fill a ¼" i.d. hollow tubule to a height of 8 inches within 20 minutes. The thermoset mix was sticky and the hollow tubule was end-capped with a stop-cork plug then it was placed in a 37 C incubator oven. The mix had little exotherm temperature rise as determined by thermocouple per ASTM F451-99.

It was left to harden overnight. The formed thermoset solid tube was kept in the incubator oven for 10 days. Then the hollow tubule was removed. The thermoset was compression tested with a MTI 10K compression tester (Measurements Technology, Inc., Roswell, Ga.) using a crosshead displacement rate of 10 mm/min. The specimen was tested according to ASTM C773 (ASTM International) (Procedure B) using test population 4 and maximum compression modulus was 434 MPa. Maximum force was 4287 N, while the maximum peak stress was 111 MPa, and maximum strain was 70%. The solid tube is compressible and recovered to its original length after stress was released.

The foregoing example demonstrates that the cement product of the invention can be used in a method of forming cement that is injectable and is only mildly exothermic. The foregoing example also indicates that the ratio of first and second components in the cement product of the invention can be adjusted to further reduce the exothermic rise in temperature produced by mixing the components of the cement product.

Example 11

The following describes experiments performed to determine the temperature rise and set times that result from varying the type and/or amount of a first or second component in a cement product of the invention.

Figure 2:
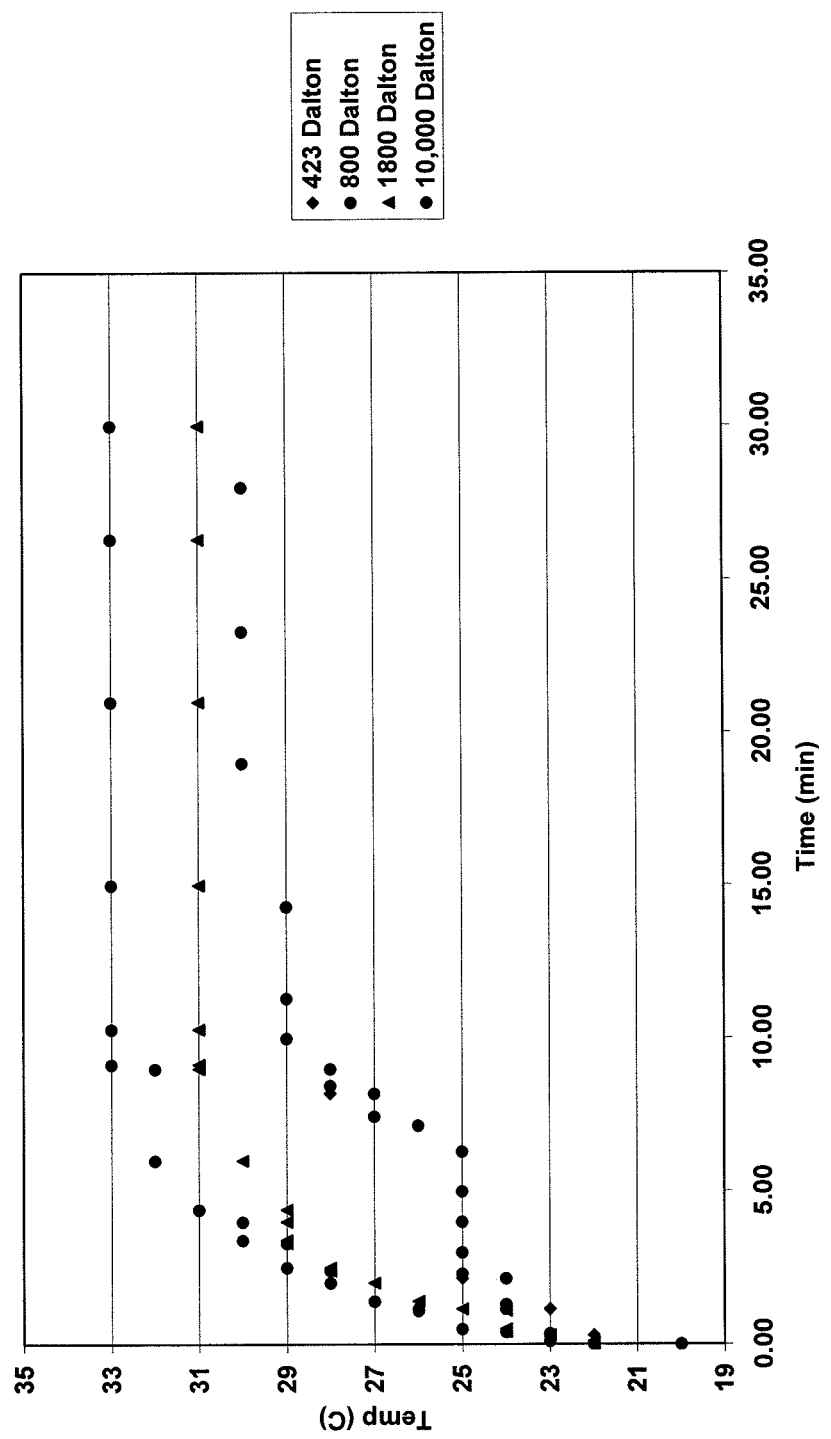
FIG. 2 is a graph showing temperature rise relative to time for compositions of the invention that include indicated molecular weights of PEI.
Figure 3:
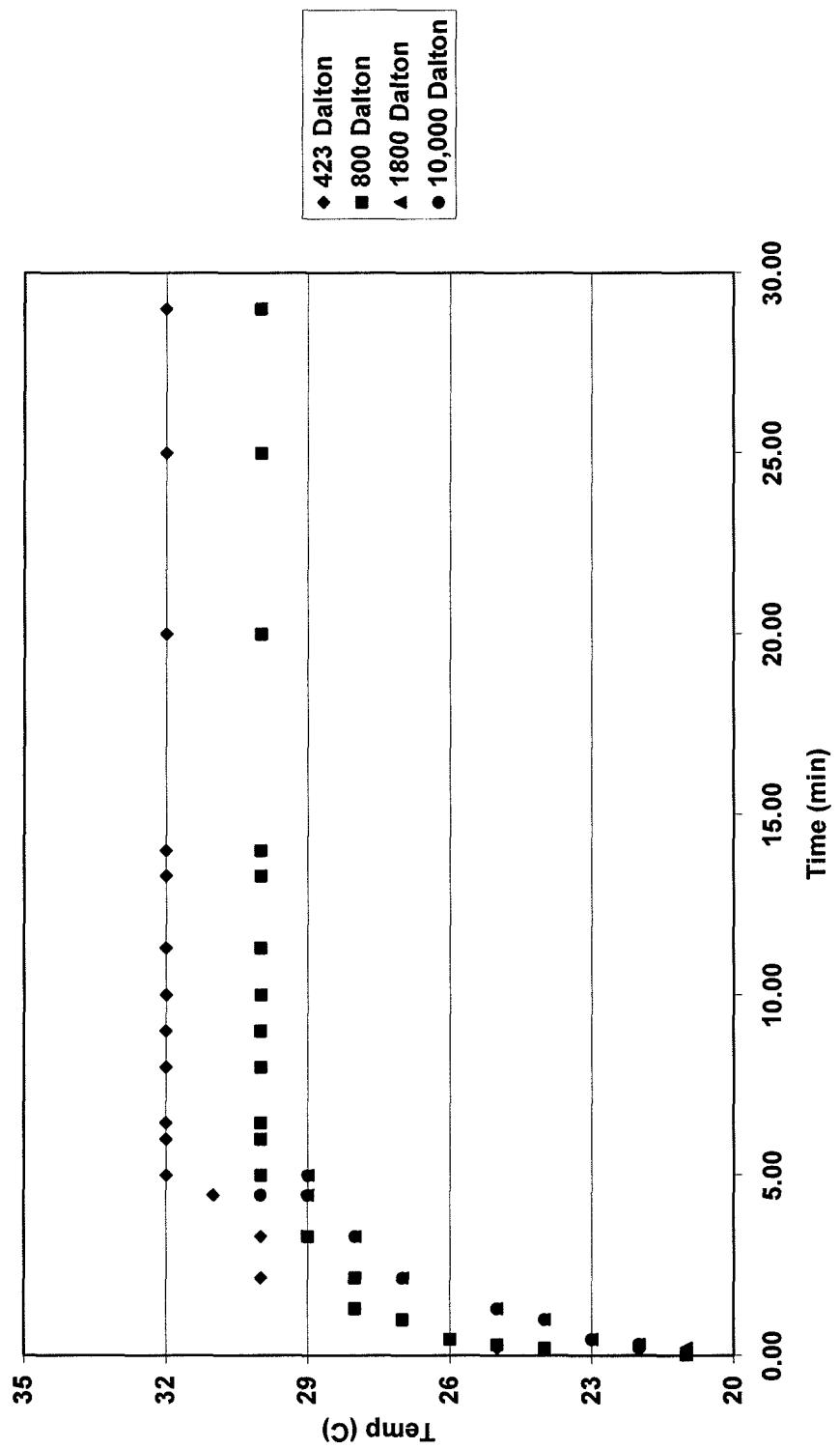
FIG. 3 is a graph showing temperature rise relative to time for compositions of the invention that include indicated molecular weights of PEI.

In a first set of three experiments, SR9035 was mixed with one of the following four grades of PEI, linear PEI with average molecular weight of 423 daltons (PEI-423), branched PEI with average molecular weight of 800 daltons (PEI-800), PEI with average molecular weight of 1800 daltons (PEI-1800), or PEI with average molecular weight of 10,000 daltons (PEI 10,000). Individual mixtures included a mole ratio of 0.8:1, 1:1, or 1.2:1 of SR9035 to each grade of PEI. The results depicted in FIGS. 1, 2 and 3 show a similar temperature rise for each mixture. Maximum temperature rises were all well below body temperatures.

PEI-10000 did not set overnight any of the three tested ratios, while PEI-1800 set only at the excess ratio of 1.2:1 overnight. PEI-800 and PEI-423 set within 5 to 15 minutes and hardened 30 minutes after mixing for all 3 mole ratios.

The foregoing example demonstrates a stoichiometry tolerance of at least +/−20% for achieving reasonably quick set and hardening times for cements including PEI-800 and PEI 423. The results also indicates that the concentration of primary amine in PEI's is a determining factor of the set time, since PEI-10,000 and PEI-1800 have a much lower concentration of primary amine (chain-ends) than PEI-800 or PEI-423.

Example 12

The following describes experiments performed to determine the temperature rise and set times that result from varying the type and/or amount of a first or second component in a cement product of the invention.

Experiments were performed under a cold visible 13 watt OTT-LITE lamp. Mixed reaction components were formed into a dough at room temperature and then placed in an incubator oven at 37.5+/−1° C. Reactions stopped when the dough hardened. In each reaction the second component was PEI-800. PEI-800 was reacted with (a) non-alkoxylated pentaerythritol triacrylate (PETA) at a PEI to triacrylate mole ratio of 0.6:1, 0.8:1, 1:1 or 1.2:1, (b) propoxylated (3) trimethylolpropane triacrylate (TMPTA) at a PEI to triacrylate mole ratio of 0.6:1, 0.8:1, 1:1 or 1.2:1, or (c) propoxylated(5) glycerol ethoxylated bisphenol-A-triacrylate at a PEI to triacrylate mole ratio of 1:1 or 1.2:1. Exotherm temperature rises over time are shown in FIGS. 4, 5, and 6.

PEI-800 to non-alkoxylated PETA mole ratios of 1.2:1 and 1:1 generated rapid temperature rises up to 50° C. The PETA reaction set and was very hard within 2 minutes, making it the fastest of the triacrylates with a commendable temperature rise.

Figure 4:
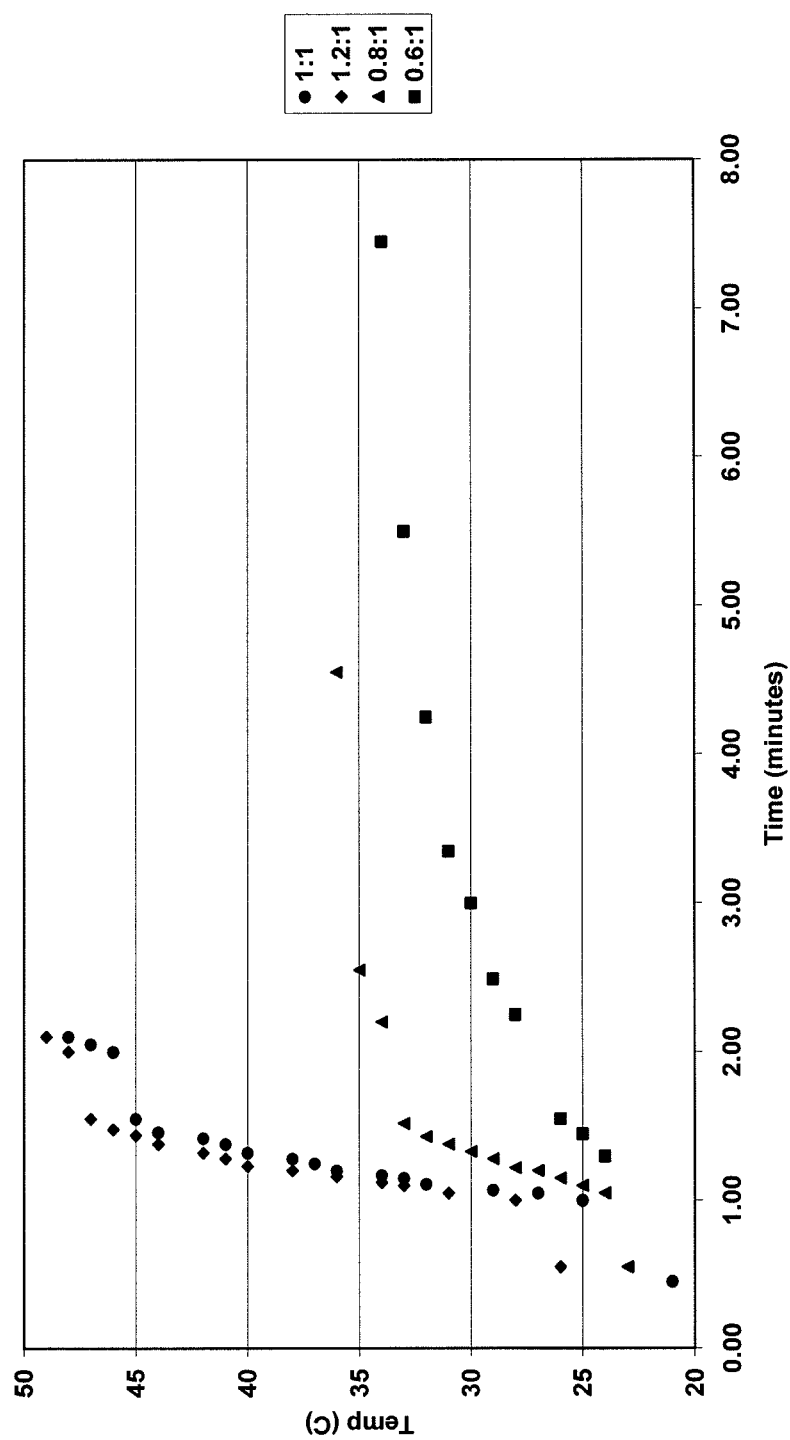
FIG. 4 is a graph showing temperature rise relative to time for compositions of the invention that include the indicated mole ratios of PEI to pentaerythritol triacrylate.
Figure 5:
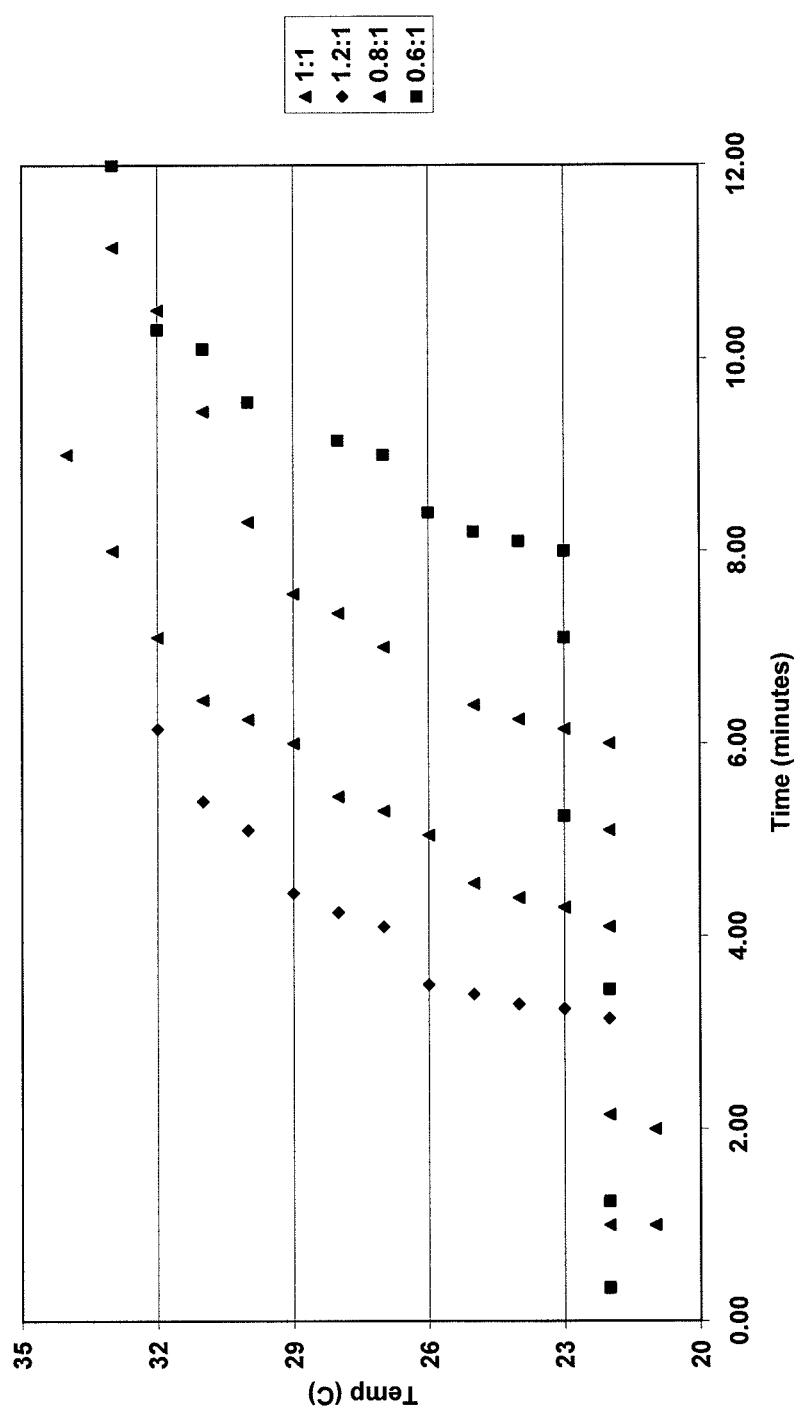
FIG. 5 is a graph showing temperature rise relative to time for compositions of the invention that include indicated mole ratios of PEI to propoxylated (3) TMPTA.
Figure 6:
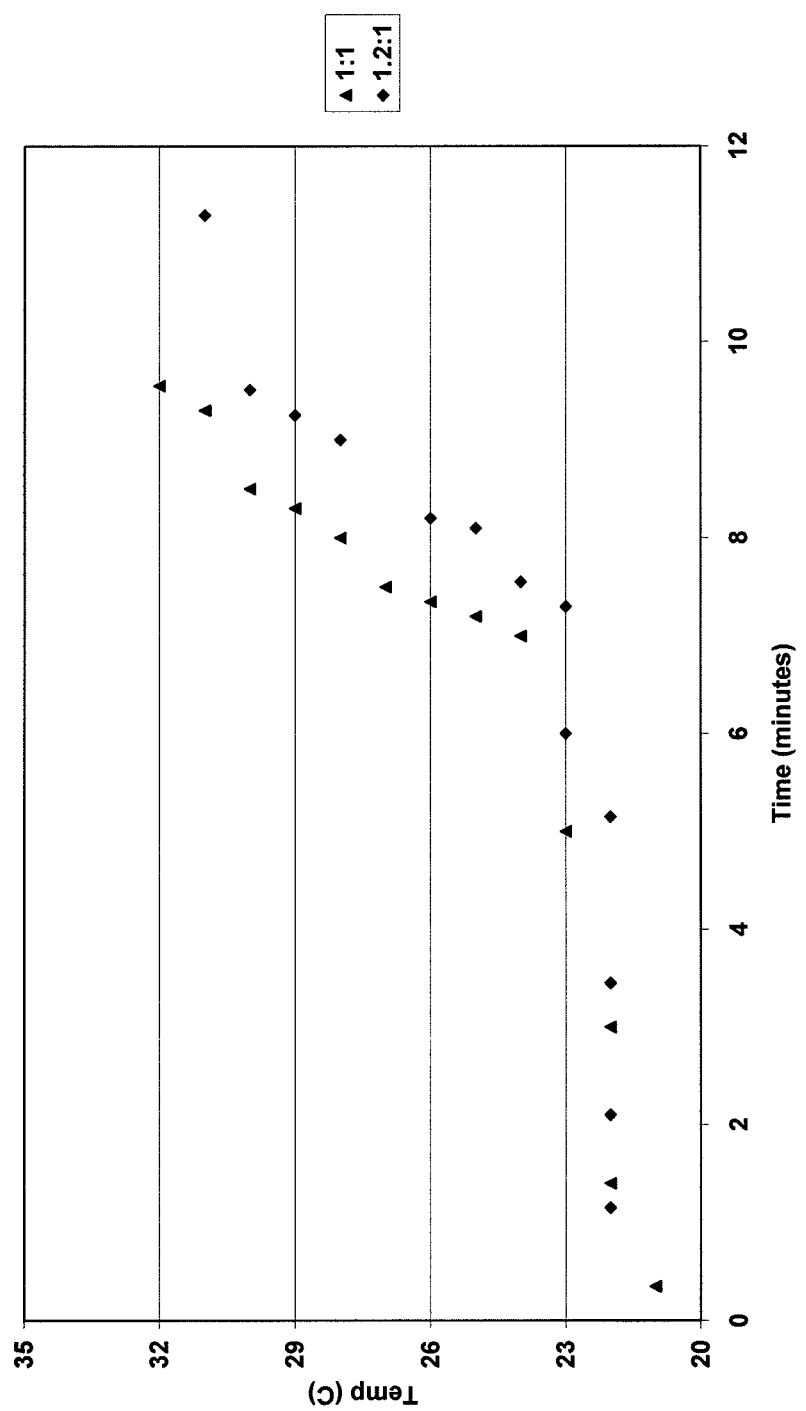
FIG. 6 is a graph showing temperature rise relative to time for compositions of the invention that include indicated mole ratios of PEI to propoxylated (5) glycerol ethoxylated bisphenol-A-triacrylate.

Results shown in FIGS. 4, 5, and 6 of the foregoing example indicates that when PEI is stoichiometric or slightly in excess, the triacrylates set faster and, when PEI is deficient, the set reactions are more sluggish. Results shown in FIGS. 4, 5, and 6 also indicate that the more extensively alkoxylated the triacrylates, the slower the set time and the lower the temperature rise. Thus, degree of alkoxylation affects set time as well as exotherm temperature rises. Additionally, the example indicates that propylene glycol moieties in the oligomer can act as (i) a solvent that dilutes PETA and (ii) a heat sink to help lower the exotherm heat.

Example 13

The following example describes experiments performed to determine the temperature rise and set times associated with cement products of the invention formed by mixing various ratios of a first component and a second component that further includes a low dose of 222 ppm camphorquinone (CQ) photoinitiator.

Reaction conditions were the same as those described for Example 12, except that 222 ppm of CQ photoinitiator was dissolved into PEI-800. CQ-doped PEI-800 was reacted with (a) PETA at a PEI to triacrylate mole ratio of 0.6:1, 0.8:1, 1:1 or 1.2:1, (b) propoxylated (3) TMPTA at a PEI to triacrylate mole ratio of 0.6:1, 0.8:1, 1:1 or 1.2:1, or (c) propoxylated(5) glycerol ethoxylated bisphenol-A-triacrylate at a PEI to triacrylate ratios of 1:1. Results are shown in FIGS. 7, 8, and 9.

Figure 7:
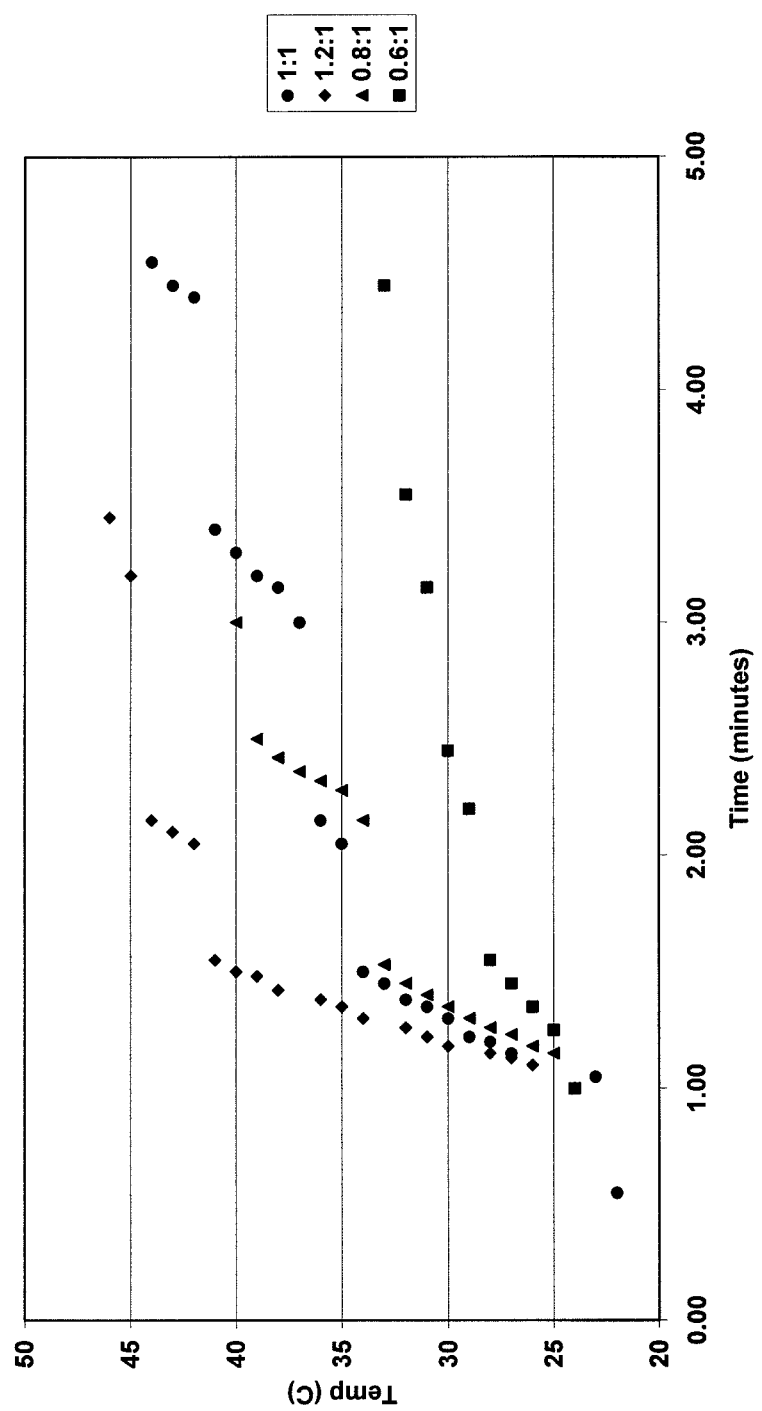
FIG. 7 is a graph showing temperature rise relative to time for compositions of the invention that include the indicated mole ratios of PEI (doped with CQ 222 pm) to pentaerythritol triacrylate.
Figure 8:
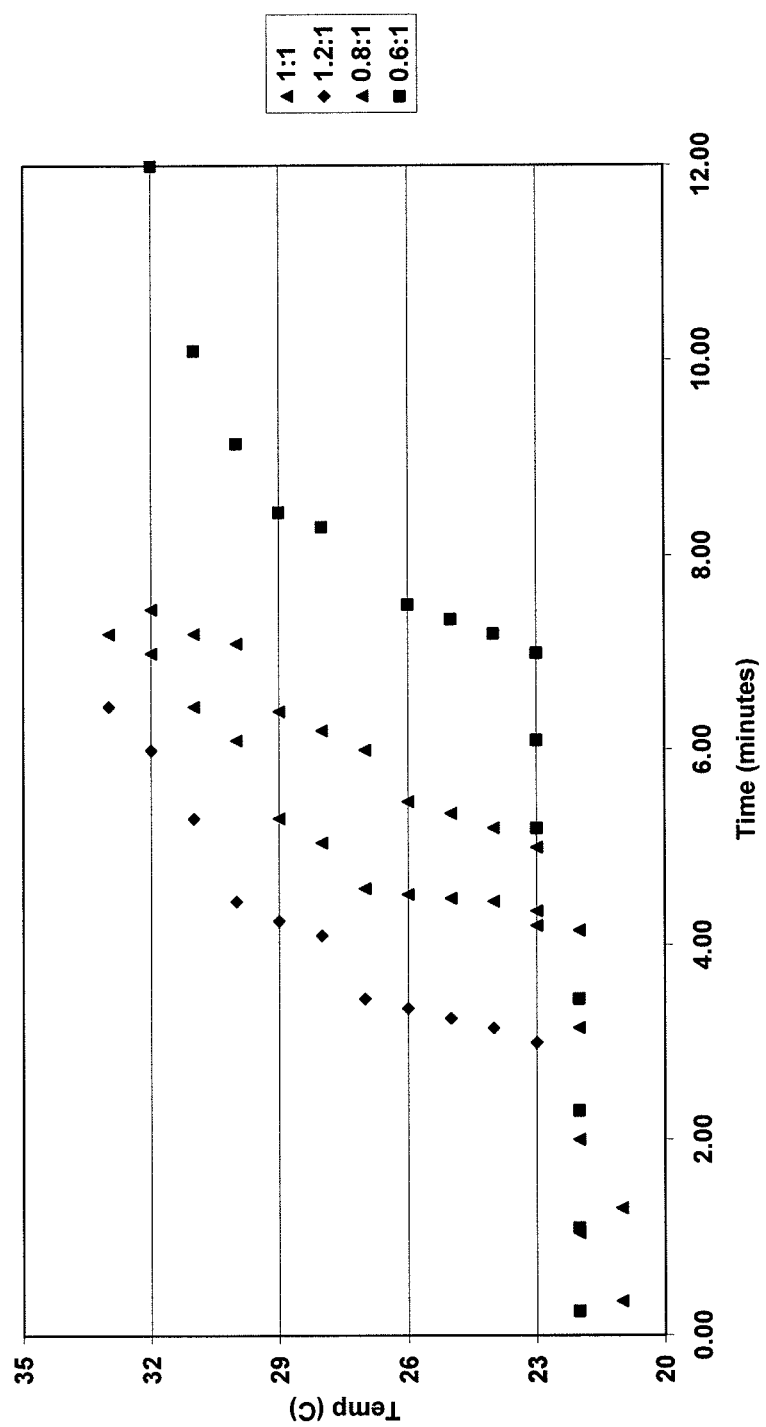
FIG. 8 is a graph showing temperature rise relative to time for compositions of the invention that include the indicated mole ratios of PEI (doped with CQ 222 pm) to propoxylated (3) TMPTA.
Figure 9:
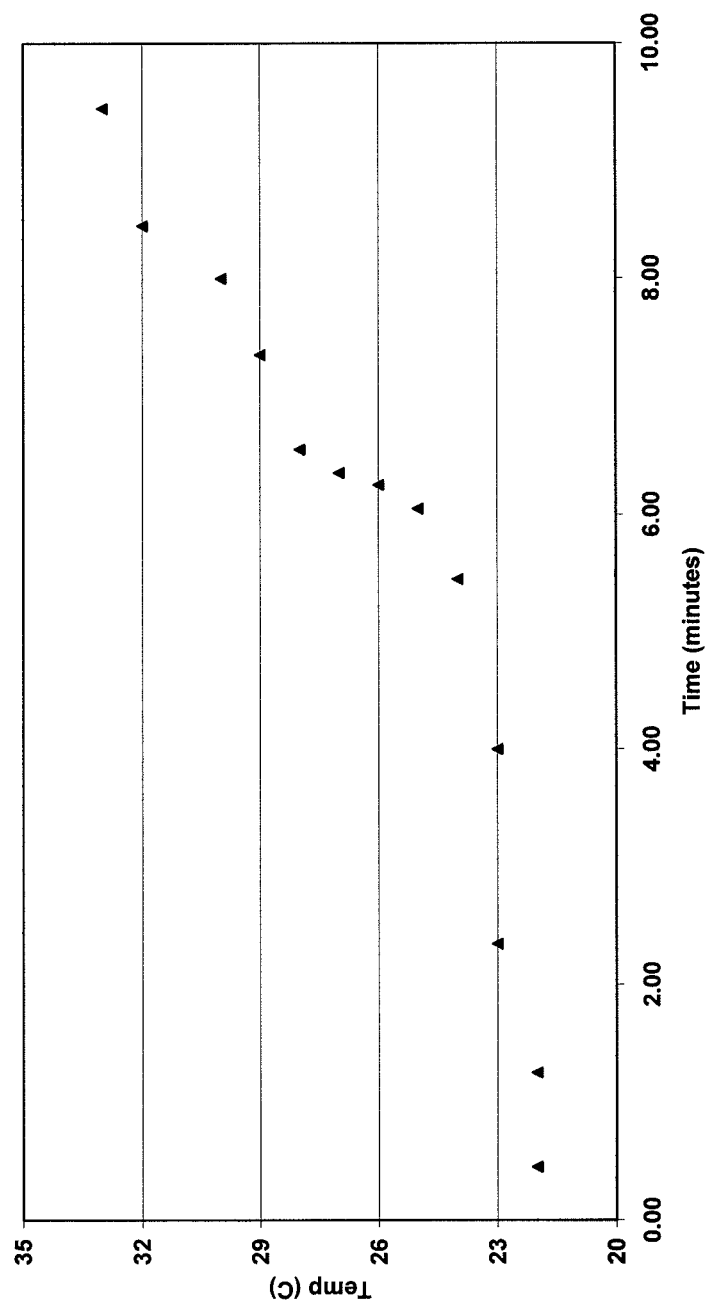
FIG. 9 is a graph showing temperature rise relative to time for compositions of the invention that include the 1:1 mole ratio of PEI (doped with CQ 222 pm) to propoxylated (5) glycerol ethoxylated bisphenol-A-triacrylate.

The results depicted in FIGS. 7, 8, and 9 of the foregoing example indicate that (i) when PEI is in slight excess, the triacrylates set faster, (ii) when PEI is deficient, set reactions are more sluggish (iii) increased alkoxylation of triacrylates slows down set time and lowers exotherm temperature, and (iv) propylene glycol moieties in the oligomers can act as (a) a solvent that dilutes PETA and (b) a heat sink to help lower the exotherm heat. Again, PETA by far is clearly the fastest setting of the triacrylates and exhibits a commendable temperature rise. The foregoing example also indicates that the low dose of CQ photoinitiator has little or no effect at 0.6:1 PEI:triacrylate ratios, which suggests that excess triacrylates engaged in little or no free radical polymerization. However, the results depicted in FIG. 7 indicate that low dose CQ photoinitiator did produce a faster initial temperature rise in the 0.8:1 mole ratio PEI/PETA system, such that the 0.8:1 mole ratio system eventually matches the temperature rise of the 1:1 system.

Example 14

The following example describes experiments performed to determine the temperature rise and set times associated with cement products of the invention formed by mixing various ratios of a first component and a second component that further includes 0.5% CQ photoinitiator.

Reaction conditions were the same as those described for Example 13, except that CQ photoinitiator was dissolved in PEI-800 to 0.5% by weight. CQ-doped PEI-800 was mixed with (a) PETA, (b) propoxylated (3) TMPTA, (c) propoxylated(5) glycerol ethoxylated bisphenol-A-triacrylate, or propoxylated (6) TMPTA. Each mixture included a PEI to triacrylate mole ratio of 0.6:1, 0.8:1, 1:1 or 1.2:1. Results are shown in FIGS. 10, 11, 12, 13

The results shown in FIGS. 10, 11, 12, and 13 of the example indicate that (i) when PEI is in slight excess, the triacrylates set faster, (ii) when PEI is deficient, set reactions are more sluggish (iii) increased alkoxylation of triacrylates slows down set time and lowers exotherm temperature, and (iv) PETA is clearly the fastest setting of the triacrylates and exhibits a commendable temperature rise.

Figure 10:
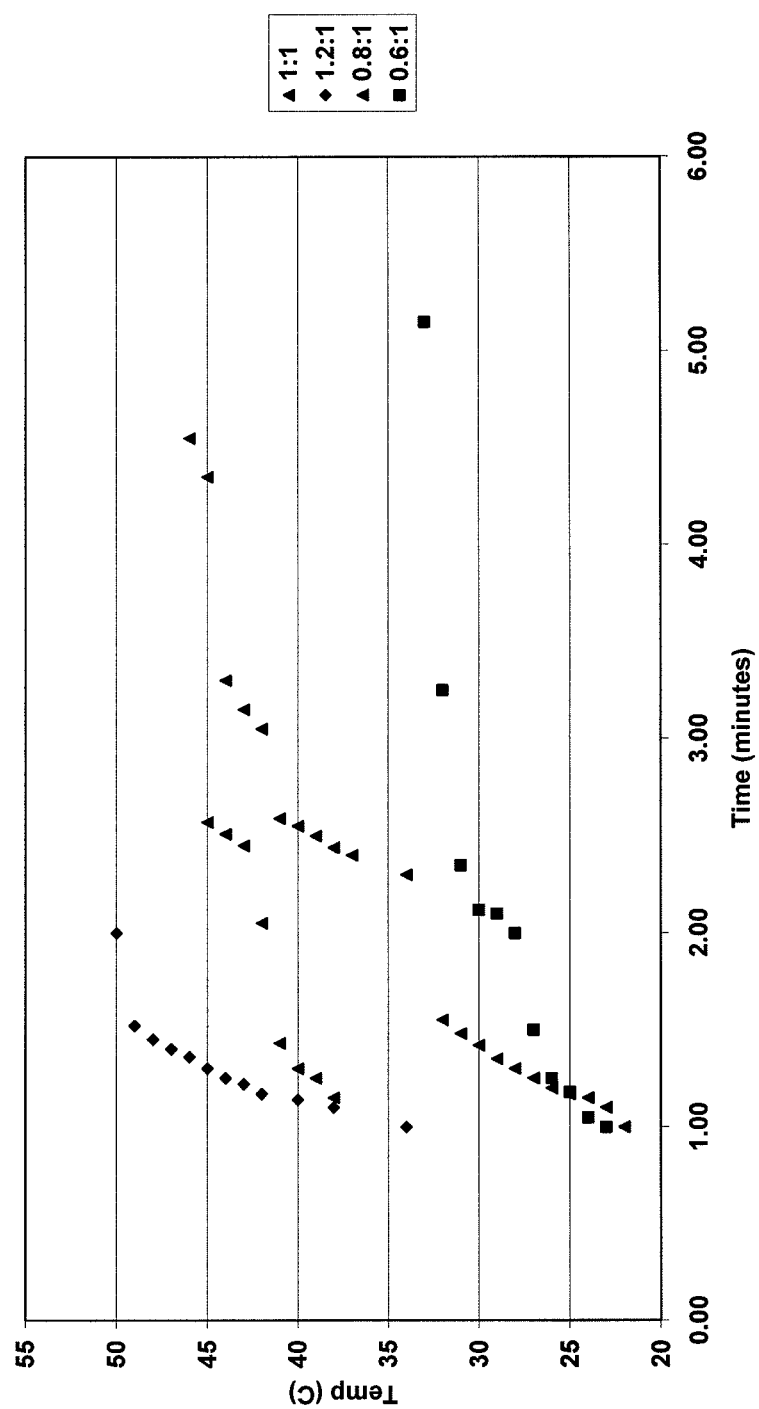
FIG. 10 is a graph showing temperature rise relative to time for compositions of the invention that include the indicated mole ratios of PEI (doped with CQ 0.5%) to pentaerythritol triacrylate.
Figure 11:
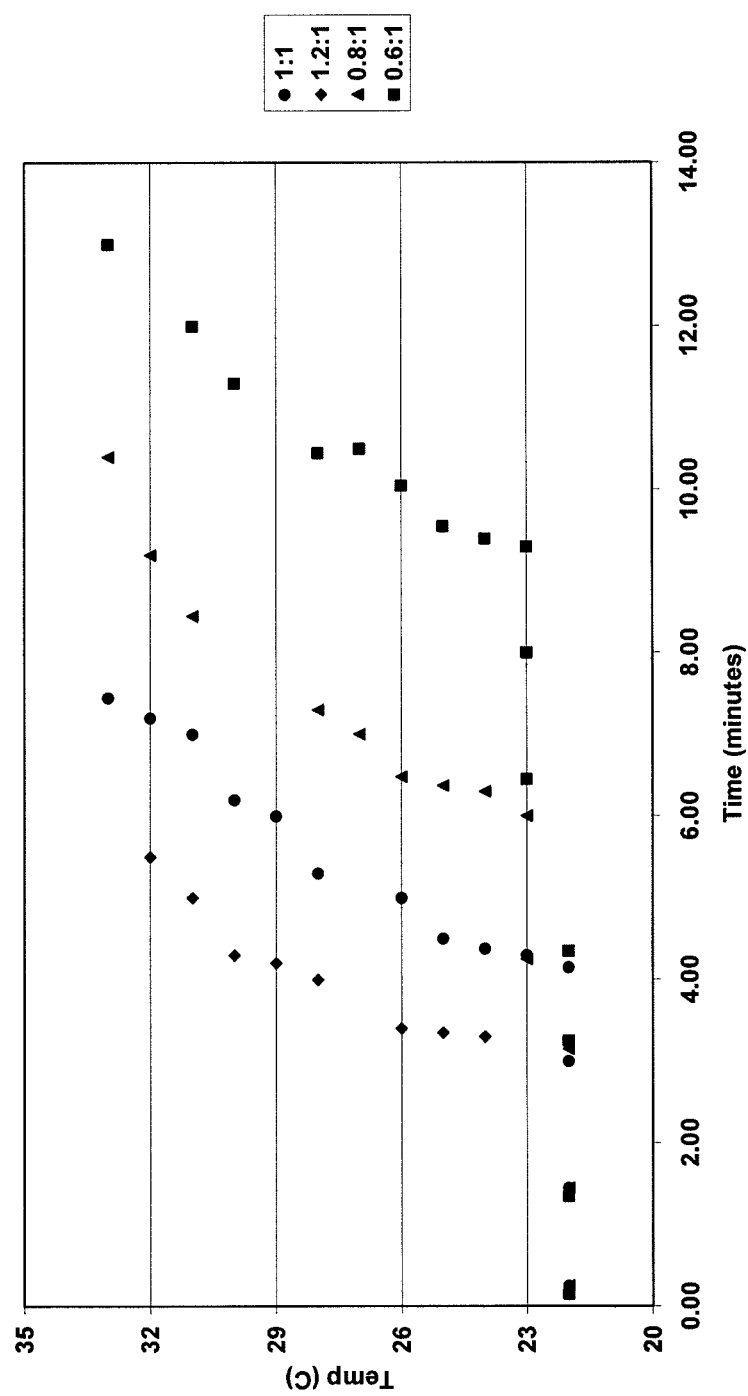
FIG. 11 is a graph showing temperature rise relative to time for compositions of the invention that include the indicated mole ratios of PEI (doped with CQ 0.5%) to propoxylated (3) TMPTA.
Figure 12:
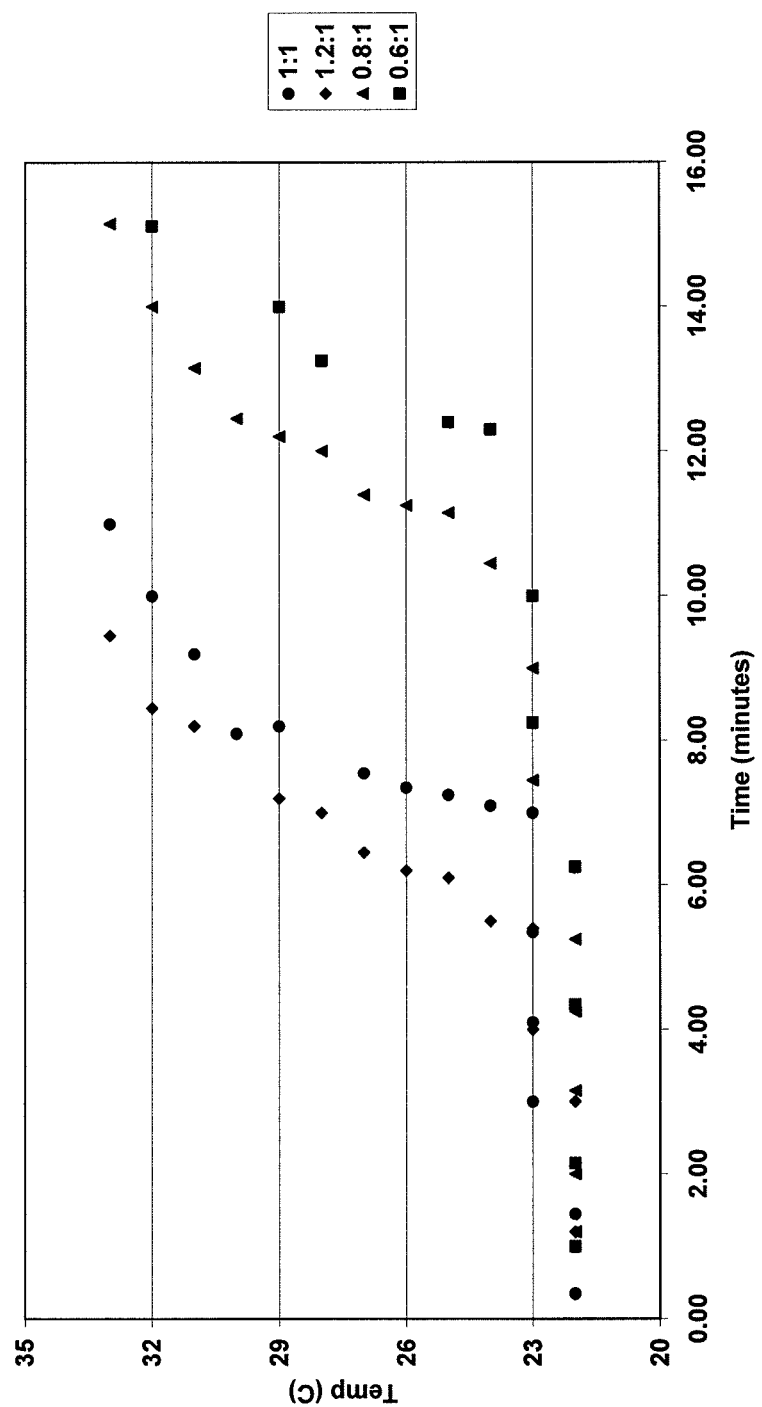
FIG. 12 is a graph showing temperature rise relative to time for compositions of the invention that include the indicated mole ratios of PEI (doped with CQ 0.5%) to propoxylated (5) glycerol ethoxylated bisphenol-A-triacrylate.
Figure 13:
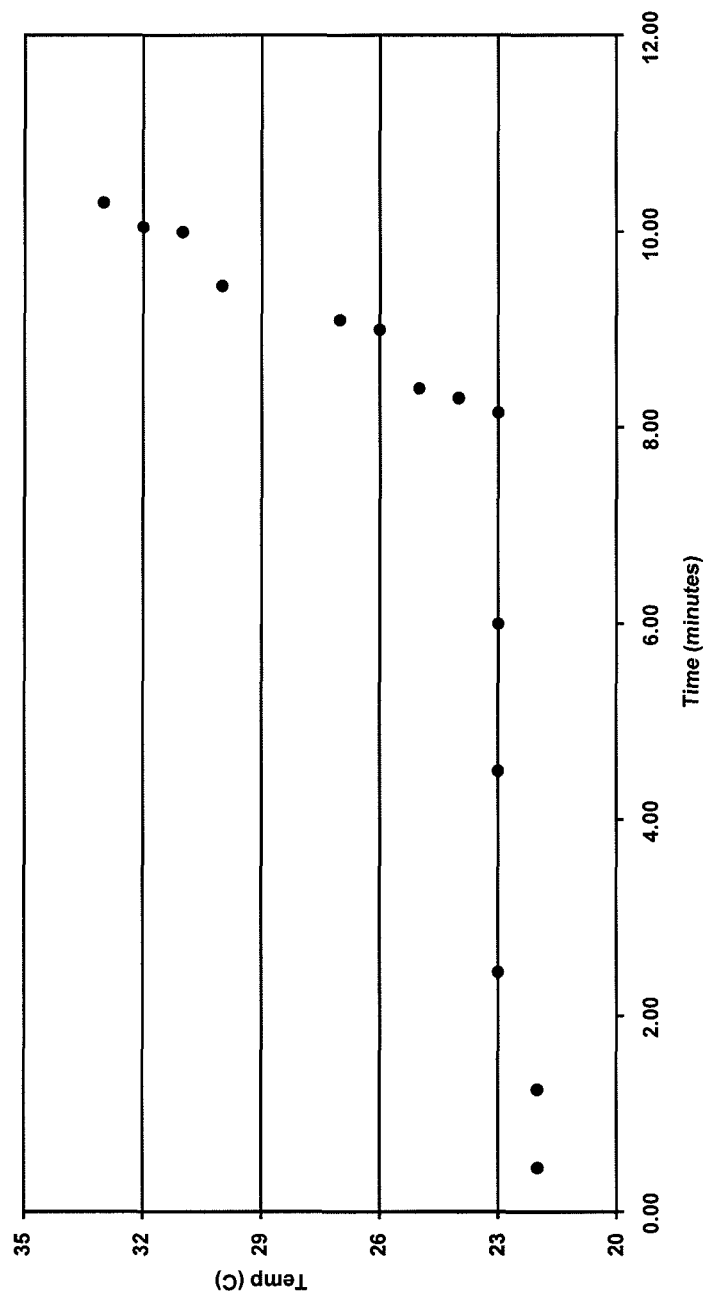
FIG. 13 is a graph showing temperature rise relative to time for compositions of the invention that include a 1:1 mole ratio of PEI (doped with CQ 0.5%) to propoxylated (6) TMPTA.
Figure 14:
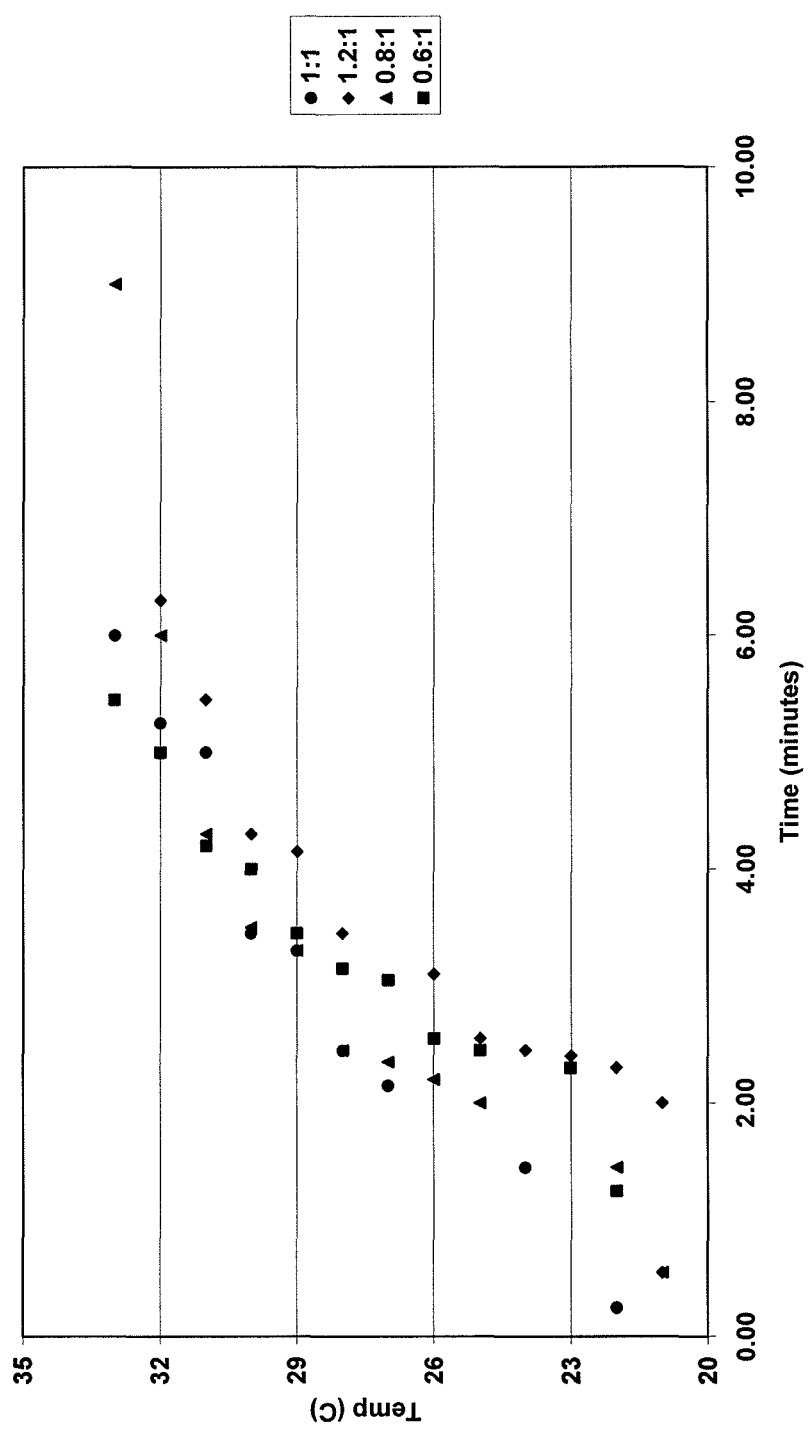
FIG. 14 is a graph showing temperature rise relative to time for compositions of the invention that include the indicated mole ratios of PEI to ethoxylated (2) bisphenol-A-diacrylate.
Figure 15:
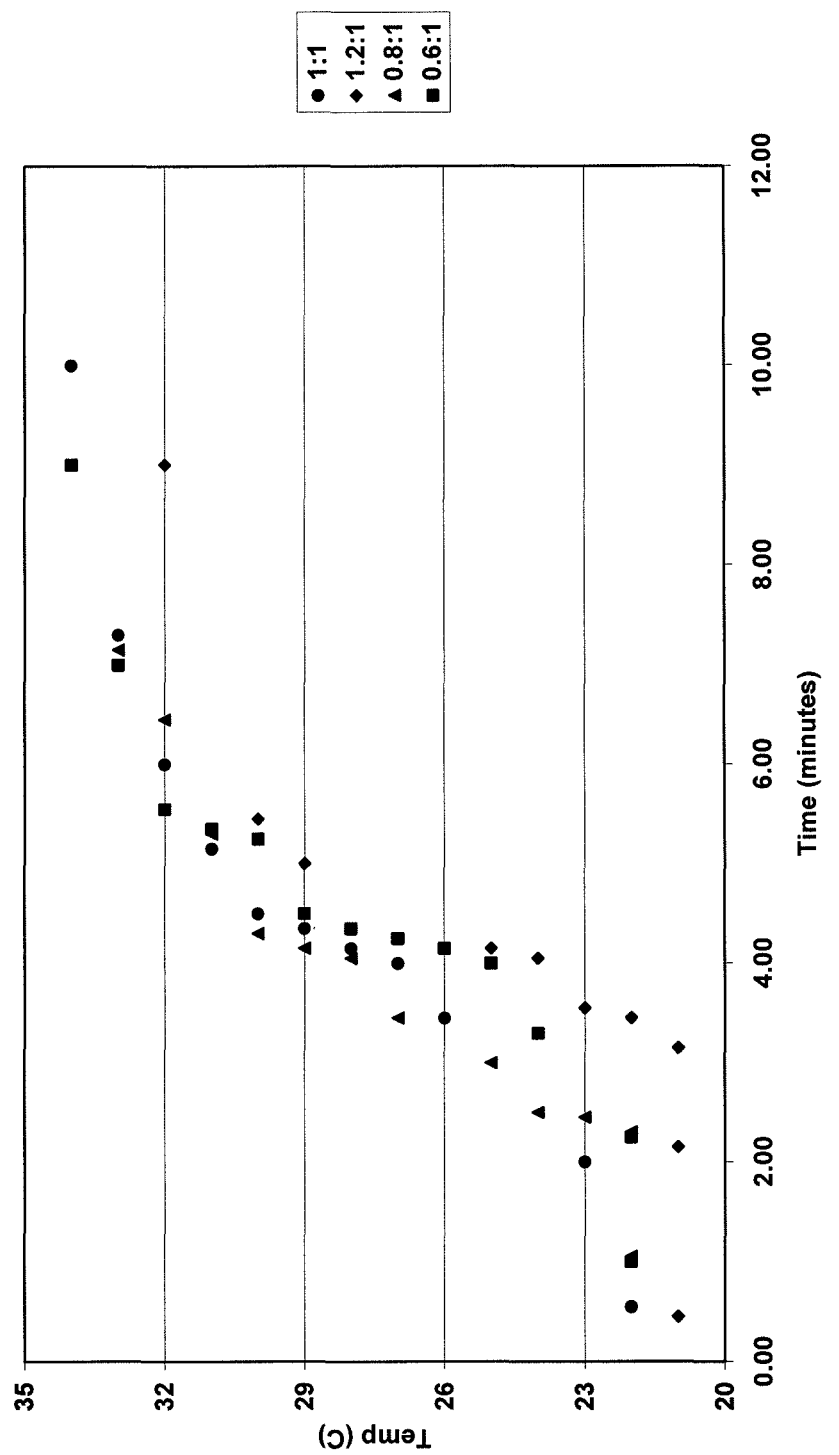
FIG. 15 is a graph showing temperature rise relative to time for compositions of the invention that include the indicated mole ratios of PEI to ethoxylated (4) bisphenol-A-diacrylate.
Figure 16:
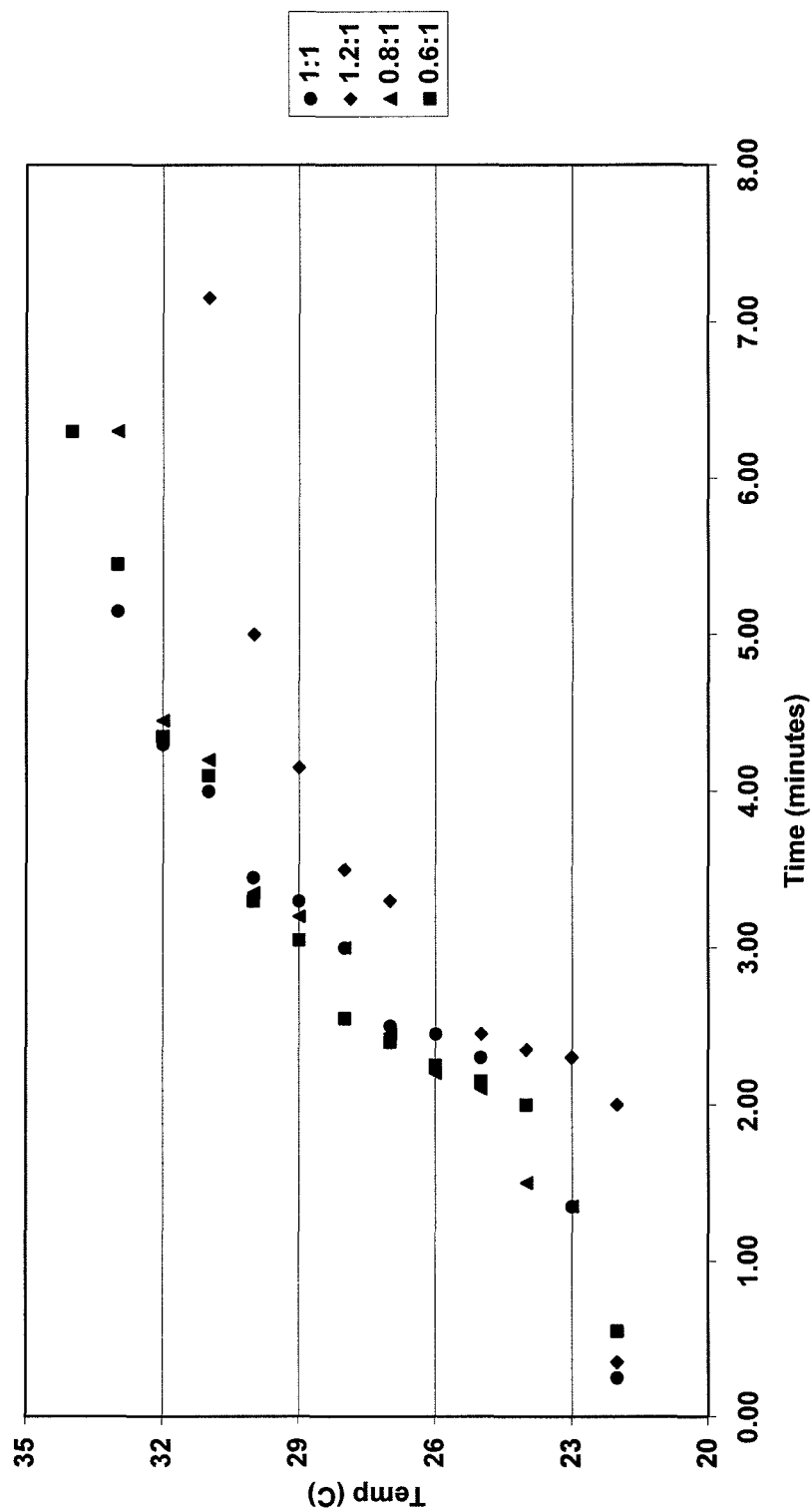
FIG. 16 is a graph showing temperature rise relative to time for compositions of the invention that include the indicated mole ratios of PEI (doped with CQ 222 pm) to ethoxylated (2) bisphenol-A-diacrylate.
Figure 17:
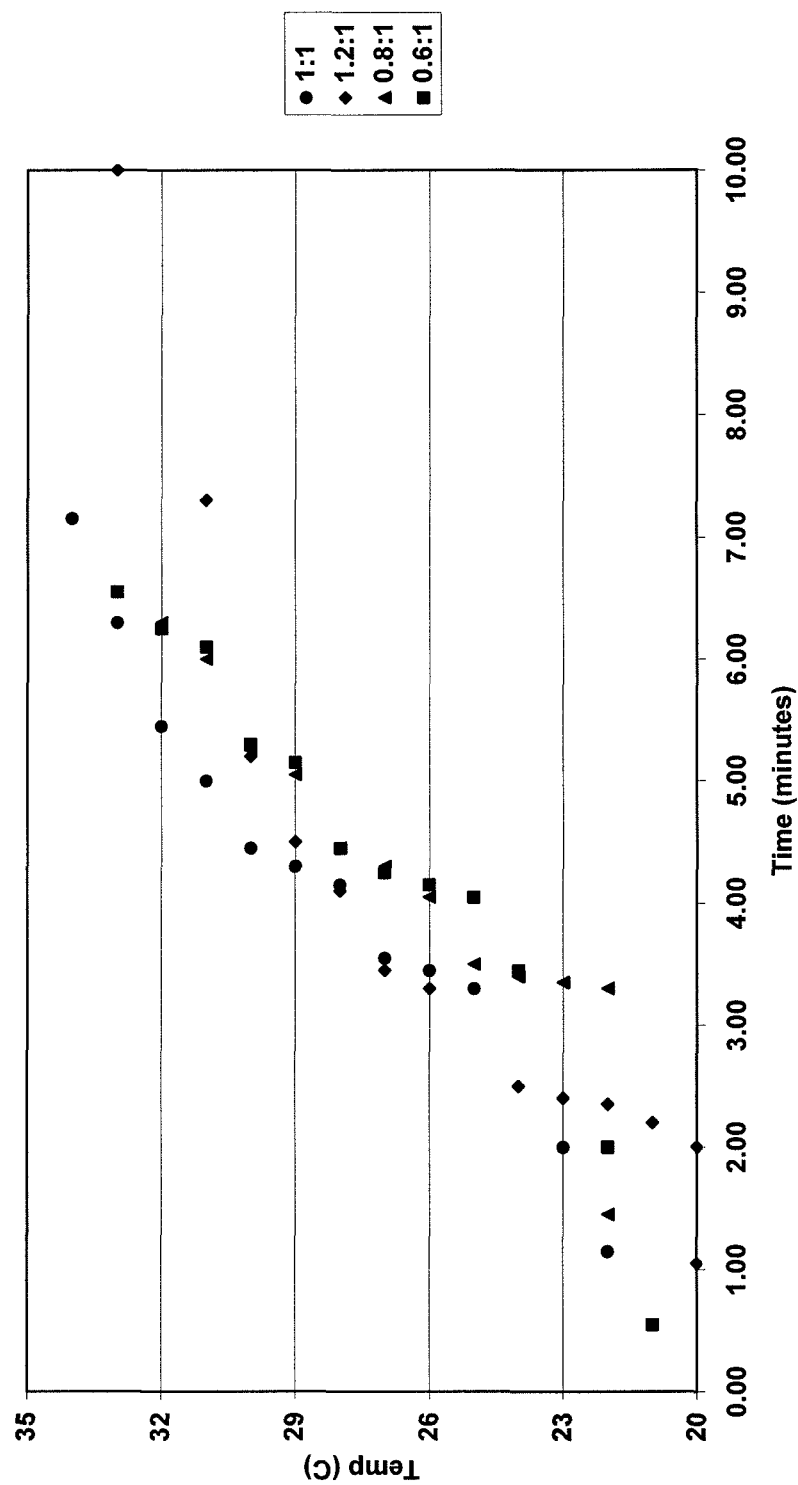
FIG. 17 is a graph showing temperature rise relative to time for compositions of the invention that include the indicated mole ratios of PEI (doped with CQ 222 pm) to ethoxylated (4) bisphenol-A-diacrylate.
Figure 18:
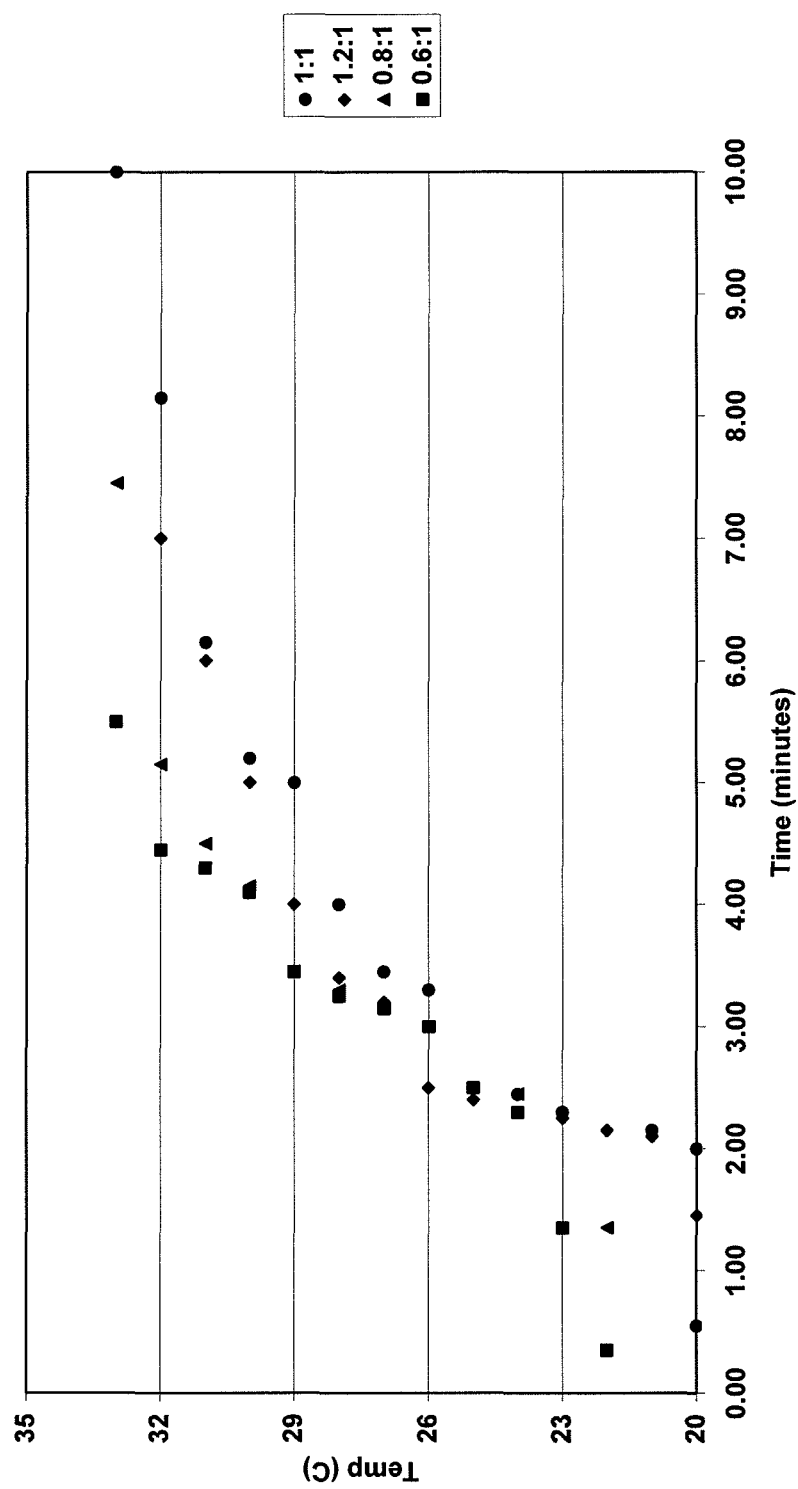
FIG. 18 is a graph showing temperature rise relative to time for compositions of the invention that include the indicated mole ratios of PEI (doped with CQ 0.5%) to ethoxylated (2) bisphenol-A-diacrylate.
Figure 19:
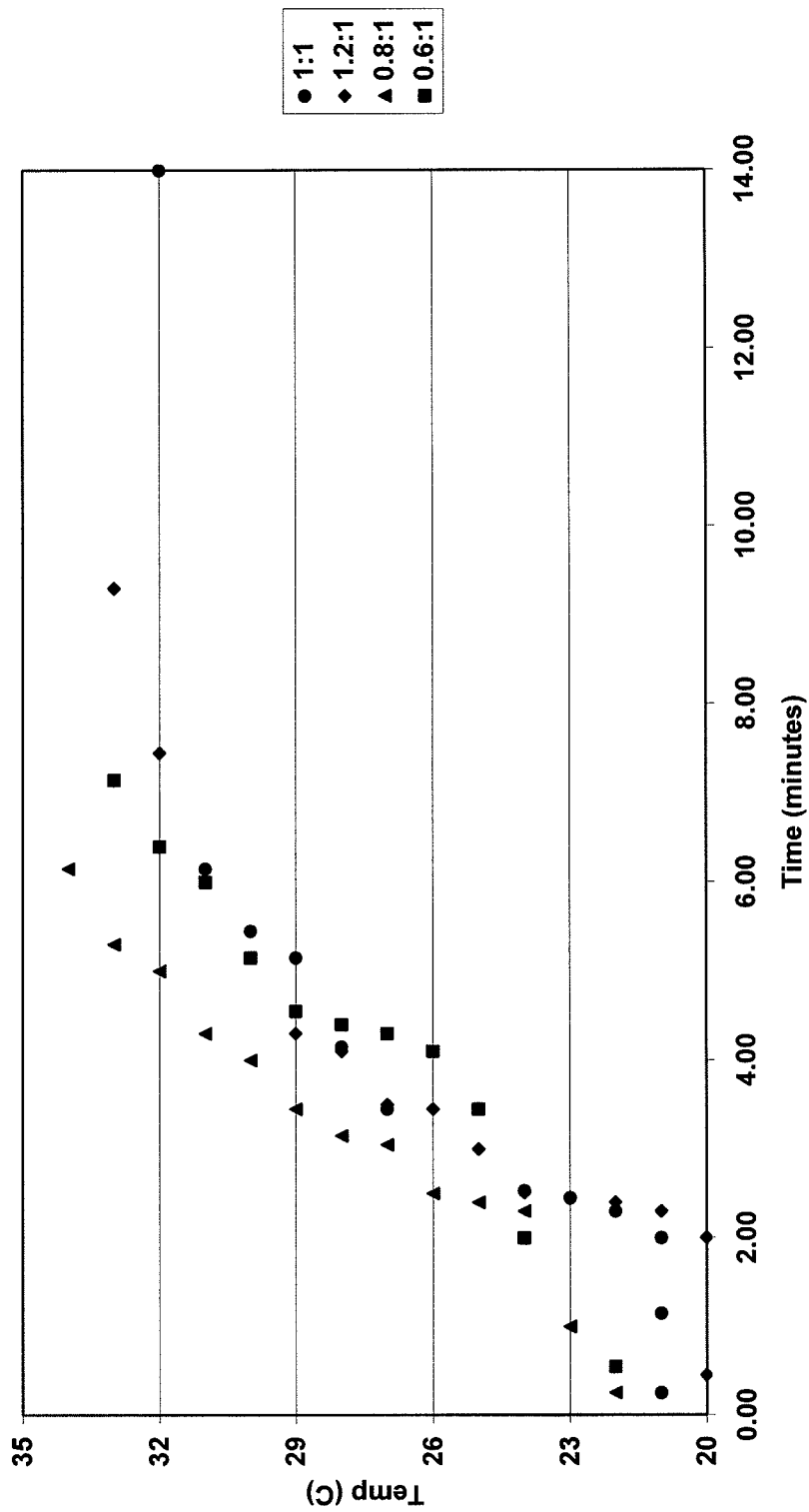
FIG. 19 is a graph showing temperature rise relative to time for compositions of the invention that include the indicated mole ratios of PEI (doped with CQ 0.5%) to ethoxylated (4) bisphenol-A-diacrylate.

As depicted in FIG. 10, the 0.5% CQ photoinitiator does produce a faster initial temperature rise in the 0.8:1 mole ratio PEI/PETA system, which eventually surpasses that seen in the 1:1 mole ratio PEI/PETA system shown in FIG. 10. This result may indicate that Michael addition reactions compete with visible light initiated free polymerization reactions due to a PEI deficiency in the 0.8:1 mole ratio PEI/PETA system.

The foregoing example indicates that stoichiometry of PEI and triacrylates can be important to achieving the optimum cure for a given application. The example indicates that the PEI mole ratios have a variability tolerance of up to +/−20%.

Example 15

The following example describes experiments performed to determine the temperature rise and set times associated with cement products of the invention formed by mixing various ratios of a first component and a second component with or without CQ photoinitiator.

Reaction conditions were the same as those described for Examples 12, 13 and 14, except as indicated. In the first set of experiments PEI-800 was mixed with ethoxylated (2) Bisphenol A diacrylate (E(2)BisDA) (ethoxy:phenol ratio of 1:1) or ethoxylated(4) bisphenol A diacrylate E(4)BisDA (ethoxy:phenol ratio of 2:1). In the second set of experiments, 222 ppm CQ photoinitiator was dissolved in PEI-800, and the doped PEI-800 was mixed with E(2)BisDA or E(4)BisDA. In the third set of experiments, 0.5% by weight CQ photoinitiator was dissolved in PEI-800, and the doped PEI-800 was mixed with E(2)BisDA or E(4)BisDA. Each individual mixtures included a (doped or undoped) PEI-800:diacrylate ratio of 0.6:1, 0.8:1, 1:1 or 1.2:1. Temperature rises over time are shown in FIGS. 14, 15, 16, 17, 18, and 19.

The maximum temperature rise for all reactions was below body temperature. For both sets of reactions, (i) the set times for a E(4)BisDA system is double that of the respective E(2)BisDA system and (ii) at PEI-800:diacrylate ratios of 0.8:1, 1:1 or 1.2:1, a E(4)BisDA system are more rubbery than the respective E(2)BisDA system. Generally, a higher PEI-800 ratio and a longer time in incubator oven gave a harder finish.

The CQ photoinitiator had little or no effect at PEI-800:diacrylate ratios of 1:1 and 1.2:1 for both diacrylates. However, increasing doses of CQ photoinitiator caused earlier and faster temperature rises for systems with lower PEI-800:E(2)BisDA ratios of 0.6:1 and 0.8:1, relative to the higher 1:1 and 1.2:1 ratios. The effect was less pronounced for E(4)BisDA systems.

A short light treatment (prior to oven incubation) of the dough formed using 0.6:1 PEI-800:E(2)BisDA systems with CQ photoinitiator, shortened set time and improved finish after oven incubation overnight. The 0.6:1 PEI-800:E(2)BisDA system with 0.5% CQ photoinitiator produced a rocky hard finish after incubation overnight.

The foregoing example indicates that, when PEI is stoichiometric (1:1) or in excess (1.2:1), Michael additions are preferred and, therefore, temperature rises are minimized. The example also indicates that higher ethoxylation results in slower Michael addition reactions, which reduces the impact of impact of photoinitiator CQ on the free radical polymerization of E(4)BisDA.

Example 16

The following example describes the temperature rise and set times associated with cement products of the invention formed by mixing PEI-800 with various relative amounts of a first component that includes equimolar mixture of E(2)BisGMA, BisGMA, and GMA.

Figure 20:
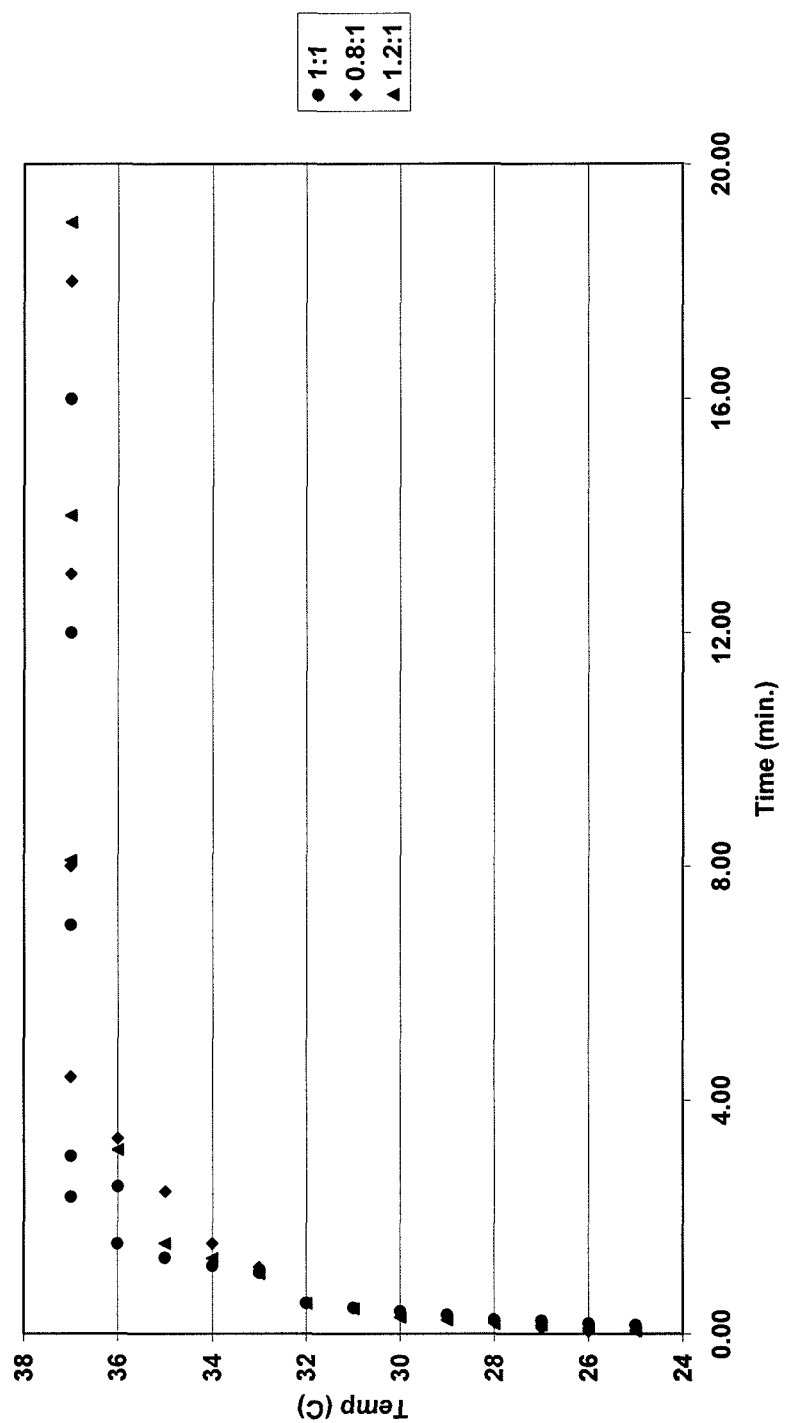
FIG. 20 is a graph showing temperature rise relative to time for compositions of the invention that include the indicated mole ratios of PEI to a first component that includes an equimolar mixture of E(2)BisGMA, BisGMA, and GMA.

Reactions conditions were the same as those described for Example 12, except where explicitly noted. Each individual mixture included PEI:first component ratio of 0.8:1, 1:1, or 1.2:1. Results are shown in FIG. 20. The tested system did not set within 15 minutes.

The foregoing example indicates that in order to optimize the tested systems to achieve a 15 minute set time, it may be necessary to use a higher power visible light lamp and/or to adjust levels of photoinitiator, thermoinitiator, and Michael addition reactions.

Example 17

The following example illustrates compression strength characteristics of several cement products of the invention.

Each first component resin was mixed with PEI-800 at the specified ratio indicated in Table 14. After setting, each product was evaluated with an MTI 10K compression tester (Measurements Technology, Inc., Roswell, Ga.) with a crosshead displacement rate of 10 mm/min. Compression testing was performed according to ASTM C773 (ASTM International) (Procedure B). Work and set times as well as strength characteristics for each product are shown in Table 14.

TABLE 14

| First Component Resin | Work time/ Set time (min.) | PEI-800:First Component Mole ratio | Average Compression Modulus (MPa) | Average Compression strength (MPa) | Average Deflection % |
|---|---|---|---|---|---|
| E(2)BisDA | 5 min/ 15 min | 1:1 | 30 | 75 | 50.28% |
| E(2)BisDA | 8 min/ 25 min | 1.6:1 | 76.53 | 20.33 | 50.91% |
| BisGMA GMA (1:1 mole ratio) | 20 min/ 20 hrs | 1:1 | 434 | 111 | 70% |
| SR9035 GMA (1:1 mole ratio) | 5 min/ 15 min | 1:1 | 13.56 | 2.08 | 16% |
| GMA | 30 min/ 5 days | 1:1 | 154.84 | 48.5 | 81.82% |

The BisGMA-GMA-PEI system had a maximum compression modulus of 434 MPa, a maximum force of 4287 N, maximum peak stress of 111 MPa, and maximum strain of 70%. The solid tube was compressible and recovered to its original length after stress was released. The BisGMA-GMA-PEI system has better hydrolysis resistance.

To control the hydrophilicity of finished polymer systems, divinylbenzene (DVB) and vinyl benzyl chloride (VBC) were mixed with PEI. DVB highly inhibited Michael addition, and therefore may require adding a Michael addition catalyst in these systems. The PEI/VBC system underwent Michael addition similarly to PEI/diacrylate systems. If PEI was deficient, prolonged heating at 37° C. overnight, resulted in the PEI/VBC giving off HCl and foaming of the neat polymer cement. Thus, a slight excess of PEI in the cement formulation is required to neutralize the excess HCl.

The preceding example shows that BisGMA-GMA-PEI has good work time (15-30 minutes) and excellent compression strength characteristics for use in bone cement formulation. To lower the viscosity of BisGMA, e.g., for use in a filled cement, a relatively small amount of GMA or ethoxylated (2) bisphenol A diacrylate can be added.

Additionally, the example shows that the E(2)BisDA-PEI (1:1 ratio) system has fast (5-10 minutes) dough (work), good optimum hardness of greater than 70 MPa and high deflection % of greater than 50%. These characteristics indicate that both BisGMA-GMA-PEI and E(2)BisDA-PEI (1:1 ratio), or derivatives thereof may be used in synthetic cartilage compositions.

Example 18

The following example illustrates the compression strength characteristics of several cement products of the invention that include a powder filler.

Fillers used in this example had the following characteristics: dense powder particle size: <50 micron, dense power surface area: 0.5 to 5 m2/gm, dense powder pore volume: <0.01 cm3/gm. Specific fillers included SP2525, a 200 mesh glass powder from Specialty Glass Inc. (Oldsmar, Fla.), BAB-HA-G1, BAB-HA-G2, and BAB-HA TCP-G2 dense powders from Berkeley Advanced Biosystem (Berkeley, Calif.), C1155, tribasic calcium phosphate powder from Spectrum Chemical (Gardena, Ca), Dense HA, a dense powder from chipped compressed and fired slogs from Angstrom Medica, Inc. (AMI, Woburn, Mass.) SDI K HA, a spray dried and calcined (at 1000° C.) powder from AMI, and nanoHAW whiskers from AMI.

A first component, PEI-800 (with or without CQ photoinitiator) and a filler component were mixed according to relative amounts indicated in Table 15. Work and set times as well as strength characteristics for each mixture are shown in Table 15.

powder may have soaked a significant amount of monomer liquid in the pores, thus sequestering and reducing the availability of reactive oligomers for curing as well as producing localized improper stoichiometry reactions which resulted in brittle products.

Generally when using PEI as a curative, viscosity can be diluted with GMA resin, either alone or with another waxy oligomers such as BisGMA. However, GMA tends to generate tremendous exotherm heat when epoxy-epoxy homopolymerization and epoxy-amine chain reactions occur. Therefore, the amount of GMA used in the formulation should be limited.

Mixtures including (a) predominately aliphatic (GMA) and hydroscopic (SR9035 and PEI) backbones and (b) tricalcium phosphate filler failed dissolution tests within hours if not minutes. Mixtures containing aromatic and hydroscopic (BisGMA, E(2)BisDA, DVB, VBC) were more stable in dissolution tests. However, DVB and VBC have a distinct smell, which renders them less desirable for some applications. Using SR9035 as predominated resin can also be unfavorable because it quickly decomposes and dissolves by de-Michael addition.

Figure 21:
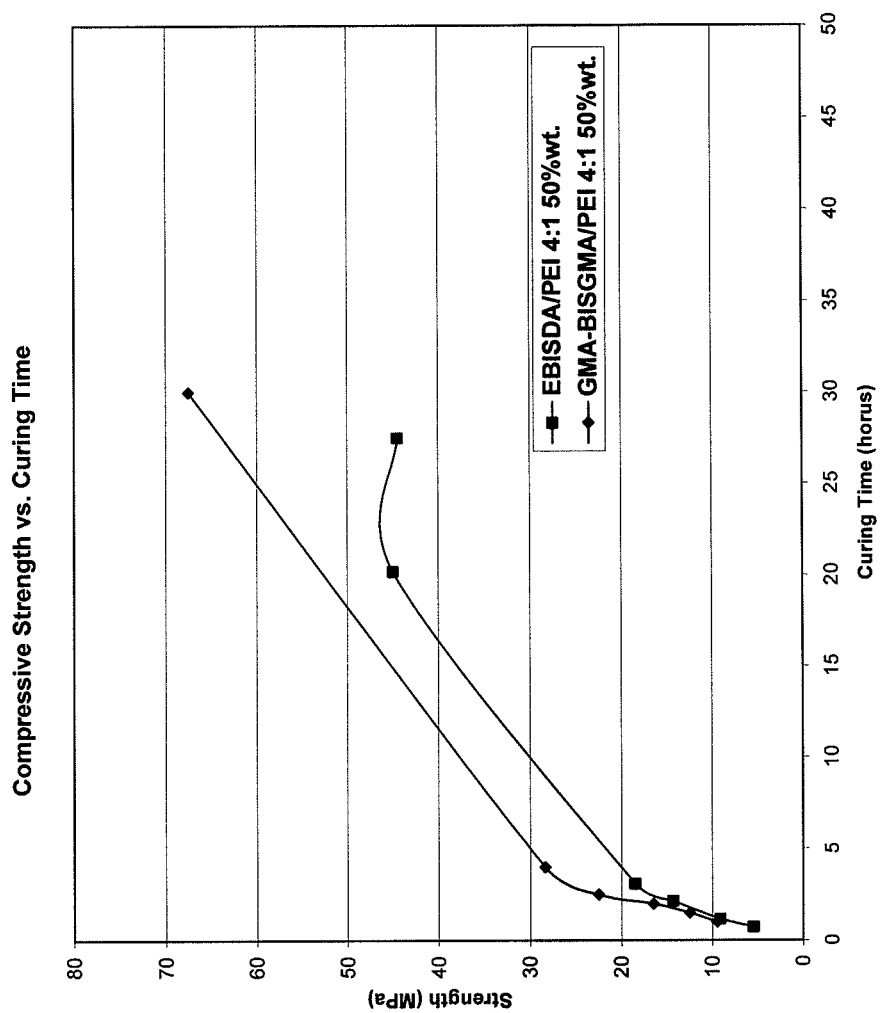
FIG. 21 is a graph showing strength relative to cure time for two cement formulations.

FIG. 21 shows compression strength of two cements more than 24 hours after set, at body temperatures. The first cement included a E(2)BisDA:PEI (4:1) and the second cement included E(2)BisGA+BisGMA:PEI (4:1), while both cements also included a 50% (w/w) loading of SDIK HA (spray dried and 1000° C. calcined HA dense powder). The E(2)BisGA+BisGMA:PEI (4:1) dense powder system achieved a targeted compression strength of 50 MPa after one day at body temperature.

TABLE 15

| First Component Resin (R) | Curative (C) | Filler | Filler w/w % | Work/ Set T (min.) | Average C Modulus (MPa) | Average Compression strength (MPa) | Average deflection % |
|---|---|---|---|---|---|---|---|
| SR9035 GMA DVB-80 | PEI-800 | AMI nanoHA | 33% | 5 min/ 10 min | 77.5 | 21.33 | 35.4% |
| SR9035 BisGMA GMA VBC | PEI-800 | nanoHA | 33% | 12 min/ 25 min | 38.5 | 12.5 | 37.4% |
| E2BisDA | PEI-800 CQ | AMI's nHAW | 35% | 5 min/ 15 min | 136.3 | 39.6 | 34.6% |
| E2BisDA | PEI-800 CQ | AMI's nHAW | 45% | 5 min/ 15 min | 101 | 21 | 21.8% |
| E2BisDA BisGMA GMA | PEI:800 | SDIK HA | 50% | 9 min/ 39 min | 582 | 59.7 | 31.7% |
| E2BisDA | PEI:800 | SDIK HA | 50% | 15 min/ 60 min | 255 | 52 | 25.8% |
| GMA SR9035 DVB-80 | PEI-800 | AMI Dense + nanoHA | 63% | 15 min/ 25 min | 171.3 | 48.2 | 34.6% |
| BisGMA GMA | PEI:800 | SDIK HA | 67% | 15 min/ 60 min | 117 | 22.3* | 23.6% |
| GMA DVH-80 SR9035 | PEI-800 | BAB-HA-G1 | 70% | 13 min 26 min | 633.0 | 84 | 15.7% |
| SR9035 BisGMA GMA VBC | PEI-800 | SG1 Glass Powder | 74% | 10 min/ 18 min | 47 | 21.5* | 50.3% |
| GMA DVB-80 SR9035 | PEI-800 | BAB-HA-G1 & G2 | 78% | 10 min/ 20 min | 86.5 | 6.5* | 11.6% |
| GMA DVB-80 SR9035 | PEI-800 | BAB-HA TCP-G2 | 78% | 10 min/ 20 min | 294 | 32 | 14.6% |

Figure 22:
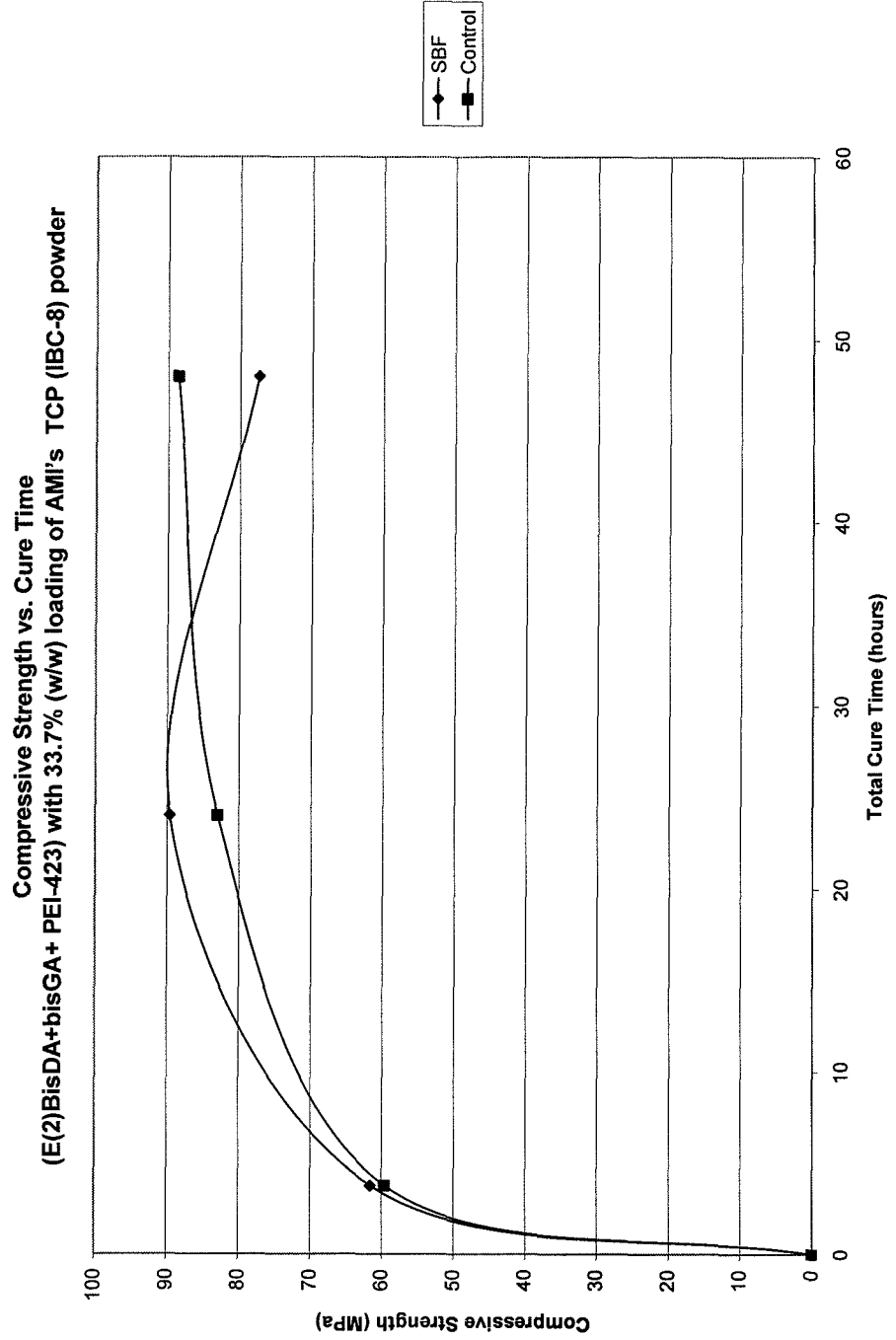
FIG. 22 is a graph showing strength relative to cure time for two cement formulations in the presence or absence of simulated body fluid (SBF).

Additional experiments indicated that NanOss nanocrystalline HA powder could not suitable be loaded into PEI-800 cement systems beyond 50% (w/w), while for acrylate systems, loading was limited to less than 40% (w/w). These limits are related to the high microporosity of the nanocrystalline powder (surface areas are in the range of 400 m$^2$/gm and average particle size is in the range of 6 microns). The FIG. 22 shows compression strength as a function of curing time for a cement including E(2)BisDA+BisGA:PEI-423 and 33.7% w/w loading of AMI TCP (IBC-8) powder. Compression strength was measured at 37° C., in the presence or absence of simulated body fluid (SBF). Both the control and the SBF-treated cement achieved and maintained a targeted compression strength of greater than 50 MPa during the 48 hours testing period.

This example indicates that compression strengths of ~50-84 MPa were associated with dense particle hydroxyapatite fillers, loaded at 50% to 70% by weight. Good results were also seen with 33.7% by weight loading of TCP (IBC-8) powder. Outside of this loading range, compression strength suffered (either due to intrinsically weak nanoHA whiskers or nanoHA powders or due to insufficient dispersion and wetting). Air bubble entrapment likely contributed to weak compression strength of certain highly loaded formulations. Longer machine pigment grinding of higher than 70% powder loading may reduce defects of the finished composites. Additionally surface modified functional powders having compatible reactive functionality with the first and second component will likely improve mechanical strength of the finished cement.

Example 19

The following example illustrates the compression strength characteristics of cement products of the invention formed with components that model a liquid aromatic diamine.

Figure 23:
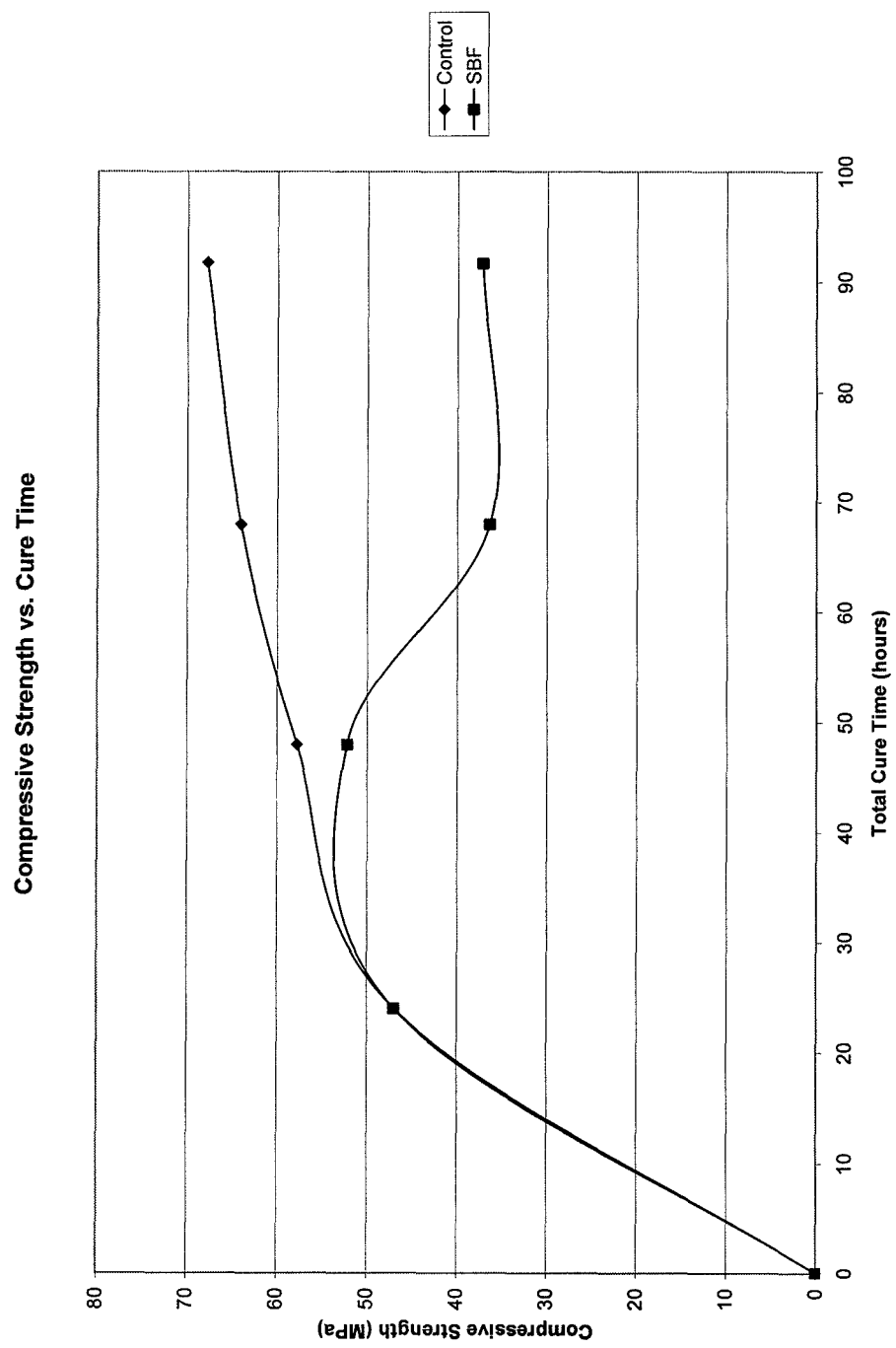
FIG. 23 is a graph showing strength relative to cure time for two cement formulations in the presence or absence of simulated body fluid (SBF).
Figure 24:
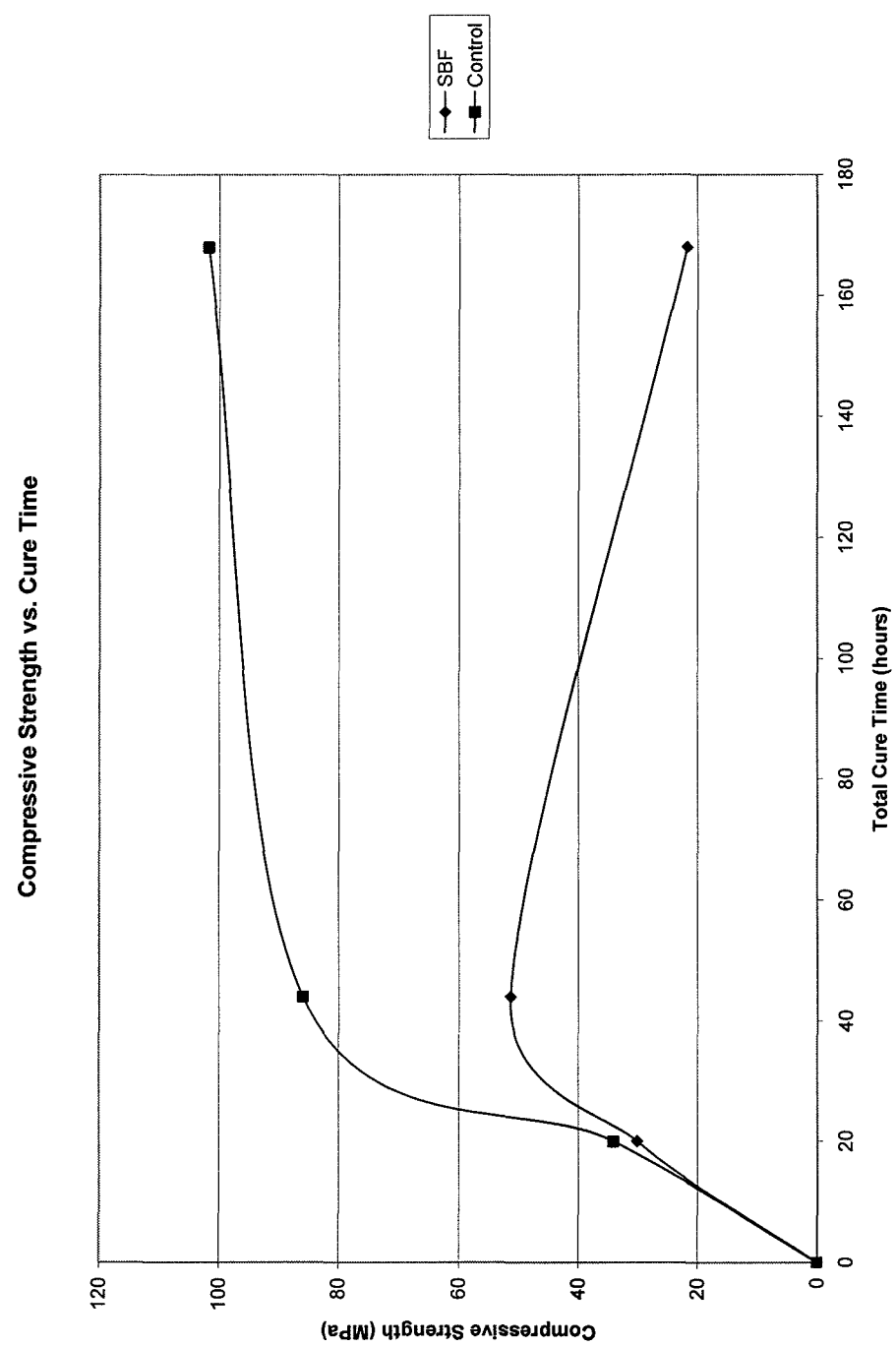
FIG. 24 is a graph showing strength relative to cure time for two cement formulations in the presence or absence of simulated body fluid (SBF).

A first component included a mixture a BisGA and ethoxylated(2) bisphenol A diacrylatephenylenediamine (mPDA). The second component included (a) 30% m-phenylenediamine (mPDA), (b) 30% o-cyclohexanediamine (o-CHDA), and (c) 40% PEI-800 in a weight ratio of 5:3:1 or 5:3:2, respectively. By way of background, mPDA is a low melting point solid that can be dissolved in liquid polyethyleneimine, and o-cyclohexanediamine is a liquid cyclic-aliphatic diamine. The first and second components were reacted in 1:1 mixture and set polymer was placed in air (control) or in 1× simulated bodily fluid (SBF) at 37° C. FIG. 23 shows the compressive strength as a function of cure time of the neat polymer formed from the 5-3-1 second component. FIG. 24 shows the compressive strength as a function of cure time of the neat polymer formed from the 5-3-2 second component.

The 5-3-1 polymer was so hydrophobic that water beaded up on its surface. Moreover after soaking in IX SBF for 3 weeks, the 5-3-1 polymer sample's diameter increased about 6%. The reduced compression strength of the 5-3-2 polymer in SBF may be due to excess hydrophilic PEI-800 branches, which absorb water and plasticize the polymer.

This example shows that a nucleophile curative system containing m-phenylenediamine polyethyleneimine and o-dcyclohexane-diamine (o-CHDA), if set with aromatic containing enone oligomers such as BisGA can have a very high compression strength of above 50 MPa. Moreover, such a system preserves its excellent dimensional and hydrolytic stabilities in SBF at body temperatures.

Example 20

The following example illustrates the compression strength characteristics of cement products of the invention that include (i) amino acids with amino-groups in their side chains or (ii) a heterocylic aromatic diamine.

The side chain amino groups of certain amino acid can serve as nucleophiles for the Michael addition to enones. Generally, amino acids are flaky or crystalline solids at room temperature, thus, they should be dissolved in a liquid to effectively participate in the set reaction. In the following experiments L-phenylalanine (PHE), L-Tryptophan (TRP), L-Lysine (LYS), L-cysteine (CYS), L-tyrosine (TYR), L-arginine (ARG), L-histidine (HIS) were dissolved in PEI and/or 1,4-diaminobutane (DAB). Certain amino acid solutions had a distinctive smell. DAB has a melting point of 25° C., although, upon moderate heating, amino acids and DAB formed a low viscosity liquid and stay as a liquid at room temperatures. This indicates that DAB containing systems may be useful for forming in situ biological active oligopeptide putty systems for applications where quick resorbability is desired.

Heterocyclic aromatic diamine containing compounds, which are similar to purine and pyrimidine containing biological nucleotides, were also dissolved in DAB and PEI. Dissolved compounds included guanidine carbonate (GUAC), diaminopurine (DAP), diaminopurine hemisulfate (DAPHS), 2,4-diamino-6-hydroxypyrimidine (DAHP), and 2-mecapto-uracil (DAHMP).

The solubility (w/w) of some of above mentioned materials in PEI were GUAC—25.2%, DAP—18.8%, DAHP—13.8%, PHE—61.24%, TRP—46.46%, ARG—21.9%, and CYS—18.2%. The solubility (w/w) of above mentioned materials in DAB were PHE—28%, TRP—29.4%, CYS—19.5%, LYS—16.1%, and TYR—32.1%.

A fast dough prototype containing CYS was developed, which has a polymer composition of A:B of 6.674:1, wherein Part A includes E(2)BisDA+BisGA (1:1 mole equivalents), and Part B includes Cysteine (18.23% w/w) dissolved in PEI-800.

Monomers were compounded by hand in a 250 mL PP vessel. After vigorous and thorough mixing, resin was poured and kneaded into SS-compression specimen mold. The mold compression plates were clamped shut using C-clamp and placed in oven for 24 hours at 37° C. to fully set. Specimens were then ejected from the mold and arbitrarily split into two subgroups. One group was placed into SBF at 37° C. while the other was placed in a weigh boat exposed to air and put into the same oven at 37° C. The control and SBF samples were allowed to cure for an additional 48 hours before being tested.

The first compression test was taken after specimens had been exposed to SBF for 48 hours (total cure time of 72 hours). Compression modes between SBF and control samples were indistinguishable. Samples did not show any swelling, weight gain, or surface erosion.

Table 16 below details the compressive strength of both control (air) and test (SBF) cured specimens. Several samples from data points 1 and 2 were censored due to large air voids within the specimen.

TABLE 16

| Data point | Type | Cure Time (hours) | Compressive Strength (mPa) | % Swelling (D) | % Swelling (L) |
|---|---|---|---|---|---|
| 0 | — | 0 | 0 | — | — |
| 1 | Control | 72 | 39 | 0 | 0 |
| 1 | SBF | 72 | 74.5 | 0.80 | 1.18 |
| 2 | Control | 168 | 35.8 | 0 | 0 |
| 2 | SBF | 168 | 12.2 | 1.26 | 1.42 |

The high strength of SBF cured samples after 72 hours is misleading. Neat polymeric samples tend to undergo drastic deformation, both in height and cross-sectional area when loaded. The test performed does not account for the drastic increase in load area resulting in reported stresses which are inaccurate and irrelevant. The goal of each compressive test is to determine the force required to cause a given part to yield. To this, the test is set to terminate when the normal force drops by 5% between any two points. Unfortunately, often the stress/strain curve does not facilitate this termination and the stress increases quasi-linearly until a max deflection of 55%. In short, sample C from SBF data point one was recorded as 104 MPa, when in reality the sample yielded at much lower stress.

The samples were allowed to cure three additional days, in solution and in air, before additional compressive testing was performed. Samples cured in SBF did not show any immediate qualitative signs of water degradation. Surfaces were smooth and stiff, and did not yield to the caliper faces during measurement, a quality characteristic of plasticized samples. As illustrated by Table 16, quantitative measurements did not show significant swelling (1-2%). The percentages shown in Table 16 indicate percent increase in diameter and length of test samples compared to control samples. Test samples cured in SBF yielded under significantly smaller loads than air cured controls. Failure modes of each were nearly identical, with an increase in diameter concentrated at the load faces while the body of the slug remained unchanged. The mere lack of strength and stiffness of test samples indicated plasticizing of the polymer by the fluid.

Example 21

The following example illustrates the characteristics of certain cement products of the invention.

Pentaerythritol triacrylate (PETA) reacted with o-cyclohexanediamine (o-CHDA). Putty set within 3 minutes with a maximum exotherm temperature of 58° C. The finished specimen was hard, having a compression strength of 25 MPa. Surprisingly, the set neat putty completely dissolved in water within 3 days. The rapid dissolution may be related to both ingredients being aliphatic.

Other monomers known to provide high glass transition temperature (Tg) finished polymers were reacted with PEI. These monomers were mostly aliphatic and included diethyleneglycol diacrylate, dipropyleneglycol diacrylate, glyceryl propoxy triacrylate, pentaerythritol triacrylate, and tris (2-hydroxy ethyl) isocyanurate triacrylate. They improved the hardness and compression strength of the set putty but did not affect their fast dissolution. These fast dissolution systems should work well for controlled release of bone nutrients, e.g., in bone void fillers applications.

We also tried to introduce simultaneous free radical polymerization and Michael addition by adding both benzyl peroxide (BPO) and p-dimethyltoluidine (pDMT) into the system. BPO and pDMT were intended to anchor C—C linkage on the main polymer chain and secure hydrolytical stability over time. Generally, since the reactions involved are competing simultaneous rapid reactions, room temperature Michael addition occurred first, forming C—N imine main chain and preventing the heat accumulation needed to initiate free radical C—C main chain formation.

The ratio of C—C linkage formation in the main chain can be increased, however, by using acetoacetonates containing monomers such as 2-(acryloyloxy)ethyl acetoacetonate (Aldrich Cat no.: 497126) or allyl acetoacetate (Aldrich cat. No.: 254959) to react with di(meth)acrylates or tri(meth) acrylates. Michael addition occurs at higher temperatures and does not require diamines participation. BPO and pDMT can be introduced to accelerate the rates of reaction, thereby facilitating the simultaneous occurrence of hybrid free radical reactions and Michael addition reactions.

This example shows that certain combinations of an aliphatic first component and an aliphatic second component form a hard cement that rapidly dissolve in aqueous environments. These systems may be useful for applications such as bone void fillers. For weight bearing, long term, slow dissolution applications, the cements may require using monomers with an aromatic and/or other hydrophobic moiety.

Example 22

The following example illustrates the exotherm characteristics of certain cement products of the invention.

The following epoxy-containing first components were developed: 5.7.1, which includes ARALDITE 506 epoxy resin (Ciba-Geigy, Brewster, N.Y.) and poly[(phenyl glycidyl ether)co-formaldehyde] (PPGEF) (1:1 milliequivalents); 5.7.2, which includes PPGEF+Neopentyl glycol diglycidyl ether (NPGDGE) (3:1 milliequivalents); and 5.7.3, which includes PPGEF+N,N-Diglycidyl-4-glycidyloxyaniline (DGGOA) (2.5:1 milliequivalents). Each of these first components was compounded with a stoichiometric (i.e., based on PEI-800 dalton oligomer mole equivalent weight of 43 dalton) amount of PEI-800 loaded with 15% (weight of total polymer) ZnS. More specifically, PEI-800 was measured first, ZnS powder was incorporated into the PEI-800, and then the first component was added and mixed vigorously. Cement C090 included 4.40 g first component 5.7.1, 1.057 g PEI-800 and 0.963 g ZnS. Cement C091 included 4.98 g first component 5.7.2, 1.133 g of PEI-800, and 1.079 g ZnS. Cement C092 included 4.59 g first component 5.7.3, 1.276 g PEI-800, and 1.035 g ZnS.

Figure 25:
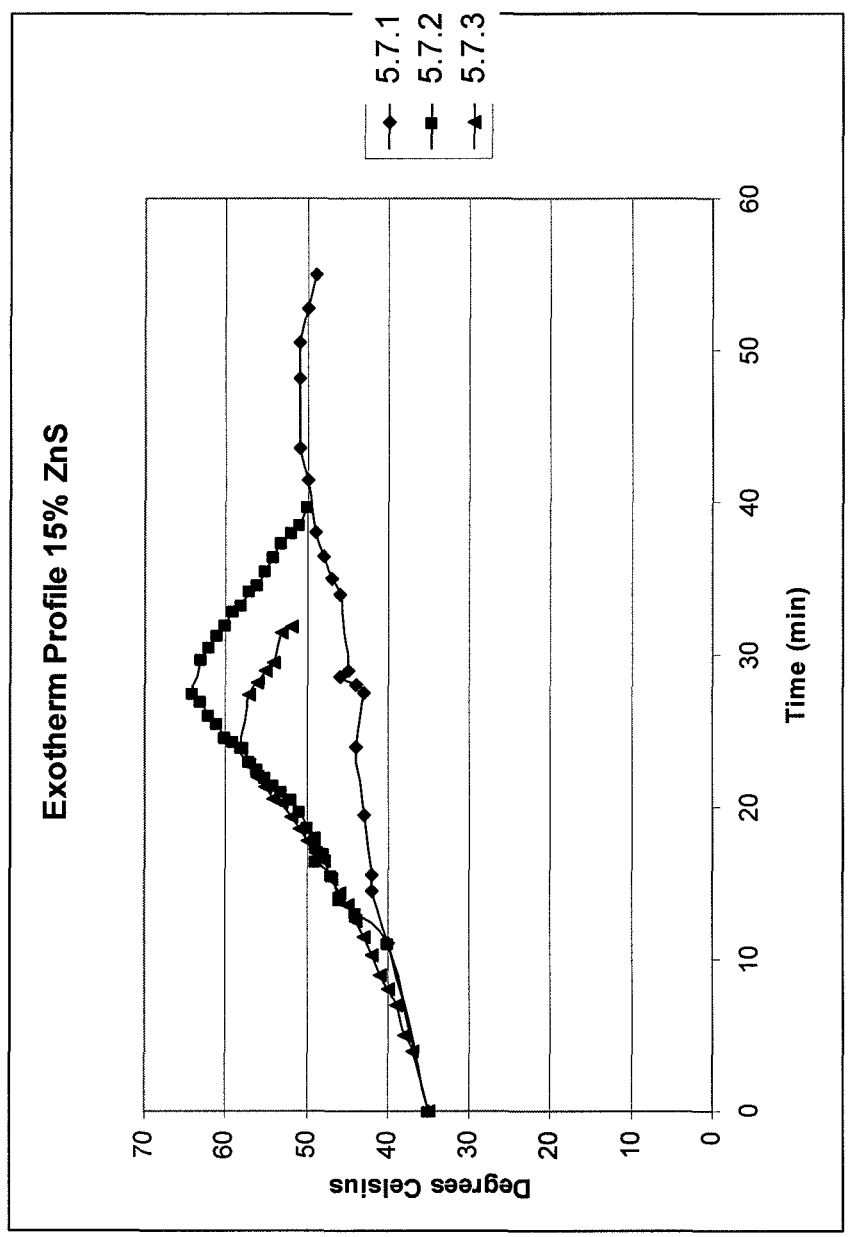
FIG. 25 is graph showing temperature rise relative to time for compositions of the invention that include the indicated epoxy-containing first component and 15% ZnS.

Compounded formulations were placed in a 37° C. incubating oven, a stainless steel thermocouple was inserted into each sample container through the cap, and samples were monitored closely for temperature variation and time. FIG. 25 illustrates the exothermic behavior of each polymer while setting. Samples become set just before the maximum exothermic levels are recorded.

In other reactions, first components 5.7.1, 5.7.2, and 5.7.3 were compounded with a stoichiometric amount of PEI-800 and from 0-15% of ZnS. Compounded formulations were placed in a 37° C. incubating oven and exothermic data was measured as described above. Maximum exothermic temperature are shown in Table 17.

TABLE 17

| | Catalyst | ° C. | Time (min) |
|---|---|---|---|
| 5.7.1. + PEI-800 | None | 62 | 38 |
| | 3% ZnS | 66 | 30 |
| | 10% ZnS | 66 | 31 |
| | 15% Zns C090 | 51 | 43 |
| 5.7.2. + PEI-800 | None | 120 | 25 |
| | 3% ZnS | 56 | 30 |
| | 10% ZnS | 53 | 33 |
| | 15% Zns C091 | 64 | 27.5 |

TABLE 17-continued

|  | Catalyst | ° C. | Time (min) |
|---|---|---|---|
| 5.7.3. + PEI-800 | None | 125 | 19 |
|  | 3% ZnS | 128.5 | 18.5 |
|  | 10% ZnS | 83 | 23 |
|  | 15% Zns C092 | 58 | 24 |

Data in Table 15 for 5.7.1, and 5.7.3 indicates that increasing the level of catalyst generally lowers maximum exothermic temperature and increases setting time. Sample 5.7.2, however, demonstrated the opposite effect when moving from 10% to 15% catalyst, since the reaction temperature increased and reaction time decreased.

In other experiments, 5% ZnO (w/w) was added to 5.7.1, 5.7.2, and 5.7.3 epoxide systems with 5%, 10% or 15% ZnS. The rise in temperature over time shown in FIG. 26 indicates that ZnO further decreases the exotherm relative to systems with 15% ZnS shown in FIG. 25.

The preceding example indicates that certain epoxy cement systems according to the invention have desirable exothermic properties. Such epoxy systems are expected to provide excellent hydrophobic characteristics. The preceding example also indicates the value of using other aromatic epoxy compounds, such as Bisphenol A propoxylate (1 PO/phenol) diglycidyl ether, in the first component of the invention. The preceding example (in combination with other Examples disclosed herein) indicates that the second component for these epoxy systems can benefit from the use of polyethyleneimine doped with amino acids, such as cysteine, polycysteine, tyrosine or polytyrosine.

Moreover, epoxy cement systems of the invention can be further set with curatives other than amine, such as polysulfides, polyamides, polyimides, polyamic acid, polyols, polyanhydrides and polyaldehydes. The neat epoxy cement further filled with calcium phosphates, such as nano powder of hydroxyapatite, tricalcium phosphate, calcium carbonate, calcium sulfate and bioglass at a loading from 0% to 99% (w/w), for each individual powder or in any combinations.

Example 23

The following example illustrates the dough time characteristics of certain cement products of the invention.

First product: Trans-cyclohexanediamine: (t-CHDA) (0.571 gm) was mixed with Epomin™ SP003 (PEI with approximate molecular weight of about 300, available from Shinwoo Advanced Materials, Seoul, Korea) (0.354 gm) and compounded with PETA (1.610 gm). Dough time was 1 minute and maximum temperature was 45° C. at 1 minute. Reverse osmosis (RO) purified water was added after 3 minutes. The water turned clear to amber clear. Water pH on first day was about 10, on second day about 9, and after three weeks pH was about 6. The polymer was clear and stuck to the side of vial.

Second product: t-CHDA (0.612 gm) and tetramethylamminium hydroxide (0.034 gm) were mixed with PETA (1.120 gm). Dough time was over 8 minutes and maximum temperature was 42° C. Water was added after 9 minutes. Water was clear to amber clear. Water pH on first day was about 10, on second day about 7, and after three weeks pH was about 6. Polymer was white.

In the following experiments C067 represents a mixture of CHDA and m-phenylene diamine (m-PDA) with one to one mole ratio.

Third product: C067 (0.578 gm) was mixed with PETA (1.034 gm). No dough formed after 35 minutes and maximum temperature was 28° C. Water added after 9 minutes produced a light greenish-blue solution. Water pH on first day was about 7, on second day about 7, and after three weeks pH was about 6. Polymer was clear.

Fourth product: C067 (0.591 gm) and DABCO (0.100 gm) were mixed with PETA (1.032 gm). No dough formed after 23 minutes and maximum temperature was 35° C. Water added after 24 minutes produced a light greenish-blue solution. Water pH on first day was about 8, on second day about 7, and after three weeks pH was about 5.5. Polymer was white.

Fifth product: C067(0.599 gm) and EPOMIN™ SP-003 (0.286 gm) were mixed with PETA(1.768 gm). Dough time was 2 minutes and maximum temperature was 35° C. Water added after 3 minutes turned a light teak clear solution. Water pH on first day was about 9, on second day about 9, and after three weeks pH was about 6. Polymer was clear.

Sixth product: C067(0.598 gm) and EPOMIN™ SP-003 (0.050 gm) were added to PETA (1.011 gm). Dough was 9 minutes and maximum temperature was 31° C. after 2 minutes. Water added after 10 minutes turned light greenish-blue clear water solution. Water pH on first day was about 8, on second day about 7, and after three weeks pH was about 5.5. Polymer was clear.

Seventh product: C067 (0.597 gm) and EPOMIN™ SP-003 (0.092 gm) were added to PETA (1.654 gm). Dough was 9 minutes and maximum temperature was 28° C. in 2 min. Water added after 10 minutes turned light greenish-blue solution. Water pH on first day was about 9, on second day about 7, and after three weeks pH was about 5. Polymer was clear.

The preceding example shows that Epomin™ SP-003 can shorten dough time to under 10 minutes. Epomin™ SP-003 is a PEI with approximate molecular weight of about 300 Da and a primary to secondary to tertiary amine ratio of 45:35:20.

Example 24

The following example illustrates the dough time characteristics of certain cement products of the invention.

Mixtures 9A (PEI-800 (21.601 gm, liquid) and guanidine carbonate (7.304 gm, crystals)), 9B (PEI-800 (21.605 gm, liquid) and arginine (8.744 gm, crystals)), and 9C (PEI-800 (21.590 gm) (liquid) and cysteine (4.807 gm) (crystals)) were each made by stirring the indicated components and heating in a laboratory oven at 60° C. over two days. The mixtures removed from the oven were phase separated into two layers, with a cake settlement on the bottom. Mixtures were stirred for several minutes to a putty-like finish, and then they were placed on a hotplate with a temperature of about 50° C. (except for mixture 9A, which contains guanidine).

Mixture 9D was made by mixing E(2)BisDA: BisGA with 1:1 mole ratio.

Eighth cement product: 9D (4.973 gm) was mixed with 9A (1.072 gm) in a 5 ml vial. It formed viscose glue-like solution quickly. Filling straw was taken after 2 minutes. No exotherm observed. Mixture had a dough time of 3 minutes. After 4 minutes RO water was added to the vial. Both the vial and the straw were placed in a 37° C. oven. After 45 minutes, the polymer hardened like a rock and appeared to be completely dry.

Ninth cement product: 9D (5.343 gm) and 9B (1.012 gm) were mixed in a 5 ml vial. Maximum temperature was 34°

C. in 2 minutes. After 3 minutes of mixing a filled straw was taken. After 4 minutes RO water was added to the vial. Both the vial and the straw were placed in a 37° C. oven. After 17 minutes, the compound was still sticky. After 25 minutes the compound was solidified and tacky. After 37 minutes the compound was still tacky.

Tenth cement product: 9D (3.270 gm) and 9C (0.686 gm) were mixed in a 5 ml vial. No exotherm observed. Filled a straw was taken after 1 minutes. Mixture had a dough time of 3 minutes. After 5 minutes RO water was added to the vial. Both the vial and the straw were placed in a 37° C. oven. After 7 minutes, the mixture hardened and turned tacky. After 18 minutes, was dried and tack-free.

After 70 minutes, the eighth, ninth and tenth cement product were hardened like a rock and dry to touch. Vials filled with water had no observable dissolution debris floating or precipitating.

Eleventh cement product: 9D (5.148 gm) and 9A (1.229 gm) were mixed in a 5 ml vial. No exotherm was observed. Filled a straw after 1.5 minutes. The mixture had a dough time of 3.5 minutes. After 5 minutes RO water was added to the vial. Both the vial and the straw were placed in a 37° C. oven. Both the straw and vial were placed in the 37° C. oven. After 15 minutes, the mixture was hardened and felt tacky.

Example 25

The following example illustrates fast resorbable cement products of the invention. The o-diaminocyclohexane used was DYTEK™ DCH-99 from Invista (Wilmington, Del.).

First resorbable product: PETA and o-diaminocyclohexane (2:1 w/w) were mixed. Dough time was 20 minutes and exotherm temperature rise was 35° C. within 2 minutes. This product did not set as fast as a PETA:o-diaminocyclohexane at 1:1 [(meq c=c):(meq primary amine)], which had a temperature rise to 58° C. in 2 minutes and dough time of 10 minutes.

Second resorbable product: PETA (1.987 gm) was mixed with o-diaminocyclohexane (0.581 gm). No dough was formed after 2.5 hours. Temperature rise was 38° C. within 3-4 minutes. After 3-4 minutes a straw was filed and plugged and put it in 37° C. incubator oven.

Third resorbable product: PETA (2.027 gm was mixed with o-diaminocyclohexane (1.171 gm). Dough time was 10 minutes and temperature rise was 58° C. in 2 minutes. A straw was filled after 3-4 minutes and placed in incubator oven after 5 minutes. The vial was filled with RO water after 7 minutes. After 28 minutes the mixture was a tacky, soft, flexible, and clear solid. Mixture became a harder solid after 1.5 hours.

Fourth resorbable product: PETA (2.003 gm), o-diaminocyclohexane (0.670 gm), and PEI-800 (0.434 gm) were mixed. Dough was 1.5 minutes and temperature rise was 38° C. in 1 minute. Mixture solidified into a rubbery solid within 3 minutes.

Fifth resorbable product: PETA (19.985 gm) and o-diaminocyclohexane (11.436 gm) were mixed. The mixture was initially very fluid. After stirring, temperature rose from 17° C. to 95° C. within 2 minutes. The whole mixture set-up after 4 minutes of mixing.

All leftover vials of the first through fifth resorbable products were soaked with RO water. The solution was crystal clear. The products were fully dissolved after 3 days.

Example 26

The following example illustrates hydrolytically stable cement products of the invention that include an aromatic diamine. In the following example, 9D refers to mixture 9D of Example 24.

First aromatic diamine product: EPOMIN™ SP003 (1.030 gm) and 9D (4.979 gm) initially formed a thick mixture. After stirring, temperature went up from 17° C. to 45° C. within 2 minutes. The mixture set-up within 4 minutes of mixing.

For the following products, solution 16 A was made by mixing DYtek™ DCH99 (57.136 gm, liquid) with m-PDA (58.185 gm, flakes), heating the mixture at 50° C. for 4 hours until all the m-PDA dissolved to a clear brownish low viscosity liquid.

Second aromatic diamine product: 9D (4.726 gm) was mixed with 16A (0.586 gm). Temperature rose from 22° C. to 34° C. within 2 minutes. A straw was filled after 3 minutes of mixing. After 26 minutes, no dough was observed and the mixture was very sticky. After 100 minutes the mixture remained a sticky soft gel. Water added to the vial resulted in a small quantity of oily droplets floating on the top of water.

Third aromatic diamine product: 9D (5.385 gm), 16A (0.628 gm), and PEI-800 (0.416 gm) were mixed. Temperature rose from 22° C. to 41° C. in 2 minutes. A straw filled after 2 minutes. After 30 minutes the mixture is solid and tacky. After 50 minutes later the mixture is dry to the touch.

Fourth aromatic diamine product: 9D (5.079 gm), 16A (0.493 gm) and PEI-800 (0.240 gm) were mixed. Temperature rose from 22° C. to 37° C. in 2 minutes. A straw was filled after 4 minutes. After 30 minutes the mixture was very sticky and not gel. After 1 hour, the mixture was a sticky soft gel. The product did not include enough PEI.

Fifth aromatic diamine product: 9D (4.346 gm), DCH99 (0.509 gm) and PEI-800 (0.121 gm) were mixed. Temperature rose from 22° C. to 36° C. in 2 minutes, After 3 minutes a straw was filled. After 7 minutes, R.O. water was added to the vial. After 30 minutes, mixture was still soft and sticky. After 50 minutes, gelled and tacky. After 16 hours the polymer hardened and dried. No dissolution into water was observed after 16 hours.

In the following products, 20A was formed by premixing mPDA (10.862 gm) and diethylenetriamine (DETA) (10.323 gm) at 1:1 mole ratio. After heating for 2 hours at 50° C., the mixture is amber clear solution. DETA is available from Aldrich as diethylenetriamine reagent plus, 99%, CAS#111-40-0.

Sixth aromatic diamine product: 9D (4.554 gm) 30A (0.448 gm), Dytek DCH99 (0.303 gm), and PEI-800 (0.171 gm) were mixed. Temperature rose to 38° C. from 22° C. with in 2 minutes. After 4 minutes straw was filled. After 6 minutes, add R.O. water into the vial with leftover compound. After 15 min, dough yet very sticky, after 30 minutes it was hard and tacky, after 1 hours, the mixture had a thermoplastic elastomer like finish and dried to touch. After 20 hours the polymer had hardened like a rock. After 20 hours, no dissolution into water observed in the vial.

Seventh aromatic diamine product: 9D (2.875 gm), 20A (0.396 gm) and PEI-800 (0.352 gm). Temperature rose up to 41° C. from 22° C. in 2 minutes. After 3.5 minutes mixture was viscous, the filled straw pulling fibers. After 10 minutes, the mixture was harder and slightly sticky. After 13 minutes the hardened mixture was somewhat tacky. After 20 minutes the hardened compound was not tacky.

Eight aromatic diamine product: 20A (0.699 gm) and 9D) (4.602 gm) were mixed. Temperature rose to 35° C. Straw was filled after 8 minutes. The compound hardened after 35 minutes but was still sticky. After 1 hour the solution was hardened and not tacky.

In the following products composition 23A is a white suspension rather than a clear solution of Melamine (white powder) in DETA (watery liquid) at 1:1 mole ratio. C066 is a 1:1 weight ratio of E(2)BisDA and BisGA. Melamine is C3H6N6. (6 members heterocyclic ring structure with 3 pendent primary amine groups, available from Aldrich (CAS #108-78-1).

Ninth aromatic diamine product: 9D (4.902 gm) and 23A (0.569 gm) were mixed. Temperature rose to 33° C. Straw was filled after 7 minutes. After 30 minutes, the compound was still soft and sticky.

Tenth aromatic diamine product: DETA (0.271 gm) and E(1.5)BisDA (1.837 gm) were mixed. Temperature rose to 36° C. from 22° C. in 2 minutes. After 2 hours in 37° C. the compound was solid and not sticky.

Eleventh aromatic diamine product: DETA (0.337 gm) and E(1.5) BisDA: (1.856 gm) were mixed. Temperature rose to 47° C. from 22° C. in 2 min. After 1.5 hours in 37° C. oven, the mixture was solidified and somewhat sticky.

Twelfth aromatic diamine product: 20A (0.436 gm) and E(1.5)BisDA (1.820 gm) were mixed. Temperature rose to 36° C. within 2 minutes. After 1.5 hours in 37° C. oven the mixture was solidified and non-sticky.

Thirteenth aromatic diamine product: 20A (0.357 gm) and glycidylmethacrylate (0.728 gm) were mixed. No reaction was observed after 10 minutes at room temperature with vigorous stirring, Heated on a hotplate (43° C.) for 1 hour. Filled a section of straw while hot. After 1.5 hours the mixture very sticky and highly viscous and glue-like. After 4 hours, the mixture solidified and was still tacky.

Fourteenth aromatic diamine product: 20A (0.917 gm), PEI-800 (0.919 gm) and E(1.5)BisDA (7.200 gm) were mixed. Temperature rose to 44° C. from 22° C. in 2 minutes. Dough time was 5 minutes. After 5 minutes mixture was dry to touch. The mixture was rubbery hard in 15 minutes. After an hour the mixture had the hardness of a thermoplastic elastomer.

Fifteenth aromatic diamine product: 20A (2.157 gm), PEI-800 (0.473 gm), and E(1.5)BisDA (10.867 gm) were mixed. Temperature rose to 50° C. from 22° C. in 3 minutes. Filled straw after 7 minutes was very sticky. After 0.5 hours the mixture solidified as rubbery sticky solid. After 1 hour the mixture was a clear, shiny, somewhat rubbery solid.

The preceding example provides examples of hydrolytically stable cement products of the invention that include an aromatic diamine.

Example 27

The following example provides cement products of the invention that include high glass transition temperature enones. Generally, the products include a triacrylate crosslinker and a resin (Part A) and a curative (Part B).

In one product: Part A includes E(2)BisDA (31.7123 gm or 0.1496 meq), BisGA (18.2877 gm or 0.0756 meq), tris(2-hydroxyethyl) isocyanurate triacrylate (SR368) from Sartomer (5.2101 gm or 0.03544 meq). 4.7282×10−3 meq/gm. Part B includes linear polyethyleneimine (PEI-1) (Aldrich Cat#468533). Both Parts are loaded with 33.34% HA SD1050 powder. The product increases hydrophobicity of polymer and improves compression/dissolution properties of injectable bone cements.

Other Products improve hydrophobicity of polymer are made by combining the following Part A diacrylate or triacrylate with the following Part B curative.

Part A Dicacrylates:
1. E(2)BisDA: Ethoxylated (2) bisphenol A diacrylate (Scientific Polymer Products (SPP)), inhibited with 100 ppm MEHQ, meq=212

2. BisGA: Bisphenol A glycerolate (1 glycerol/phenol) diacrylate, inhibited with 4,500 ppm MEHQ, meq=242
3. DEGDA: Sartomer SR230 diethyleneglycol diacrylate, inhibited with 115 ppm MEHQ, 92.36%, meq=107
4. DPGDA: Sartomer SR508 dipropyleneglycol diacrylate (inhibited with 185 ppm MEHQ), 84%, meq=121
5. IBGDA: Sartomer SR212 1,3-butyleneglycol diacrylate, inhibited with 517 ppm HQ, 80.9%, meq=99
6. 1,4-butanediol diacrylate, tech, 90% (Aldrich), meq=110
7. 1,6-hexanediol diacrylate, tech, 80%, inhibited with 100 ppm MEHQ, meq=141.4
8. trimethylolpropane benzoate diacrylate (Aldrich), inhibited with 1000 ppm MEHQ, meq=173 Part A triacrylates: (crosslinkers)
9. GPTA: Glyceryl propoxy triacrylate (Scientific Polymer Products (SPP)), inhibited by 300 ppm MEHQ, meq=142.67
10. PETA: Pentaerythritol triacrylate (SPP), inhibited by 350 ppm MEHQ) meq=99.43
11. THEICUTA: Sartomer SR-368 Tris(2-hydroxy ethyl) isocyanurate triacrylate, inhibited by 85 ppm MEHQ, solid, 99.96%, meq=141
12. TMPTA: Trimethylolpropane triacrylate (Sigma-Aldrich), inhibited by 100 ppm MEHQ, meq=109

Part B Curatives
13. Polyethyleneimine (PEI-2, Average Molecular Weight 800, branched) meq-43
14. Ethyleneimine, Oligomer Mixture, (PEI-1. Average Molecular Weight 423), with 5-20% 112-57-2 TEPA, meq=43
15. t-DACH: Trans-1,2-diaminocyclohexane, meq=28.5
16. Dytek A: 2-methyl 1,5-pentanediamine, 99% (Sigma-Aldrich), meq=29
17. Spermidine, 99% (Alfa Aesar, Ward Hill, Mass.), meq=29
18. 1,4-diaminobutane, 99% (Aldrich), meq=22
19. Spermine, 97%, (Sigma), meq=33.7

More specifically, a first series of products is made by mixing 1:1 meq ratio of Part A (each of 1-12) and Part B (each of 13-19), respectively. A second series of products is made by mixing 1:1.2 meq ratio of Part A (each of 1-12) and Part B (each of 13-19), respectively. A third series of products is made by mixing 1:0.8 meq ratio of Part A (each of 1-12) and Part B (each of 13-19), respectively.

The preceding example provides cement products of the invention that include high glass transition temperature enones or higher alkyl aliphatic diamines.

Example 28

The following example provides cement products of the invention suitable for hybrid reactions that includes Michael additions and free radical polymerization.

In the following products: Part 26A is a premix of BisGMA and E(2)BisDA (1:2 mole ratio) (e.g., made with BisGMA (52.512 gm) and E(2)BisDMA (90.544 gm). Part 26B is a premix of E(2)BisDA and BisGA made by mixing BisGA (48.642 gm) and E(2)BisDA (85.224 gm).

For the first series of hybrid products: Part A1 is made by mixing 1:1 (w/w) of 26A and 26B to make (combined acrylates and methacrylates) with 0.004365 meq/gm (229 dalton/mole equivalent). The mixture is doped with 0.05% (w/w) of N—N-dimethyl-p-toluidine to make Part A1. Part B1 includes PEI-1 doped with 10%, 5%, or 2.5% (w/w) benzoyl peroxide (BPO, 75% (w/w) in water from Alfa Aesar, Ward Hill, Mass.). Part A1 is mixed with each of the three BPO-doped versions of Part B at a ratio of 6:1 (w/w) or 12:1 (w/w) to make six hybrid products.

For the second series of hybrid products: Part A2 is made by mixing 70.0 gm of 26A with 14.267 gm glyceryl propoxy triacrylate (GPTA) on a hot plate set to about 50° C.) so as to de-gas until a clear warm and low viscose fluid is obtained. The resulting product has 0.004806 meq/gm (208 dalton/mole equivalent). This product is further mixed with 26B in 1:1 (w/w) ratio to form Part A2, which has meq of 215 dalton. Part A2 is doped with 0.05% DMPT and mixed with the same Part B1 set forth above in the following ratios: PartA2:PartB1=5:1 (w/w) and Part A2:Part B1=10:1 (w/w)

Example 29

The following example provides a cement product of the invention.

Poly[(phenyl glycidyl ether)-co-formaldehyde] (PPGEF) (CAS #28064-14-4) 14.218 gm was dissolved in 16.727 gm of ethoxylated (2) bisphenol A diacrylate (E(2)BisDA) (CAS#64401-02-1), heated to 60° C. and stirred to a homogeneous solution. The solution was cooled to room temperatures to yield 28.600 gm of hybrid Resin A.

Figure 26:
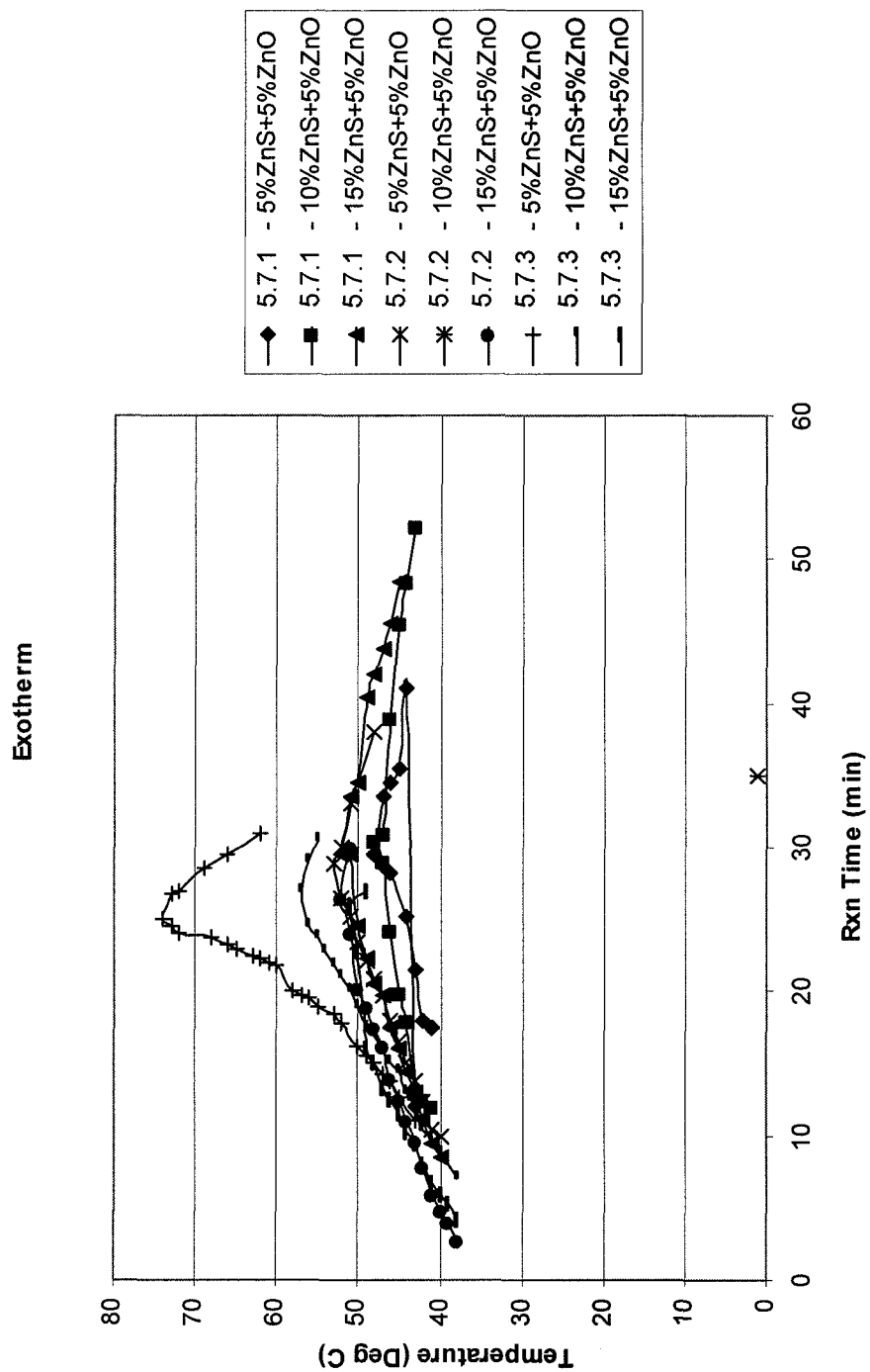
FIG. 26 is graph showing temperature rise relative to time for compositions of the invention that include the indicated epoxy-containing first component and the indicated amounts of ZnS and ZnO.

In a 60 ml NALGENE™ PP flat bottom bottle, 4.704 gm of PEI-800 was added to Resin A with vigorous stirring for 30 seconds. Stirred product was poured into SS molds. Within 5.5 minutes (work time) specimens formed with a diameter of one quarter inch and length of one half inch. SS molds were sealed at both ends with a piece of SS block each. Molds were then clamped and placed in a 37° C. incubator oven for curing. The SS molds were opened after 2 hours and specimens were punched out from the molds. They were divided into 2 trays. One filled with 1×SBF and covered. While the other trays were exposed to air. Both trays were placed in a 37° C. oven before subject to compression testing. Compression testing results are shown in FIG. 26. Each data point is an average of tests on 5 specimens. Compression mechanical strength is in the range of 85 MPa for dried control specimen and 75 MPa for 1×SBF body temperature soaked specimen. Both are above a specification for weight bearing bone cement. In a experiment, an exothermic temperature rise was determined to be around 45° C. within 7-10 minutes. The cement product set hard after 1 hour.

The foregoing example demonstrates a cement product of the invention with good hardness and excellent dimension stability in 1×SBF.

Example 30

The following example provides a cement product of the invention with a first component that includes an isocyanate and a second component that includes a hindered amine.

In a 20 ml vial, 1.234 gm of bisphenylisocyanate methylene (MG-0725A) from Dow Corning (Midland, Mich.) was reacted with 2.725 gm of aspartic ester (Desmophen NH 1420) from Bayer (Pittsburgh, Pa.). The reaction was stirred to a homogenous mixture within 1 minute. Temperature rose from 25° C. to 37° C. in 1 minute. Temperature reached a maximum at 45° C. after four minutes. The working time was 2 minutes and the reaction become a hard dough in 4 minutes and 15 seconds. The cement product was completely set (rock hard solid) in 10 minutes.

Example 31

The following example provides a cement product of the invention.

In a 20 ml vial, 1.1046 gm of trimethylolpropane triacrylate (TMPTA) (Sigma-Aldrich) was reacted with 0.6766 gm of Dytek A (Sigma-Aldrich). The reaction was stirred to a homogenous mixture within 1 minute. The temperature rose from 25° C. to 53° C. in 2 minute. The working time was 10 minutes and the neat cement set to dried to touch in 20 minutes.

Example 32

The following example provides a cement product of the invention that comprises a second component with a naturally occurring amine.

In a 20 ml vial, 1.3294 gm of 1,4-butanedioldiacrylate from Aldrich, was added with 0.6638 gm trimethylolpropane triacrylate (TMPTA) from Sigma-Aldrich. The mixture was stirred for 30 second, it was then reacted with 0.526 gm of spermidine from Alpha Aesar (Ward Hill, Mass.), and the reaction was stirred to homogenous mixture within 1 minute. The temperature rose from 25' C to 57° C. in 2 minute. The working time was 3 minutes and the neat cement set to dried to touch in 5 minutes.

Example 33

The following example provides another cement product of the invention that comprises a second component with a naturally occurring amine.

In a 20 ml vial, 1.3924 gm 1,4-butanediol diacrylate from Aldrich was reacted with 0.4274 gm of spermidine from Alpha Aesar. The mixture was stirred to homogenous mixture within 1 minute. The temperature rose from 25° C. to 48° C. in 2 minutes. The working time was 10 minutes and the neat cement set dried to touch in 30 minutes.

The foregoing example demonstrates the desirable exotherm, set time, and hardness properties of a cement product that includes an isocyanate and a hindered amine.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An orthopedic cement product comprising:
    a first component comprising a polymerizable resin that comprises two or more acrylate groups;
    a second component comprising a compound selected from the group consisting of putrescine (1,4-diaminobutane), spermidine, and spermine; and
    a bioceramic filler;
    wherein the first component and second component are capable of reacting with each other in a polymerization reaction to produce an orthopedic or dental cement,
    wherein when the first component and second component are reacted together in a polymerization reaction at room temperature and allowed to set at about 37° C., the reaction does not exceed a maximum temperature of 60° C. for a period of one minute; and
    wherein the cement product after setting has a compressive strength of about 20 MPa to about 250 MPa.

2. The cement product of claim 1, wherein the first component comprises a compound selected from the group consisting of bisphenol A glycerolate di(meth)acrylate, non-alkoxylated trimethylpropane tri(meth)acrylate (TMPT(M)A), ethoxylated(15) TMPT(M)A, ethoxylated (9) TMPT(M)A, ethoxylated (6) TMPTA, ethoxylated (3) TMPTA, propoxylated (3) TMPT(M)A, propoxylated (6) TMPT(M)A, propoxylated (5) glycerol ethoxylated bisphenol-A-triacrylate, ethoxylated (2) bisphenol A diacrylate (E(2)Bis)A), ethoxylated(4) bisphenol A diacrylate (E(4)BisDA), trimethylolpropane benzoate diacrylate, pentaerythritol triacrylate, pentaerythritoltetraacrylate, butanedioldiacrylate, hexanedioldiacrylate and mixtures thereof.

3. The cement product of claim 1, wherein the first component comprises trimethylolpropane triacrylate.

4. The cement product of claim 1, wherein the first component comprises non-alkoxylated pentaerythritol triacrylate.

5. The cement product of claim 1, wherein the first component comprises E(2)Bis)A, E(4)BisDA, trimethylolpropane benzoate diacrylate, 1,4-butandioldiacrylate, 1,3-butanedioldiacrylate, 1,6-hexanediol diacrylate, or a mixture thereof.

6. The cement product of claim 1, wherein the second component further comprises one or more synthetic polyamine selected from the group consisting of 2-methyl-1,5-pentamethylenediamine, 2-ethyl-1,3-trimethylenediamine, N-(3-Aminopropyl)-1,3-propanediamine, diethylenetriamine (DETA), triethylenetetramine (TETA), and polyethyleneimine (PEI).

7. The cement product of claim 1, wherein
    the first component comprises trimethylolpropane triacrylate, and
    the second component further comprises 2-methyl-1,5-pentamethylenediamine.

8. The cement product of claim 7, wherein
    the first component comprises bisphenol A diglycidyl ether 33-67% w/w, trimethylolpropane triacrylate 33-67% w/w, and, optionally, trimethylolpropane benzoate diacrylate 0-33% w/w; and
    the second component comprises a mixture of spermidine in an amount of at least 33% w/w and 2-methyl-1,5-pentamethylenediamine in an amount up to 67% w/w.

9. The cement product of claim 1, wherein
    the first component comprises trimethylolpropane triacrylate; and
    the second component further comprises a polyamine selected from the group consisting of 2-methyl-1,5-pentamethylenediamine, 2-ethyl-1,3-trimethylenediamine, or a combination thereof.

10. The cement product of claim 9, wherein
    the first component comprises sorbitol polyglycidyl ether 0-40% w/w, trimethylolpropane triacrylate in an amount up to 30% w/w, and 1,4-butanediol 0-20% w/w such that the weight percent of sorbitol polyglycidyl ether, the weight percent of trimethylolpropane triacrylate, and the weight percent of 1,4-butanediol total 100% w/w; and
    the second component comprises spermidine 20-100% w/w and a second polyamine compound selected from the group consisting of 2-methyl-1,5-pentamethylenediamine and 2-ethyl-1,3-trimethylenediamine, in an amount up to 80% w/w.

11. The cement product of claim 1, wherein the bioceramic filler comprises tricalcium phosphate, hydroxyapatite, calcium phosphate, or a combination thereof.

* * * * *